(12) United States Patent
Takahashi et al.

(10) Patent No.: US 6,492,364 B1
(45) Date of Patent: Dec. 10, 2002

(54) TRIAZOLO AND DERIVATIVES AS CHEMOKINE INHIBITORS

(75) Inventors: Toshiya Takahashi, Fujisawa (JP); Takayuki Imaoka, Kamakura (JP); Noriko Mori, Yokohama (JP); Masayuki Kaneko, Kamakura (JP); Koh Tanida, Kamakura (JP); Yuichi Torii, Kamakura (JP)

(73) Assignee: Toray Industries, Inc., Tokyo (JP)

( * ) Notice: Subject to any disclaimer, the term of this patent is extended or adjusted under 35 U.S.C. 154(b) by 0 days.

(21) Appl. No.: 09/601,620

(22) PCT Filed: Dec. 3, 1999

(86) PCT No.: PCT/JP99/06792

§ 371 (c)(1), (2), (4) Date: Sep. 22, 2000

(87) PCT Pub. No.: WO00/34278

PCT Pub. Date: Jun. 15, 2000

(30) Foreign Application Priority Data

Dec. 4, 1998 (JP) ............................ 10-361862

(51) Int. Cl.⁷ ...................... A61K 31/53; A61K 31/497; C07D 487/00; C07D 239/70; C07D 515/00
(52) U.S. Cl. .................. 514/243; 514/250; 514/252.16; 514/267; 514/293; 544/183; 544/184; 544/251; 544/252; 544/346; 544/361; 546/82; 546/84; 546/85; 546/86
(58) Field of Search ................................. 514/243, 250, 514/252.16, 267, 293; 544/183, 184, 251, 252, 346, 361; 546/82, 84, 85, 86

(56) References Cited

U.S. PATENT DOCUMENTS 4,472,400 A * 9/1984 Tully et al. ................. 514/212
5,478,823 A * 12/1995 Shibayama et al. ..... 514/217.03
5,683,998 A * 11/1997 Shibayama et al. ......... 514/218

FOREIGN PATENT DOCUMENTS

JP     9249566     9/1997

OTHER PUBLICATIONS

James A. Bonini et al.; DNA and Cell Biology; vol. 16, No. 10, (1997); pp. 1249–1256.
Andrew D. Luster, M.D., Ph.D.; The New England Journal of Medicine; vol. 338, No. 7 (1998); pp. 436–445.

Donald N. Cook et al.; Science, vol. 269; Sep. 15, 1995; pp. 1491, 1583–1585.

Ji–Liang Gao et al.; The Journal of Experimental Medicine; vol. 185, No. 11; Jun. 2, 1997; pp. 1959–1968.

Landin Boring et al.; The Journal of Clinical Investigation; vol. 100, No. 10; Nov. 1997; pp. 2552–2561.

Marc E. Rothenberg et al.; J. Exp. Med.; vol. 185, No. 4; Feb. 17, 1997; pp. 785–790.

Marco Baggiolini et al.; Annu. Rev. Immunol.; (1997); 15; pp. 675–705.

Barrett J. Rollins; Blood; vol. 90, No. 3; Aug. 1, 1997; pp. 909–928.

* cited by examiner

Primary Examiner—Mukund J. Shah
Assistant Examiner—Tamthom N. Truong
(74) Attorney, Agent, or Firm—Birch, Stewart, Kolasch & Birch, LLP

(57) ABSTRACT

Novel triazolo derivatives represented by the following formula and pharmaceutically acceptable salts thereof, as well as chemokine inhibitors containing the same as an effective component. These are useful as therapeutic agents for allergic diseases such as bronchial asthma and atopic dermatitis; therapeutic agents for inflammatory diseases such as chronic rheumatoid arthritis; therapeutic agents for autoimmune diseases such as ulcerative colitis and nephritis; and as anti-AIDS drugs.

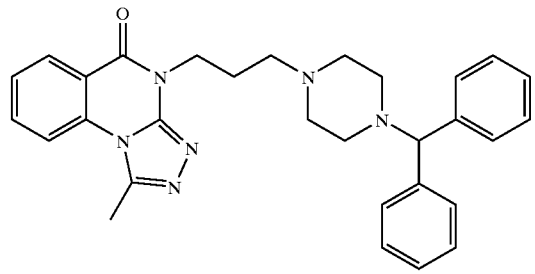

13 Claims, No Drawings

TRIAZOLO AND DERIVATIVES AS CHEMOKINE INHIBITORS

This application is the national phase under 35 U.S.C. § 371 of PCT International Application No. PCT/JP99/06792 which has an International filing date of Dec. 3, 1999, which designated the United States of America.

TECHNICAL FIELD

The present invention relates to novel triazolo derivatives, pharmaceutically acceptable salts thereof, chemokine inhibitors, particularly CC chemokine inhibitors, containing the same as effective components.

BACKGROUND ART

It is well-known that in many inflammatory diseases, infiltration of leukocytes such as macrophages, neutrophils, eosinophils and lymphocytes into the inflammatory site is observed. It is thought that a physiologically active substance called chemotactic factor plays a role in the tissue accumulation of leukocytes. In particular, it has been reported that chemokines known as chemotactic cytokines induce not only infiltration of leukocytes, but also degranulation of leukocytes, production of active oxygen and adhesion reaction, and play central roles in the chemotaxis and activation of leukocytes (e.g., The New England Journal of Medicine, Vol. 338, pp. 436–445, 1998).

Chemokines are classified into 4 subgroups, i.e., C chemokines, CC chemokines, CXC chemokines and CXXXC chemokines, depending on the characteristics of the amino acid sequences (e.g., Blood, Vol. 90, pp. 909–928, 1997).

It is known that lymphotactins, to which C chemokines belong have chemotactic activities to T lymphocytes, while CC chemokines induce chemotactic activities to leukocytes other than nuetrophils, such as monocytes, lymphocytes, eosinophils, basophils and NK cells. CXC chemokines have chemotactic activities mainly to neutrophils and CXXC chemokines have chemotactic activities mainly to NK cells (e.g., The New England Journal of Medicine, Vol. 338, pp. 436–445, 1998). Such a cell specificity suggests that among these subgroups of chemokines, CC chemokines play important roles in the diseases including allergic diseases such as bronchial asthma and atopic dermatitis, chronic rheumatoid arthritis, sarcoidosis, pulmonary fibrosis, bacterial pneumonia, nephritis, atherosclerosis, ulcerative colitis, psoriasis, viral meningitis and AIDS. For example, in mice in which MIP-1α, one of the CC chemokines, is knocked out, the pneumonia induced by infection with influenza virus is reduced (Science, Vol. 269, pp. 1583–1585, 1995). In addition, it is known that in mice in which CCR1, one of the receptors of CC chemokines, is knocked out, the response by helper T cells type 2 which give important contribute to onset of atopic diseases is reduced (The Journal of Experimental Medicine, Vol. 185, pp. 1959–1968, 1997), and that in mice in which CCR2 is knocked out, delayed hypersensitivity reaction and response by helper T cells type 1 is reduced (The Journal of Clinical Investigation, Vol. 100, pp. 2552–2561, 1997). Further, it is known that in mice in which eotaxin, one of CC chemokines, is knocked out, tissue accumulation of eosinophils, which play important roles as effector cells in allergic diseases, occurs (The Journal of Experimental Medicine, Vol. 185, pp. 785–790, 1997). Further, it has been reported that CCR5 and CCR3, which are CC chemokine receptors, are cofactors in infection of AIDS virus, and that RANTES, MIP-1α and MIP-1β, which are CC chemokines prevent infection of AIDS virus (e.g., Annual Review of Immunology, Vol. 15, pp. 675–705, 1997).

Thus, drugs which inhibit activities of such chemokines are expected to be useful as prophylactic or therapeutic agents against these diseases. So far, 10 types of CC chemokine receptors (CCR), i.e., CCR1 to CCR10 are known (e.g., The New England Journal of Medicine, Vol. 338, pp. 436–445, 1998; and DNA and Cell Biology, Vol. 10, pp. 1249–1256, 1997). As for low molecular weight compounds which act on these receptors, although an inhibitor against CCR1 has been reported (e.g., Japanese Laid-open Patent Application (Kokai) No. 9-249566), low molecular weight compounds against other receptors as well as application thereof to therapeutic agents have not been reported.

DISCLOSURE OF THE INVENTION

An object of the present invention is to discover a substance which inhibits the actions of CC chemokines, thereby enabling prophylaxis and therapy of inflammatory diseases caused by infiltration by leukocytes such as monocytes, lymphocytes, acidophils, basophils and NK cells.

The present inventors intensively studied to discover that specific novel triazolo derivatives and pharmaceutically acceptable salts thereof have activities to inhibit actions of CC chemokines, thereby completing the present invention.

That is, the present invention provides a triazolo derivative of the Formula I:

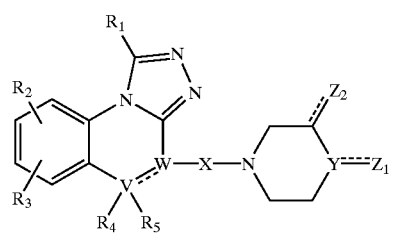

(wherein W represents a carbon atom or a nitrogen atom, X represents a $C_2$–$C_6$ straight chain alkyl group, a $C_3$–$C_8$ branched alkyl group, a $C_2$–$C_6$ fluoroalkyl group, Formula II:

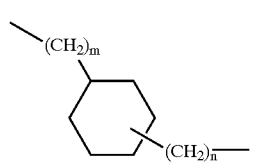

(wherein m and n represent integers of 0 to 6, and —$(CH_2)_n$— is bound to the position of any one of 2-, 3- and 4-position in the cyclohexane ring)

or Formula III:

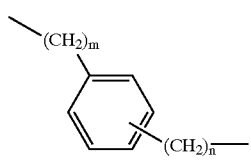

(wherein m and n represent integers of 0 to 6, and —$(CH_2)_n$— is bound to the position of any one of 2-, 3- and 4-position in the benzene ring);
Y represents a carbon atom or a nitrogen atom; ... represents a single bond or a double bond; $Z_1$ and $Z_2$, which may or may not simultaneously exist, each represents $C_6$–$C_{18}$ substituted or non-substituted cyclohexyl group, indole-3-yl group, imidazoyl group, furyl group, thienyl group, pyrrolyl group, pyridyl group or $QCR_6R_7R_8$, with the proviso that in cases where $Z_1$ and $Z_2$ represent $QCR_6R_7R_8$, Q and $R_6$ may or may not exist, and when Q exists, Q is selected from the group consisting of an oxygen atom, a sulfur atom and a nitrogen atom; and when $R_6$ exists, $R_6$ represents hydrogen or hydroxyl group; $R_7$ and $R_8$, which may be the sane or different, represent hydrogen, $C_1$–$C_6$ straight alkyl group, $C_3$–$C_8$ branched alkyl group, or one selected from the group consisting of $C_6$–$C_{16}$ substituted or non-substituted phenyl group, $C_{10}$–$C_{16}$ substituted or non-substituted naphthyl group and $C_6$–$C_{16}$ substituted or non-substituted cycloalkyl group, which phenyl group, naphthyl group or cycloalkyl group is bound through $C_0$–$C_6$ methylene chain; V represents a carbon atom or a nitrogen atom; $R_1$ represents $C_1$–$C_6$ straight alkyl group or aryl group; $R_2$ and $R_3$, which may or may not exist and which may be the same or different, each is selected from the group consisting of $C_1$–$C_6$ straight alkyl group, $C_1$–$C_6$ straight alkoxyl group, $C_3$–$C_8$ branched alkyl group, $C_3$–$C_8$ branched alkoxyl group, hydroxyl group; chloro, bromo, fluoro, amino group, monoalkylamino group in which the alkyl group has 1 to 6 carbon atoms, diaikylamino group in which each alkyl group has 2 to 6 carbon atoms, trifluoromethyl group, and nitro group; in cases where V and W are carbon atoms and where V and W are bound through double bond, $R_4$ does not exist, and $R_5$ represents hydrogen, $C_1$–$C_6$ straight alkyl group, $C_1$–$C_6$ straight alkoxyl group, $C_3$–$C_8$ branched alkyl group, $C_3$–$C_8$ branched alkoxyl group, or represents one selected from the group consisting of $C_6$–$C_{16}$ substituted or non-substituted phenyl group, $C_{10}$–$C_{16}$ substituted or non-substituted naphthyl group and $C_6$–$C_{16}$ substituted or non-substituted cycloalkyl group, which phenyl group, naphthyl group or cycloalkyl group is bound through $C_0$–$C_6$ methylene chain; in cases where V is nitrogen atom and W is carbon atom and where V and W are bound through double bond, both $R_4$ and $R_5$ do not exist; in cases where V is carbon atom, W is nitrogen atom or carbon atom, and V and W are bound through single bond, $R_4$ and $R_5$ cooperatively represent oxo group; wherein the substituent(s) in said substituted phenyl group, substituted naphthyl group and substituted cycloalkyl group is(are) 1 to 5 $C_1$–$C_6$ straight alkyl group(s), $C_3$–$C_6$ branched alkyl group(s), phenyl group(s), phenoxy group(s), naphthyl group(s), cyclopentyl group(s) or cyclohexyl group(s)) or a pharmaceutically acceptable salt thereof. The present invention also provides a chemokine inhibitor comprising the above-described triazolo derivative of the present invention or a pharmaceutically acceptable salt thereof as an effective component.

The triazolo derivatives and pharmaceutically acceptable salts thereof according to the present invention inhibit actions of chemokines, particularly CC chemokines, of which actions are mediated by chemokine receptors such as CCR1, CCR2, CCR3 and the like. Therefore, the triazolo derivatives and pharmaceutically acceptable salts thereof according to the present invention are useful as therapeutic agents for allergic diseases such as bronchial asthma and atopic dermatitis, therapeutic agents for inflammatory diseases such as chronic rheumatoid arthritis, autoimmune diseases such as nephritis and ulcerative colitis, and as anti-AIDS drugs, and useful for prophylaxis and therapy of various diseases other than those mentioned above, in which chemokines are thought to participate.

BEST MODE FOR CARRYING OUT THE INVENTION

As mentioned above, the triazolo derivatives according to the present invention are represented by the above-described Formula I. In Formula I, W represents a carbon atom or a nitrogen atom. X represents $C_2$–$C_6$ straight alkyl group which is ethyl, n-propyl, n-butyl, n-pentyl or n-hexyl group; $C_3$–$C_8$ branched alkyl group such as 1-methylethyl, 2-methylethyl, 1,1-dimethylethyl, 1,2-dimethylethyl, 2,2-dimethylethyl, 1-methylpropyl, 2-methylpropyl, 3-methylpropyl, 1,1-dimethylpropyl, 2,2-dimethylpropyl, 3,3-dimethylpropyl, 1,2-dimethylpropyl, 1,3-dimethylpropyl, 1-methylbutyl, 2-methylbutyl, 3-methylbutyl, 4-methylbutyl, 1,1-dimethylbutyl, 2,2-dimethylbutyl, 3,3-dimethylbutyl, 4,4-dimethylbutyl, 1,2-dimethylbutyl, 1,3-dimethylbutyl, 1,4-dimethylbutyl, 2,3-dimethylbutyl, 2,4-dimethylbutyl, 1-methylpentyl, 2-methylpentyl, 3-methylpentyl, 4-methylpentyl, 5-methylpentyl, 1,1-dimethylpentyl, 2,2-dimethylpentyl, 3,3-dimethylpentyl, 4,4-dimethylpentyl, 5,5-dimethylpentyl, 1,2-dimethylpentyl, 1,3-dimethylpentyl, 1,4-dimethylpentyl, 1,5-dimethylpentyl, 2,3-dimethylpentyl, 2,4-dimethylpentyl, 2,5-dimethylpentyl, 3,4-dimethylpentyl, 3,5-dimethylpentyl, 4,5-dimethylpentyl, 1-methylhexyl, 2-methylhexyl, 3-methylhexyl, 4-methylhexyl, 5-methylhexyl, 6-methylhexyl, 1,1-dimethylhexyl, 2,2-dimethylhexyl, 3,3-dimethylhexyl, 4,4-dimethylhexyl, 5,5-dimethylhexyl, 6,6-dimethylhexyl, 1,2-dimethylhexyl, 1,3-dimethylhexyl, 1,4-dimethylhexyl, 1,5-dimethylhexyl, 1,6-dimethylhexyl, 2,3-dimethylhexyl, 2,4-dimethylhexyl, 2,5-dimethylhexyl, 2,6-dimethylhexyl, 3,4-dimethylhexyl, 3,5-dimethylhexyl, 3,6-dimethylhexyl, 4,5-dimethylhexyl and 5,6-dimethylhexyl; $C_2$–$C_6$ fluoroalkyl group such as 1-fluoroethyl, 2-fluoroethyl, 1,1-difluoroethyl, 2,2-difluoroethyl, 1,2-difluoroethyl, 1-fluorobutyl,2-fluorobutyl, 3-fluorobutyl, 4-fluorobutyl, 1,1-difluorobutyl, 2,2-difluorobutyl, 3,3-difluorobutyl, 4,4-difluorobutyl, 1,2-difluorobutyl, 1,3-difluorobutyl, 1,4-difluorobutyl, 2,3-difluorobutyl, 2,4-difluorobutyl, 1-fluorohexyl, 2-fluorohexyl, 3-fluorohexyl, 4-fluorohexyl, 5-fluorohexyl, 5-fluorohexyl, 1,1-difluorohexyl, 2,2-difluorohexyl, 3,3-difluorohexyl, 4,4-difluorohexyl, 5,5-difluorohexyl, 6,6-difluorohexyl, 1,2-difluorohexyl, 1,3-difluorohexyl, 1,4-difluorohexyl, 1,5-difluorohexyl, 1,6-difluorohexyl, 2,3-difluorohexyl, 2,4-difluorohexyl, 2,5-difluorohexyl, 2,6-difluorohexyl, 3,4-difluorohexyl, 3,5-difluorohexyl, 3,6-difluorohexyl, 4,5-difluorohexyl, 4,6-difluorohexyl and 5,6-difluorohexyl groups; Formula II:

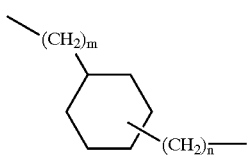

(wherein m and n represent integers of 0 to 6, and —$(CH_2)_n$— is bound to the position of any one of 2-, 3- and 4-position in the cyclohexane ring)

or Formula III:

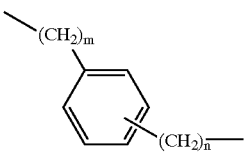

(wherein m and n represent integers of 0 to 6, and —$(CH_2)_n$— is bound to the position of any one of 2-, 3- and 4-position in the benzene ring).

Y represents a carbon atom or a nitrogen atom; ⋯ represents single bond or double bond; $Z_1$ and $Z_2$, which may or may not exist simultaneously, each represents $C_6$–$C_{18}$ substituted or non-substituted cyclohexyl group such as cyclohexyl, 2-methylcyclohexyl, 3-methylcyclohexyl, 4-methylcyclohexyl, 2,2-dimethylcyclohexyl, 3,3-dimethylcyclohexyl, 4,4-dimethylcyclohexyl, 2,3-dimethylcyclohexyl, 2,4-dimethylcyclohexyl, 2-phenylcyclohexyl, 3-phenylcyclohexyl, 4-phenylcyclohexyl, 2-naphthylcyclohexyl, 3-naphthylcyclohexyl, 4-naphthylcyclohexyl, 2-phenylcyclohexyl, 3-phenoxycyclohexyl and 4phenoxycyclohexyl groups; indole-3-yl group; imidazoyl group; furyl group; thienyl group; pyrrolyl group; pyridyl group; or $QCR_6R_7R_8$, with the proviso that in cases where $Z_1$ and $Z_2$ represent $QCR_6R_7R_8$, Q and $R_6$ may or may not exist, and when Q exists, Q is selected from the group consisting of oxygen atom, sulfur atom and nitrogen atom; and when $R_6$ exists, $R_6$ represents hydrogen or hydroxyl group; $R_7$ and $R_8$ represent, which may be the same or different, represent hydrogen, $C_1$–$C_6$ straight alkyl group which is methyl, ethyl, n-propyl, n-butyl, n-pentyl or n-hexyl group; $C_3$–$C_8$ branched alkyl group such as 1-methylethyl, 2methylethyl, 1,1-dimethylethyl, 1,2-dimethylethyl, 2,2-dimethylethyl, 1-methylpropyl, 2-methylpropyl, 3-methylpropyl, 1,1-dimethylpropyl, 2,2-dimethylpropyl, 3,3-dimethylpropyl, 1,2-dimethylpropyl, 1,3-dimethylpropyl, 1-methylbutyl, 2-methylbutyl, 3-methylbutyl, 4-methylbutyl, 1,1-dimethylbutyl, 2,2-dimethylbutyl, 3,3-dimethylbutyl, 4,4-dimethylbutyl, 1,2-dimethylbutyl, 1,3-dimethylbutyl, 1,4-dimethylbutyl, 2,3-dimethylbutyl, 2,4-dimethylbutyl, 1-methylpentyl, 2-methylpentyl, 3-methylpentyl, 4-methylpentyl, 5-methylpentyl, 1,1-dimethylpentyl 2,2-dimethylpentyl, 3,3-dimethylpentyl, 4,4-dimethylpentyl, 5,5-dimethylpentyl, 1,2-dimethylpentyl, 1,3-dimethylpentyl, 1,4-dimethylpentyl, 1,5-dimethylpentyl, 2,3-dimethylpentyl, 2,4-dimethylpentyl, 2,5-dimethylpentyl, 3,4-dimethylpentyl, 3,5-dimethylpentyl, 4,5-dimethylpentyl, 1-methylhexyl, 2-methylhexyl, 3-methylhexyl, 4-methylhexyl, 5-methylhexyl, 6-methylhexyl, 1,1-dimethylhexyl, 2,2-dimethylhexyl, 3,3-dimethylhexyl, 4,4-dimethylhexyl, 5,5-dimethylhexyl, 6,6-dimethylhexyl, 1,2-dimethylhexyl, 1,3-dimethylhexyl, 1,4-dimethylhexyl, 1,5-dimethylhexyl, 1,6-dimethylhexyl, 2,3-dimethylhexyl, 2,4-dimethylhexyl, 2,5-dimethylhexyl, 2,6-dimethylhexyl, 3,4-dimethylhexyl, 3,5-dimethylhexyl, 3,6-dimethylhexyl, 4,5-dimethylhexyl and 5,6-dimethylhexyl groups; $C_6$–$C_{16}$ substituted or non-substituted phenyl group bound through $C_0$–$C_6$ methylene chain, such as phenyl, benzyl, phenylethyl, phenylpropyl, phenylbutyl, phenylpentyl, phenylhexyl, 2-methylphenyl, 2-methylbenzyl, 2-(2-methylphenyl)ethyl, 3-(2-methylphenyl)propyl, 4-(2-methylphenyl)butyl, 5-(2-methylphenyl)pentyl, 6-(2-methylphenyl)hexyl, 3-methylphenyl, 3-methylbenzyl, 2-(3-methylphenyl)ethyl, 4-(3-methylphenyl)propyl, 4-(3-methylphenyl)butyl, 5-(3-methylphenyl)pentyl, 6-(3-methylphenyl)hexyl, 4-methylphenyl, 4-methylbenzyl, 2-(4-methylphenyl)ethyl, 3-(4-methylphenyl)propyl, 4-(4-methylphenyl)butyl, 5-(4-methylphenyl)pentyl, 6-(4-methylphenyl)hexyl, 2-propylphenyl, 2-propylbenzyl, 2-(2-propylphenyl)ethyl, 3-(2-propylphenyl)propyl, 4-(2-propylphenyl)butyl, 5-(2-propylphenyl)pentyl, 6-(2-propylphenyl)hexyl, 3-propylphenyl, 3-propylbenzyl, 2-(3-propylphenyl)ethyl, 3-(3-propylphenyl)propyl, 4-(3-propylphenyl)butyl, 5-(3-propylphenyl)pentyl, 6-(3-propylphenyl)hexyl, 4-propylphenyl, 4-propylbenzyl, 2-(4-propylphenyl)ethyl, 3-(4-propylphenyl)propyl, 4-(4-propylphenyl)butyl, 5-(4-propylphenyl)pentyl, 6-(4-propylphenyl)hexyl, 2-cyclopentylphenyl, 2-cyclopentylbenzyl, 2-(2-cyclopentylphenyl)ethyl, 3-(2-cyclopentylphenyl)propyl, 4-(2-cyclopentylphenyl)butyl, 5-(2-cyclopentylphenyl)pentyl, 6-(2-cyclopentylphenyl)hexyl, 3-cyclopentylphenyl, 3-cyclopentylbenzyl, 2-(3-cyclopentylphenyl)ethyl, 3-(3-cyclopentylphenyl)propyl, 4-(3-cyclopentylphenyl)butyl, 5-(3-cyclopentylphenyl)pentyl, 6-(3-cyclopentylphenyl)hexyl, 4-cyclopentylphenyl, 4-cyclopentylbenzyl, 2-(4-cyclopentylphenyl)ethyl, 3-(4-cyclopentylphenyl)propyl, 4-(4-cyclopentylphenyl)butyl, 5-(4-cyclopentylphenyl)pentyl, 6-(4-cyclopentylphenyl)hexyl, 2-cyclohexylphenyl, 2-cyclohexylbenzyl, 2-(2-cyclohexylphenyl)ethyl, 3-(2-cyclohexylphenyl)propyl, 4-(2-cyclohexylphenyl)butyl, 5-(2-cyclohexylphenyl)pentyl, 6-(2-cyclohexylphenyl)hexyl, 3-cyclohexylphenyl, 3-cyclohexylbenzyl, 2-(3-cyclohexylphenyl)ethyl, 3-(3-cyclohexylphenyl)propyl, 4-(3-cyclohexylphenyl)butyl, 5-(3-cyclohexylphenyl)pentyl, 6-(3-cyclohexylphenyl)hexyl, 4-cyclohexylphenyl, 4-cyclohexylbenzyl, 2-(4-cyclohexylphenyl)ethyl, 3-(4-cyclohexylphenyl)propyl, 4-(4-cyclohexylphenyl)butyl, 5-(4-cyclohexylphenyl)pentyl, 6-(4-cyclohexylphenyl)hexyl, 2-phenyl-phenyl, 2-phenyl-benzyl, 2-(2-phenyl-phenyl)ethyl, 3-(2-phenyl-phenyl)propyl, 4-(2-phenyl-phenyl)butyl, 5-(2-phenyl-phenyl)pentyl, 6-(2-phenyl-phenyl)hexyl, 3-phenyl-phenyl, 3-phenyl-benzyl, 2-(3-phenyl-phenyl)ethyl, 3-(3-phenyl-phenyl)propyl, 4-(3-phenyl-phenyl)butyl, 5-(3-phenyl-phenyl)pentyl, 6-(3-phenyl-phenyl)hexyl, 4-phenyl-phenyl, 4-phenyl-benzyl, 2-(4-phenyl-phenyl)ethyl, 3-(4-phenyl-phenyl)propyl, 4-(4-phenyl-phenyl)butyl, 5-(4-phenyl-phenyl)pentyl, 6-(4-phenyl-phenyl)hexyl, 2-phenoxy-phenyl, 2-phenoxy-benzyl, 2-(2-phenoxy-phenyl)ethyl, 3-(2-phenoxy-phenyl)propyl, 4-(2-phenoxy-phenyl)butyl, 5-(2-phenoxy-phenyl)pentyl, 6-(2-phenoxy-phenyl)hexyl, 3-phenoxy-phenyl, 3-phenoxy-benzyl, 2-(3-phenoxy-phenyl)ethyl, 3-(3-phenoxy-phenyl)propyl, 4-(3-phenoxy-phenyl)butyl, 5-(3-phenoxy-phenyl)pentyl, 6-(3-phenoxy-phenyl)hexyl, 4-phenoxy-phenyl, 4-phenoxy-benzyl, 2-(4-phenoxy-phenyl)ethyl, 3-(4-phenoxy-phenyl)propyl, 4-(4-phenoxy-phenyl)butyl, 5-(4-phenoxy-phenyl)pentyl and 6-(4-phenoxy-phenyl)hexyl groups; $C_{10}$–$C_{16}$ substituted or non-substituted naphthyl group bound through $C_0$–$C_6$ methylene chain, such as naphthyl, naphthylmethyl, naphthylethyl, naphthylpropyl, naphthylbutyl, naphthylpentyl, naphthylhexyl, 2-methylnaphthyl, 2-methylnaphthylmethyl, 2-(2-methylnaphthyl)ethyl, 3-(2-methylnaphthyl)propyl, 4-(2-methylnaphthyl)butyl, 5-(2-methylnaphthyl)pentyl, 6-(2-methylnaphthyl)hexyl, 3-methylnaphthyl, 3-methylnaphthylmethyl, 2-(3-methylnaphthyl)ethyl, 3-(3-methylnaphthyl)propyl, 4-(3-methylnaphthyl)butyl, 5-(3-methylnaphthyl)pentyl, 6-(3-methylnaphthyl)hexyl, 4-methylnaphthyl, 4-methylnaphthylmethyl, 2-(4-methylnaphthyl)ethyl, 3-(4-methylnaphthyl)propyl, 4-(4-methylnaphthyl)butyl, 5-(4-methylnaphthyl)pentyl, 6-(4-methylnaphthyl)hexyl, 2-propylnaphthyl, 2-propyl-5-naphthylmethyl, 2-(2-propylnaphthyl)ethyl, 3-(2-propylnaphthyl)propyl, 4-(2-propylnaphthyl)butyl, 5-(2-propylnaphthyl)pentyl, 6-(2-propylnaphthyl)hexyl, 3-propylnaphthyl, 3-propylnaphthylmethyl, 2-(3-propylnaphthyl)ethyl, 3-(3-propylnaphthyl)propyl, 4-(3-propylnaphthyl)butyl, 5-(3-propylnaphthyl)pentyl, 6-(3-propylnaphthyl)hexyl, 4-propylnaphthyl, 4-propylnaphthylmethyl, 2-(4-propylnaphthyl)ethyl, 3-(4-propylnaphthyl)propyl, 4-(4-propylnaphthyl)butyl, 5-(4-propylnaphthyl)pentyl, 6-(4-propylnaphthyl)hexyl, 2-cyclopentylnaphthyl, 2-cyclopentylnaphthylmethyl, 2-(2-cyclopentylnaphthyl)ethyl, 3-(2-cyclopentylnaphthyl)propyl, 4-(2-cyclopentylnaphthyl)butyl, 5-(2-cyclopentylnaphthyl)pentyl, 6-(2-cyclopentylnaphthyl)hexyl, 3-cyclopentylnaphthyl, 3-cyclopentylnaphthylmethyl, 2-(3-cyclopentylnaphthyl)ethyl, 3-(3-cyclopentylnaphthyl)propyl, 4-(3-cyclopentylnaphthyl)butyl, 5-(3-cyclopentylnaphthyl)pentyl, 6-(3-cyclopentylnaphthyl)hexyl, 4-cyclopentylnaphthyl, 4-cyclopentylnaphthylmethyl, 2-(4-cyclopentylnaphthyl)ethyl, 3-(4-cyclopentylnaphthyl)propyl, 4-(4-cyclopentylnaphthyl)butyl, 5-(4-cyclopentylnaphthyl)pentyl, 6-(4-cyclopentylnaphthyl)hexyl, 2-cyclohexylnaphthyl, 2-cyclohexylnaphthylmethyl, 2-(2-cyclohexylnaphthyl)ethyl, 3-(2-cyclohexylnaphthyl)propyl, 4-(2-cyclohexylnaphthyl)butyl, 5-(2-cyclohexylnaphthyl)pentyl, 6-(2-cyclohexylnaphthyl)hexyl, 3-cyclohexylnaphthyl, 3-cyclohexylnaphthylmethyl, 2-(3-cyclohexylnaphthyl)ethyl, 3-(3-cyclohexylnaphthyl)propyl, 4-(3-cyclohexylnaphthyl)butyl, 5-(3-cyclohexylnaphthyl)pentyl, 6-(3-cyclohexylnaphthyl)hexyl, 4-cyclohexylnaphthyl, 4-cyclohexylnaphthylmethyl, 2-(4-cyclohexylnaphthyl)ethyl, 3-(4-cyclohexylnaphthyl)propyl, 4-(4-cyclohexylnaphthyl)butyl, 5-(4-cyclohexylnaphthyl)pentyl, 6-(4-cyclohexylnaphthyl)hexyl, 2-phenyl-naphthyl, 2-phenyl-naphthylmethyl, 2-(2-phenyl-naphthyl)ethyl, 3-(2-phenyl-naphthyl)propyl, 4-(2-phenyl-naphthyl)butyl, 5-(2-phenyl-naphthyl)pentyl, 6-(2-phenyl-naphthyl)hexyl, 3-phenyl-naphthyl, 3-phenylnaphthylmethyl, 2-(3-phenyl-naphthyl)ethyl, 3-(3-phenyl-naphthyl)propyl, 4-(3-phenyl-naphthyl)butyl, 5-(3-phenyl-naphthyl)pentyl, 6-(3-phenyl-naphthyl)hexyl, 4-phenyl-naphthyl, 4-phenyl-naphthylmethyl, 2-(4-phenyl-naphthyl)ethyl, 3-(4-phenyl-naphthyl)propyl, 4-(4-phenyl-naphthyl)butyl, 5-(4-phenyl-naphthyl)pentyl, 6-(4-phenyl-naphthyl)hexyl, 2-phenoxy-naphthyl, 2-phenoxy-naphthylmethyl, 2-(2-phenoxy-naphthyl)ethyl, 3-(2-phenoxy-naphthyl)propyl, 4-(2-phenoxy-naphthyl)butyl, 5-(2-phenoxy-naphthyl)pentyl, 6-(2-phenoxy-naphthyl)hexyl, 3-phenoxy-naphthyl, 3-phenoxy-naphthylmethyl, 2-(3-phenoxy-naphthyl)ethyl, 3-(3-phenoxy-naphthyl)propyl, 4-(3-phenoxy-naphthyl)butyl, 5-(3-phenoxy-naphthyl)pentyl, 6-(3-phenoxy-naphthyl)hexyl, 4-phenoxy-naphthyl, 4-phenoxy-naphthylmethyl, 2-(4-phenoxy-naphthyl)ethyl, 3-(4-phenoxy-naphthyl)propyl, 4-(4-phenoxy-naphthyl)butyl, 5-(4-phenoxy-naphthyl)pentyl and 6-(4-phenoxy-naphthyl)hexyl groups; or $C_6$–$C_{16}$ substituted or non-substituted cycloalkyl group bound through $C_0$–$C_6$ methylene chain, such as cyclohexyl, cyclohexylmethyl, cyclohexylethyl, cyclohexylpropyl, cyclohexylbutyl, 2-methylcyclohexyl, 2-methylcyclohexylmethyl, 2-methylcyclohexylethyl, 2-methylcyclohexylpropyl, 2,2-dimethylcyclohexyl, 2,2-dimethylcyclohexylmethyl, 2-(2,2-dimethylcyclohexyl)ethyl, 2,3-dimethylcyclohexyl, 2,3-dimethylcyclohexylmethyl, 2-(2,3-dimethylcyclohexyl)ethyl, 3,3-dimethylcyclohexyl, 3,3-dimethylcyclohexylmethyl, 2-(3,3-dimethylcyclohexyl)ethyl, 2-cyclopentylcyclohexyl, 3-cyclopentyl-cyclohexyl, 4-cyclopentyl-cyclohexyl, 2-cyclohexylcyclohexyl, 3-cyclohexyl-cyclohexyl, 4-cyclohexyl-cyclohexyl, 2-phenyl-cyclohexyl, 3-phenyl-cyclohexyl, 4-phenyl-cyclohexyl, 2-phenoxy-cyclohexyl, 3-phenoxy-cyclohexyl, 4-phenoxy-cyclohexyl, 2-benzyl-cyclohexyl, 3-benzyl-cyclohexyl, 4-benzyl-cyclohexyl, 2-benzyloxy-cyclohexyl, 3-benzyloxy-cyclohexyl, 4-benzyloxy-cyclohexyl, 2-naphthyl-cyclohexyl, 3-naphthyl-cyclohexyl, 4-naphthyl-cyclohexyl, 4-naphthyl-cyclohexylmethyl, 2-(4-naphthyl-cyclohexyl)ethyl, 3-(4-naphthyl-cyclohexyl)propyl, 4-(4-naphthyl-cyclohexyl)butyl and 5-(4-naphthyl-cyclohexyl)pentyl, 6-(4-naphthyl-cyclohexyl)hexyl groups.

V represents carbon atom or nitrogen atom. $R_1$ represents $C_1$–$C_6$ straight alkyl which is methyl, ethyl, n-propyl, n-butyl, n-pentyl or n-hexyl group. $R_2$ and $R_3$ may or may not exist, may be the same or different, and each of which represents $C_1$–$C_6$ straight alkyl group which is methyl, ethyl, n-propyl, n-butyl, n-pentyl or n-hexyl group; $C_1$–$C_6$ straight alkoxyl group which is methoxy, ethoxy, n-propyloxy, n-butyloxy, n-pentyloxy or n-hexyloxy group; $C_3$–$C_8$ branched alkyl group such as 1-methylethyl, 2-methylethyl, 1,1-dimethylethyl, 1,2-dimethylethyl, 2,2-dimethylethyl, 1-methylpropyl, 2-methylpropyl, 3-methylpropyl, 1,1-dimethylpropyl, 2,2-dimethylpropyl, 3,3-dimethylpropyl, 1,2-dimethylpropyl, 1,3-dimethylpropyl, 1-methylbutyl, 2-methylbutyl, 3-methylbutyl, 4-methylbutyl, 1,1-dimethylbutyl, 2,2-dimethylbutyl, 3,3-dimethylbutyl, 4,4-dimethylbutyl, 1,2-dimethylbutyl, 1,3-dimethylbutyl, 1,4-dimethylbutyl, 2,3-dimethylbutyl, 2,4-dimethylbutyl, 1-methylpentyl, 2-methylpentyl, 3-methylpentyl, 4-methylpentyl, 5-methylpentyl, 1,1-dimethylpentyl, 2,2-dimethylpentyl, 3;3-dimethylpentyl, 4,4-dimethylpentyl, 5,5-dimethylpentyl, 1,2-dimethylpentyl, 1,3-dimethylpentyl, 4,4-dimethylpentyl, 1,5-dimethylpentyl, 2,3-dimethylpentyl, 2,4-dimethylpentyl, 2,5-dimethylpentyl, 3,4-dimethylpentyl, 3,5-dimethylpentyl, 4,5-dimethylpentyl, 2,-methylhexyl, 2-methylhexyl, 3-methylhexyl, 4-methylhexyl, 5-methylhexyl, 6-methylhexyl, 1,1-dimethylhexyl, 2,2-dimethylhexyl, 3,3-dimethylhexyl, 4,4-dimethylhexyl, 5,5-dimethylhexyl, 6,6-dimethylhexyl, 1,2-dimethylhexyl, 1,3-dimethylhexyl, 1,4-dimethylhexyl, 1,5-dimethylhexyl, 1,6-dimethylhexyl, 2,3-dimethylhexyl, 2,4-dimethylhexyl, 2,5-dimethylhexyl, 2,6-dimethylhexyl, 3,4-dimethylhexyl, 3,5-dimethylhexyl, 3,6-dimethylhexyl, 4,5-dimethylhexyl and 5,6-dimethylhexyl groups; $C_3$–$C_8$ branched alkoxyl group such as 2-methylethoxy, 2,2-dimethylethoxy, 2-methylpropyloxy, 3-methylpropyloxy, 2,2-dimethylpropyloxy, 3,3-dimethylpropyloxy, 2,3-dimethylpropyloxy, 2-methylbutyloxy, 3-methylbutyloxy, 4-methylbutyloxy, 2,2-dimethylbutyloxy, 3,3-dimethylbutyloxy, 4,4-dimethylbutyloxy, 2,3-dimethylbutyloxy, 2,4- dimethylbutyloxy, 2-methylpentyloxy, 3-methylpentyloxy, 4-methylpentyloxy, 5-methylpentyloxy, 2,2-dimethylpentyloxy, 3,3-dimethylpentyloxy, 4,4-dimethylpentyloxy, 5,5-dimethylpentyloxy, 2,3-dimethylpentyloxy, 2,4-dimethylpentyloxy, 2,5-dimethylpentyloxy, 3,4-dimethylpentyloxy, 3,5-dimethylpentyloxy, 4,5-dimethylpentyloxy, 2-methylhexyloxy, 3-methylhexyloxy, 4-methylhexyloxy, 5-methylhexyloxy, 6-methylhexyloxy, 2,2-dimethylhexyloxy, 3,3-dimethylhexyloxy, 4,4-dimethylhexyloxy, 5,5-dimethylhexyloxy, 6,6-dimethylhexyloxy, 2,3-dimethylhexyloxy, 2,4-dimethylhexyloxy, 2,5-dimethylhexyloxy, 2,6-dimethylhexyloxy, 3,4-dimethylhexyloxy, 3,5-dimethylhexyloxy, 3,6-dimethylhexyloxy, 4,5-dimethylhexyloxy and 5,6-dimethylhexyloxy; hydroxyl group, chloro, bromo, fluoro, amino, $C_1$–$C_6$ monoalkylamino, dialkylamino in which each alkyl group has 2 to 6 carbon atoms, trifluoromethyl or nitro.

In cases where V and W are carbon atoms, and the bond between V and W is double bond, $R_4$ does not exist, $R_5$ is hydrogen; $C_1$–$C_6$ straight alkyl group which is 15 methyl, ethyl, n-propyl, n-butyl, n-pentyl or n-hexyl group; $C_1$–$C_6$ straight alkoxyl group which is methoxy, ethoxy, n-propyloxy, n-butyloxy, n-pentyloxy or n-hexyloxy group; $C_3$–$C_8$ branched alkyl group such as 1-methylethyl, 2-methylethyl, 1,1-dimethylethyl, 1,2-dimethylethyl, 2,2-dimethylethyl, 1-methylpropyl, 2-methylpropyl, 3-methylpropyl, 1,1-dimethylpropyl, 2,2-dimethylpropyl, 3,3-dimethylpropyl, 1,2-dimethylpropyl, 1,3-dimethylpropyl, 1-methylbutyl, 2-methylbutyl, 3-methylbutyl, 4-methylbutyl, 1,1-dimethylbutyl, 2,2-dimethylbutyl, 3,3-dimethylbutyl, 4,4-dimethylbutyl, 1,2-dimethylbutyl, 1,3-dimethylbutyl, 1,4-dimethylbutyl, 2,3-dimethylbutyl, 2,4-dimethylbutyl, 1-methylpentyl, 2-methylpentyl, 3-methylpentyl, 4-methylpentyl, 5-methylpentyl, 1,1-dimethylpentyl, 2,2-dimethylpentyl, 3,3-dimethylpentyl, 4,4-dimethylpentyl, 5,5-dimethylpentyl, 1,2-dimethylpentyl, 1,3-dimethylpentyl, 1,4-dimethylpentyl, 1,5-dimethylpentyl, 2,3-dimethylpentyl, 2,4-dimethylpentyl, 2,5-dimethylpentyl, 3,4-dimethylpentyl, 3,5-dimethylpentyl, 4,5-dimethylpentyl, 1-methylhexyl, 2-methylhexyl, 3-methylhexyl, 4-methylhexyl, 5-methylhexyl, 6-methylhexyl, 1,1-dimethylhexyl, 2,2-dimethylhexyl, 3,3-dimethylhexyl, 4,4-dimethylhexyl, 55-dimethylhexyl, 6,6-dimethylhexyl, 1,2-dimethylhexyl, 1,3-dimethylhexyl, 1,4-dimethylhexyl, 1,5-dimethylhexyl, 1,6-dimethylhexyl, 2,3-dimethylhexyl, 2,4-dimethylhexyl, 2,5-dimethylhexyl, 2,6-dimethylhexyl, 3,4-dimethylhexyl, 3,5-dimethylhexyl, 3,6-dimethylhexyl, 4,5-dimethylhexyl and 5,6-dimethylhexyl groups; $C_3$–$C_8$ branched alkoxyl group such as 2-methylethoxy, 2,2-dimethylethoxy, 2-methylpropyloxy, 3-methylpropyloxy, 2,2-dimethylpropyloxy, 3,3-dimethylpropyloxy, 2,3-dimethylpropyloxy, 2-methylbutyloxy, 3-methylbutyloxy, 4-methylbutyloxy, 2,2-dimethylbutyloxy, 3,3-dimethylbutyloxy, 4,4-dimethylbutyloxy, 2,3-dimethylbutyloxy, 2,4-dimethylbutyloxy, 2-methylpentyloxy, 3-methylpentyloxy, 4-methylpentyloxy, 5-methylpentyloxy, 2,2-dimethylpentyloxy, 3,3-dimethylpentyloxy, 4,4-dimethylpentyloxy, 5,5-dimethylpentyloxy, 2,3-dimethylpentyloxy, 2,4-dimethylpentyloxy, 2,5-dimethylpentyloxy, 3,4-dimethylpentyloxy, 3,5-dimethylpentyloxy, 4,5-dimethylpentyloxy, 2-methylhexyloxy, 3-methylhexyloxy, 4-methylhexyloxy, 5-methylhexyloxy, 6-methylhexyloxy, 2,2-dimethylhexyloxy, 3,3-dimethylhexyloxy, 4,4-dimethylhexyloxy, 5,5-dimethylhexyloxy, 6,6-dimethylhexyloxy, 2,3-dimethylhexyloxy, 2,4-dimethylhexyloxy, 2,5-dimethylhexyloxy, 2,6-dimethylhexyloxy, 3,4-dimethylhexyloxy, 3,5-dimethylhexyloxy, 3,6-dimethylhexyloxy, 4,5-dimethylhexyloxy and 5,6-dimethylhexyloxy groups; $C_6$–$C_{16}$ substituted or non-substituted phenyl group bound through $C_0$–$C_6$ methylene chain, such as phenyl, benzyl, phenylethyl, phenylpropyl, phenylbutyl, phenylpentyl, phenylhexyl, 2-methylphenyl, 2-methylbenzyl, 2-(2-methylphenyl)ethyl, 3-(2-methylphenyl)propyl, 4-(2-methylphenyl)butyl, 5-(2-methylphenyl)pentyl, 6-(2-methylphenyl)hexyl, 3-methylphenyl, 3-methylbenzyl, 2-(3-methylphenyl)ethyl, 4-(3-methylphenyl)propyl, 4-(3-methylphenyl)butyl, 5-(3-methylphenyl)pentyl, 6-(3-methylphenyl)hexyl, 4-methylphenyl, 4-methylbenzyl, 2-(4-methylphenyl)ethyl, 3-(4-methylphenyl)propyl, 4-(4-methylphenyl)butyl, 5-(4-methylphenyl)pentyl, 6-(4-methylphenyl)hexyl, 2-propylphenyl, 2-propylbenzyl, 2-(2-propylphenyl)ethyl, 3-(2-propylphenyl)propyl, 4-(2-propylphenyl)butyl, 5-(2-propylphenyl)pentyl, 6-(2-propylphenyl)hexyl, 3-propylphenyl, 3-propylbenzyl, 2-(3-propylphenyl)ethyl, 3-(3-propylphenyl)propyl, 4-(3-propylphenyl)butyl, 5-(3-propylphenyl)pentyl, 6-(3-propylphenyl)hexyl, 4-propylphenyl, 4-propylbenzyl, 2-(4-propylphenyl)ethyl, 3-(4-propylphenyl)propyl, 4-(4-propylphenyl)butyl, 5-(4-propylphenyl)pentyl, 6-(4-propylphenyl)hexyl, 2-cyclopentylphenyl, 2-cyclopentylbenzyl, 2-(2-cyclopentylphenyl)ethyl, 3-(2-cyclopentylphenyl)propyl, 4-(2-cyclopentylphenyl)butyl, 5-(2-cyclopentylphenyl)pentyl, 6-(2-cyclopentylphenyl)hexyl, 3-cyclopentylphenyl, 3-cyclopentylbenzyl, 2-(3-cyclopentylphenyl)ethyl, 3-(3-cyclopentylphenyl)propyl, 4-(3-cyclopentylphenyl)butyl, 5-(3-cyclopentylphenyl)pentyl, 6-(3-cyclopentylphenyl)hexyl, 4-cyclopentylphenyl, 4-cyclopentylbenzyl, 2-(4-cyclopentylphenyl)ethyl, 3-(4-cyclopentylphenyl)propyl, 4-(4-cyclopentylphenyl)butyl, 5-(4-cyclopentylphenyl)pentyl, 6-(4-cyclopentylphenyl)hexyl, 2-cyclohexylphenyl, 2-cyclohexylbenzyl, 2-(4-cyclohexylphenyl)ethyl, 3-(2-cyclohexylphenyl)propyl, 4-(2-cyclohexylphenyl)butyl, 5-(2-cyclohexylphenyl)pentyl, 6-(2-cyclohexylphenyl)hexyl, 3-cyclohexyl(phenyl, 3-cyclohexylbenzyl, 2-(3-cyclohexylphenyl)ethyl, 3-(3-cyclohexylphenyl)propyl, 4-(3-cyclohexylphenyl)butyl, 5-(3-cyclohexylphenyl)pentyl, 6-(3-cyclohexylphenyl)hexyl, 4-cyclohexylphenyl, 4-cyclohexylbenzyl, 2-(4-cyclohexylphenyl)ethyl, 3-(4-cyclohexylphenyl)propyl, 4-(4-cyclohexylphenyl)butyl, 5-(4-cyclohexylphenyl)pentyl, 6-(4-cyclohexylphenyl)hexyl, 2-phenyl-phenyl, 2-phenyl-benzyl, 2-(2-phenyl-phenyl)ethyl, 3-(2-phenyl-phenyl)propyl, 4-(2-phenyl-phenyl)butyl, 5-(2-phenyl-phenyl)pentyl, 6-(2-phenyl-phenyl)hexyl, 3-phenyl-phenyl, 3-phenyl-benzyl, 2-(3-phenyl-phenyl)ethyl, 3-(3-phenyl-phenyl)propyl, 4-(3-phenyl-phenyl)butyl, 5-(3-phenyl-phenyl)pentyl, 6-(3-phenyl-phenyl)hexyl, 4-phenyl-phenyl, 4-phenyl-benzyl, 2-(4-phenyl-phenyl)ethyl, 3-(4-phenyl-phenyl)propyl, 4-(4-phenyl-phenyl)butyl, 5-(4-phenyl-phenyl)pentyl, 6-(4-phenyl-phenyl)hexyl, 2-phenoxy-phenyl, 2-phenoxy-benzyl, 2-(2-phenoxy-phenyl)ethyl, 3-(2-phenoxy-phenyl)propyl, 4-(2-phenoxy-phenyl)butyl, 5-(2-phenoxy-phenyl)pentyl, 6-(2-phenoxy-phenyl)hexyl, 3-phenoxy-phenyl, 3-phenoxy-benzyl, 2-(3-phenoxy-phenyl)ethyl, 3-(3-phenoxy-phenyl)propyl, 4-(3-phenoxy-phenyl)butyl, 5-(3-phenoxy-phenyl)pentyl, 6-(3-phenoxy-phenyl)hexyl, 4-phenoxy-phenyl, 4-phenoxy-benzyl, 2-(4-phenoxy-phenyl)ethyl, 3-(4-phenoxy-phenyl)propyl, 4-(4- phenoxy-phenyl)butyl, 5-(4-phenoxy-phenyl)pentyl and 6-(4-phenoxy-phenyl)hexyl groups; $C_{10}$–$C_{16}$ substituted or non-substituted naphthyl group bound through $C_0$–$C_6$ methylene chain, such as naphthyl, naphthylmethyl, naphthylethyl, naphthylpropyl, naphthylbutyl, naphthylpentyl, naphthylhexyl, 2-methylnaphthyl, 2-methylnaphthylmethyl, 2-(2-methylnaphthyl)ethyl, 3-(2-methylnaphthyl)propyl, 4-(2-methylnaphthyl)butyl, 5-(2-methylnaphthyl)pentyl, 6-(2-methylnaphthyl)hexyl, 3-methylnaphthyl, 3-methylnaphthylmethyl, 2-(3-methylnaphthyl)ethyl, 3-(3-methylnaphthyl)propyl, 4-(3-methylnaphthyl)butyl, 5-(3-methylnaphthyl)pentyl, 6-(3-methylnaphthyl)hexyl, 4-methylnaphthyl, 4-methylnaphthylmethyl, 2-(4-methylnaphthyl)ethyl, 3-(4-methylnaphthyl)propyl, 4-(4-methylnaphthyl)butyl, 5-(4-methylnaphthyl)pentyl, 6-(4-methylnaphthyl)hexyl, 2-propylnaphthyl, 2-propylnaphthylmethyl, 2-(2-propylnaphthyl)ethyl, 3-(2-propylnaphthyl)propyl, 4-(2-propylnaphthyl)butyl, 5-(2-propylnaphthyl)pentyl, 6-(2-propylnaphthyl)hexyl, 3-propylnaphthyl, 3-propylnaphthylmethyl, 2-(3-propylnaphthyl)ethyl, 3-(3-propylnaphthyl)propyl, 4-(3-propylnaphthyl)butyl, 5-(3-propylnaphthyl)pentyl, 6-(3-propylnaphthyl)hexyl, 4-propylnaphthyl, 4-propylnaphthylmethyl, 2-(4-propylnaphthyl)ethyl, 3-(4-propylnaphthyl)propyl, 4-(4-propylnaphthyl)butyl, 5-(4-propylnaphthyl)pentyl, 6-(4-propylnaphthyl)hexyl, 2-cyclopentylnaphthyl, 2-cyclopentylnaphthylmethyl, 2-(2-cyclopentylnaphthyl)ethyl, 3-(2-cyclopentylnaphthyl)propyl, 4-(2-cyclopentylnaphthyl)butyl, 5-(2-cyclopentylnaphthyl)pentyl, 6-(2-cyclopentylnaphthyl)hexyl, 3-cyclopentylnaphthyl, 3-cyclopentylnaphthylmethyl, 2-(3-cyclopentylnaphthyl)ethyl, 3-(3-cyclopentylnaphthyl)propyl, 4-(3-cyclopentylnaphthyl)butyl, 5-(3-cyclopentylnaphthyl)pentyl, 6-(3-cyclopentylnaphthyl)hexyl, 4-cyclopentylnaphthyl, 4-cyclopentylnaphthylmethyl, 2-(4-cyclopentylnaphthyl)ethyl, 3-(4-cyclopentylnaphthyl)propyl, 4-(4-cyclopentylnaphthyl)butyl, 5-(4-cyclopentylnaphthyl)pentyl, 6-(4-cyclopentylnaphthyl)hexyl, 2-cyclohexylnaphthyl, 2-cyclohexylnaphthylmethyl, 2-(2-cyclohexylnaphthyl)ethyl, 3-(2-cyclohexylnaphthyl)propyl, 4-(2-cyclohexylnaphthyl)butyl, 5-(2-cyclohexylnaphthyl)pentyl, 6-(2-cyclohexylnaphthyl)hexyl, 3-cyclohexylnaphthyl, 3-cyclohexylnaphthylmethyl, 2-(3-cyclohexylnaphthyl)ethyl, 3-(3-cyclohexylnaphthyl)propyl, 4-(3-cyclohexylnaphthyl)butyl, 5-(3-cyclohexylnaphthyl)pentyl, 6-(3-cyclohexylnaphthyl)hexyl, 4-cyclohexylnaphthyl, 4-cyclohexylnaphthylmethyl, 2-(4-cyclohexylnaphthyl)ethyl, 3-(4-cyclohexylnaphthyl)propyl, 4-(4-cyclohexylnaphthyl)butyl, 5-(4-cyclohexylnaphthyl)pentyl, 6-(4-cyclohexylnaphthyl)hexyl, 2-phenyl-naphthyl, 2-phenyl-naphthylmethyl, 2-(2-phenyl-naphthyl)ethyl, 3-(2-phenyl-naphthyl)propyl, 4-(2-phenyl-naphthyl)butyl, 5-(2-phenyl-naphthyl)pentyl, 6-(2-phenyl-naphthyl)hexyl, 3-phenyl-naphthyl, 3-phenylnaphthylmethyl, 2-(3-phenyl-naphthyl)ethyl, 3-(3-phenyl-naphthyl)propyl, 4-(3-phenyl-naphthyl)butyl, 5-(3-phenyl-naphthyl)pentyl, 6-(3-phenyl-naphthyl)hexyl, 4-phenyl-naphthyl, 4-phenyl-naphthylmethyl, 2-(4-phenyl-naphthyl)ethyl, 3-(4-phenyl-naphthyl)propyl, 4-(4-phenyl-naphthyl)butyl, 5-(4-phenyl-naphthyl)pentyl, 6-(4-phenyl-naphthyl)hexyl, 2-phenoxy-naphthyl, 2-phenoxy-naphthylmethyl, 2-(2-phenoxy-naphthyl)ethyl, 3-(2-phenoxy-naphthyl)propyl, 4-(2-phenoxy-naphthyl)butyl, 5-(2-phenoxy-naphthyl)pentyl, 6-(2-phenoxy-naphthyl)hexyl, 3-phenoxy-naphthyl, 3-phenoxy-naphthylmethyl, 2-(3-phenoxy-naphthyl)ethyl, 3-(3-phenoxy-naphthyl)propyl, 4-(3-phenoxy-naphthyl)butyl, 5-(3-phenoxy-naphthyl)pentyl, 6-(3-phenoxy-naphthyl)hexyl, 4-phenoxy-naphthyl, 4-phenoxy-naphthylmethyl, 2-(4-phenoxy-naphthyl)ethyl, 3-(4-phenoxy-naphthyl)propyl, 4-(4-phenoxy-naphthyl)butyl, 5-(4-phenoxy-naphthyl)pentyl and 6-(4-phenoxy-naphthyl)hexyl groups; or $C_6$–$C_{16}$ substituted or non-substituted cycloalkyl group bound through $C_0$–$C_6$ methylene chain, such as cyclohexyl, cyclohexylmethyl, cyclohexylethyl, cyclohexylpropyl, cyclohexylbutyl, 2-methylcyclohexyl, 2-methylcyclohexylmethyl, 2-methylcyclohexylethyl, 2-methylcyclohexylpropyl, 2,2-dimethylcyclohexyl, 2,2-dimethylcyclohexylmethyl, 2-(2,2-dimethylcyclohexyl)ethyl, 2,3-dimethylcyclohexyl, 2,3-dimethylcyclohexylmethyl, 2-(2,3-dimethylcyclohexyl)ethyl, 3,3-dimethylcyclohexyl, 3,3-dimethylcyclohexylmethyl, 2-(3,3-dimethylcyclohexyl)ethyl, 2-cyclopentyl-cyclohexyl, 3-cyclopentyl-cyclohexyl, 4-cyclopentyl-cyclohexyl, 2-cyclohexyl-cyclohexyl, 3-cyclohexyl-cyclohexyl, 4-cyclohexyl-cyclohexyl, 2-phenyl-cyclohexyl, 3-phenyl-cyclohexyl, 4-phenyl-cyclohexyl, 2-phenoxy-cyclohexyl, 3-phenoxy-cyclohexyl, 4-phenoxy-cyclohexyl, 2-benzylcyclohexyl, 3-benzyl-cyclohexyl, 4-benzyl-cyclohexyl, 2-benzyloxy-cyclohexyl, 3-benzyloxy-cyclohexyl, 4-benzyloxy-cyclohexyl, 2-naphthyl-cyclohexyl, 3-naphthyl-cyclohexyl, 4-naphthyl-cyclohexyl, 4-naphthyl-cyclohexylmethyl, 2-(4-naphthyl-cyclohexyl)ethyl, 3-(4-naphthyl-cyclohexyl)propyl, 4-(4-naphthyl-cyclohexyl)butyl, 5-(4-naphthyl-cyclohexyl)pentyl, and 6-(4-naphthyl-cyclohexyl)hexyl groups.

In cases where V is nitrogen atom, W is carbon atom and the bond between V and W is double bond, both $R_4$ and $R_5$ do not exist. In cases where V is carbon atom, W is nitrogen. atom or carbon atom, and the bond between V and W is single bond, $R_4$ and $R_5$ cooperatively represent carbonyl group.

The substituent(s) in the above-mentioned substituted phenyl group, substituted naphthyl group and substituted cycloalkyl group is(are) 1 to 5 $C_1$–$C_6$ straight alkyl group(s), $C_3$–$C_6$ branched alkyl group(s), phenyl group(s), phenoxy group(s), cyclopentyl group(s) or cyclohexyl group(s).

In the definition of each substituent, the expression that a group "does not exist" or "no group" means that the group is "not shown in the structural formula", and includes both cases where the atom(s) does(do) not actually exist or hydrogen atom(s) exist(s). For example, in Formula I, in cases where $Z_1$ does not exist, it means that $Z_1$ bound to Y is not shown in the structural formula, so that it means that one or two hydrogen atoms are bound to Y. Similarly, for example, in Formula I, in cases where V and W are bound through double bond, $R_4$ does not exist and hydrogen atom also does not exist. What is meant by this expression can be easily and clearly understood based on ordinary chemical knowledge.

Specific examples of the compounds according to the present invention include the following compounds:

2,4,5,7-tetraaza-7-(3-(4-indole-3-ylpiperidyl)propyl)-3-methyltricyclo[7.4.0.0<2,6>]trideca-1(13),3,5,9(10), 11-pentaene-8-one, 2,4,5,7-tetraaza-7-(3-(3-indole-3-ylpiperidyl)propyl)-3-methyltricyclo[7.4.0.0<2,6>]trideca-1(13),3,5,9(10), 11-pentaene-8-one, 2,4,5,7-tetraaza-7-(2-(4-indole-3-ylpiperidyl)ethyl)3-methyltricyclo[7.4.0.0<2,6>]trideca-1(13),3,5,9(10), 11-pentaene-8-one, 2,4,5,7-tetraaza-11,13-dichloro-7-(3-(4-indole-2-ylpiperidyl)propyl)-3-methyltricyclo[7.4.0.0<2,6>]trideca-1(13),3,5,9(10),11-pentaene-8-one, 2,4,5,7-tetraaza-11,13-difluoro-7-(3-(4-indole-2-ylpiperidyl)propyl)-3-methyltricyclo[7.4.0.0<2,6>]trideca-1(13),3,5,9(10),11-pentaene-8-one, 2,4,5,7-tetraaza-11,13-dihydroxy-7-(3-(4-indole-2-ylpiperidyl)propyl)-3-methyltricyclo[7.4.0.0<2,6>]trideca-1(13),3,5,9(10),11-pentaene-8-one, 2,4,5,7-tetraaza-11-(trifluoromethyl)-7-(3-(4-indole-2-ylpiperidyl)propyl)-3,13-methyltricyclo[7.4.0.0<2,6>]trideca-1(13),3,5,9(10),11-pentaene-8-one, 2,4,5,7-tetraaza-11,13-dichloro-7-(3-(4-indole-2-ylpiperidyl)propyl)-3-methyltricyclo[7.4.0.0<2,6>]trideca-1(13),3,5,9(10),11-pentaene-8-one, 11-amino-2,4,5,7-tetraaza-12-bromo-dichloro-7-(3-(4-indole-2-ylpiperidyl)propyl)-3-methyltricyclo[7.4.0.0<2,6>]trideca-1(13),3,5,9(10),11-pentaene-8-one, 2,4,5,7-tetraaza-7-(3-(4-indole-2-ylpiperidyl)propyl)-3-methyl-11-(methylethyl)tricyclo[7.4.0.0<2,6>]trideca-1(13),3,5,9(10),11-pentaene-8-one, 2,4,5,7-tetraaza-7-(3-(4-indole-2-ylpiperidyl)propyl)-3,13-dimethyl-11-(methylethyl)tricyclo[7.4.0.0<2,6>]trideca-1(13),3,5,9(10),11-pentaene-8-one, 2,4,5,7-tetraaza-7-(3-(4-indole-2-ylpiperidyl)propyl)-3,12-dimethyl-11-methoxytricyclo[7.4.0.0<2,6>]trideca-1(13),3,5,9(10),11-pentaene-8-one, 2,4,5,7-tetraaza-12-bromo-7-(3-(4-indole-2-ylpiperidyl)propyl)-3-methyl-11-methoxytricyclo[7.4.0.0<2,6>]trideca-1(13),3,5,9(10),11-pentaene-8-one, 2,4,5,7-tetraaza-7-(3-(4-indole-2-ylpiperidyl)propyl)-3,11,12-trimethyltricyclo[7.4.0.0<2,6>]trideca-1(13),3,5,9(10),11-pentaene-8-one, 2,4,5,7-tetraaza-7-(3-(4-indole-2-ylpiperidyl)propyl)-3,11-dimethyltricyclo[7.4.0.0<2,6>]trideca-1(13),3,5,9(10),11-pentaene-8-one, 2,4,5,7-tetraaza-7-(3-(4-indole-2-ylpiperidyl)propyl)-3,13-dimethyltricyclo[7.4.0.0<2,6>]trideca-1(13),3,5,9(10),11-pentaene-8-one, 2,4,5,7-tetraaza-12ethyl-7-(3-(4-indole-2-ylpiperidyl)propyl)-3,11-dimethyltricyclo[7.4.0.0<2,6>]trideca-1(13),3,5,9(10),11-pentaene-8-one, 2,4,5,7-tetraaza-7-(3-(4-indole-2-ylpiperidyl)propyl)-11-(dimethylamino)-3,12-dimethyltricyclo[7.4.0.0<2,6>]trideca-1(13),3,5,9(10),11-pentaene-8-one, 2,4,5,7-tetraaza-11-(ethylamino)-7-(3-(4-indole-2-ylpiperidyl)propyl)-3,13-dimethyltricyclo[7.4.0.0<2,6>]trideca-1(13),3,5,9(10),11-pentaene-8-one, 2,4,5,7-tetraaza-7-(3-(4-diphenylmethylene)piperidyl)propyl)-3-trimethyl-11-methoxy-12-nitrotricyclo[7.4.0.0<2,6>]trideca-1(13),3,5,9(10),11-pentaene-8-one, 2,4,5,7-tetraaza-3-methyl-7-(3-(4-diphenylmethoxy)piperidyl)propyl)tricyclo[7.4.0.0<2,6>]trideca-1(13),3,5,9(10),11-pentaene-8-one, 2,4,5,7-tetraaza-3-methyl-7-(3-(4-((2-phenylphenyl)methyl)piperazinyl)propyl)tricyclo[7.4.0.0<2,6>]trideca-1(13),3,5,9(10),11-pentaene-8-one, 2,4,5,7-tetraaza-3-methyl-7-(3-(4-cyclohexyl)piperazinyl)propyl)tricyclo[7.4.0.0<2,6>]trideca-1(13),3,5,9(10),11-pentaene-8-one, 2,4,5,7-tetraaza-3-methyl-7-(3-(4-diphenylmethyl)piperidyl)propyl)tricyclo[7.4.0.0<2,6>]trideca-1(13),3,5,9(10),11-pentaene-8-one, 2,4,5,7-tetraaza-3-methyl-7-(3-(4-((3-phenoxyphenyl)methyl)piperazinyl)propyl)tricyclo[7.4.0.0<2,6>]trideca-1(13),3,5,9(10),11-pentaene-8-one, 2,4,5,7-tetraaza-3-methyl-7-(3-(4-((4-phenoxyphenyl)methyl)piperazinyl)propyl)tricyclo[7.4.0.0<2,6>]trideca-1(13),3,5,9(10),11-pentaene-8-one, 2,4,5,7-tetraaza-3-methyl-7-(3-(3-diphenylmethyl)piperidyl)propyl)tricyclo[7.4.0.0<2,6>]trideca-1(13),3,5,9(10),11-pentaene-8-one, 2,4,5,7-tetraaza-3-methyl-7-(3-(4-diphenylmethyl)piperazinyl)propyl)tricyclo[7.4.0.0<2,6>]trideca-1(13),3,5,9(10),11-pentaene-8-one, 2,4,5,7-tetraaza-3-ethyl-7-(3-(4-diphenylmethyl)piperazinyl)propyl)tricyclo[7.4.0.0<2,6>]trideca-1(13),3,5,9(10),11-pentaene-8-one, 2,4,5,7-tetraaza-3-propyl-7-(3-(4-diphenylmethyl)piperazinyl)propyl)tricyclo[7.4.0.0<2,6>]trideca-1(13),3,5,9(i 0),11-pentaene-8-one, 2,4,5,7-tetraaza-3-methyl-11-methoxy-7-(3-(4-diphenylmethyl)piperazinyl)propyl)tricyclo[7.4.0.0<2,6>]trideca-1(13),3,5,9(10),11-pentaene-8-one, 2,4,5,7-tetraaza-3-methyl-11,12-dimethoxy-7-(3-(4-diphenylmethyl)piperazinyl)propyl)tricyclo[7.4.0.0<2,6>]trideca-1(13),3,5,9(10),11-pentaene-8-one, 2,4,5,7-tetraaza-3-methyl-11-chloro-7-(3-(4-diphenylmethyl)piperazinyl)propyl)tricyclo[7.4.0.0<2,6>]trideca-1(13),3,5,9(10),11-pentaene-8-one, 6-hydroxy-3-(3-(4-(diphenylmethyl)piperazinyl)propyl-2-thioxohydroquinazoline-4-one, 2,4,5,7-tetraaza-3-methyl-11-hydroxy-7-(3-(4-diphenylmethyl)piperazinyl)propyl)tricyclo[7.4.0.0<2,6>]trideca-1(13),3,5,9(10),11-pentaene-8-one, 2,4,5,7-tetraaza-3-methyl-11-isopropoxy-7-(3-(4-diphenylmethyl)piperazinyl)propyl)tricyclo[7.4.0.0<2,6>]trideca-1(13),3,5,9(10),11-pentaene-8-one, 2,4,5,7-tetraaza-3-methyl-12-trifluoromethyl-7-(3-(4-diphenylmethyl)piperazinyl)propyl)tricyclo[7.4.0.0<2,6>]trideca-1(13),3,5,9(10),11-pentaene-8-one, 2,4,5,7-tetraaza-3-methyl-11-dimethylamino-7-(3-(4-diphenylmethyl)piperazinyl)propyl)tricyclo[7.4.0.0<2,6>]trideca-1(13),3,5,9(10),11-pentaene-8-one, 2,4,5,7-tetraaza-3-methyl-7-(2-(4-diphenylmethyl)piperazinyl)ethyl)tricyclo[7.4.0.0<2,6>]trideca-1(13),3,5,9(10),11-pentaene-8-one, 2,4,5,7-tetraaza-3-methyl-7-(4-(4-diphenylmethyl)piperazinyl)butyl)tricyclo[7.4.0.0<2,6>]trideca-1(13),3,5,9(10),11-pentaene-8-one, 2,4,5,7-tetraaza-3-methyl-7-(4-(4-diphenylmethyl)piperidyl)butyl)tricyclo[7.4.0.0<2,6>]trideca-1(13),3,5,9(10),11-pentaene-8-one, 2,4,5,7-tetraaza-3,11,12-trimethyl-7-(3-(4-diphenylmethyl)piperidyl)propyl)tricyclo[7.4.0.0<2,6>]trideca-1(13),3,5,9(10),11-pentaene-8-one, 2,4,5,7-tetraaza-3,11-dimethyl-7-(3-(4-diphenylmethyl)piperidyl)propyl)tricyclo[7.4.0.0<2,6>]trideca-1(13),3,5,9(10),11-pentaene-8-one, 2,4,5,7-tetraaza-3,13-dimethyl-7-(3-(4-diphenylmethyl)piperidyl)propyl)tricyclo[7.4.0.0<2,6>]trideca-1(13),3,5,9(10),11-pentaene-8-one, 2,4,5,7-tetraaza-12-ethyl-3,11-dimethyl-7-(3-(4-diphenylmethyl)piperidyl)propyl)tricyclo[7.4.0.0<2,6>]trideca-1(13),3,5,9(10),11-pentaene-8-one, 2,4,5,7-tetraaza-3-methyl-11-(methylethyl)-7-(3-(4-diphenylmethyl)piperidyl)propyl)tricyclo[7.4.0.0<2,6>]trideca-1(13),3,5,9(10),11-pentaene-8-one, 2,4,5,7-tetraaza-3,13-dimethyl-11-(methylethyl)-7-(3-(4-diphenylmethyl)piperidyl)propyl)tricyclo[7.4.0.0<2,6>]trideca-1(13),3,5,9(10),11-pentaene-8-one, 2,4,5,7-tetraaza-3,12-dimethyl-11-methoxy-7-(3-(4-diphenylmethyl)piperidyl)propyl)tricyclo[7.4.0.0<2,6>]trideca-1(13),3,5,9(10),11-pentaene-8-one, 2,4,5,7-tetraaza-12-bromo-3-methyl-11-methoxy-7-(3-(4-diphenylmethyl)piperidyl)propyl)tricyclo[7.4.0.0<2,6>]trideca-1(13),3,5,9(10),11-pentaene-8-one, 2,4,5,7-tetraaza-11,13-dibromo-3-methyl-7-(3-(4-diphenylmethyl)piperidyl)propyl)tricyclo[7.4.0.0<2,6>]trideca-1(13),3,5,9(10),11-pentaene-8-one, 2,4,5,7-tetraaza-11-(trifluoromethyl)-3,13-dimethyl-7-(3-(4-diphenylmethyl)piperidyl)propyl)tricyclo[7.4.0.0<2,6>]trideca-1(13),3,5,9(10),11-pentaene-8-one, 2,4,5,7-tetraaza-3-methyl-11-methoxy-12-nitro-7-(3-(4-diphenylmethyl)piperidyl)propyl)tricyclo[7.4.0.0<2,6>]trideca-1(13),3,5,9(10),11-pentaene-8-one, 11-amino-2,4,5,7-tetraaza-12-bromo-3-methyl-7-(3-(4-diphenylmethyl)piperidyl)propyl)tricyclo[7.4.0.0<2,6>]trideca-1(13),3,5,9(10),11-pentaene-8-one, 2,4,5,7-tetraaza-11,13-difluoro-3-methyl-7-(3-(4-diphenylmethyl)piperidyl)propyl)tricyclo[7.4.0.0<2,6>]trideca-1(13),3,5,9(10),11-pentaene-8-one, 2,4,5,7-tetraaza-11,13-dihydroxy-3-methyl-7-(3-(4-diphenylmethyl)piperidyl)propyl)tricyclo[7.4.0.0<2,6>]trideca-1(13),3,5,9(10),11-pentaene-8-one, 2,4,5,7-tetraaza-11-(dimethylamino)-3,12-dimethyl-7-(3-(4-diphenylmethyl)piperidyl)propyl)tricyclo[7.4.0.0<2,6>]trideca-1(13),3,5,9(10),11-pentaene-8-one, 2,4,5,7-tetraaza-11-(ethylamino)-3,13-dimethyl-7-(3-(4-diphenylmethyl)piperidyl)propyl)tricyclo[7.4.0.0<2,6>]trideca-1(13),3,5,9(10),11-pentaene-8-one, 2,4,5-triaza-3-methyl-7-(3-(4-diphenylmethyl)piperazinyl)propyl)tricyclo[7.4.0.0<2,6>]trideca-1(13),3,5,7,9(10),11-hexaene, 2,4,5-triaza-3-methyl-8-benzyl-7-(3-(4-diphenylmethyl)piperidyl)propyl)tricyclo[7.4.0.0<2,6>]trideca-1(9),3,5,7,10,12-hexaene, 2,4,5-triaza-3-methyl-8-(2-phenylethyl)-7-(3-(4-diphenylmethyl)piperidyl)propyl)tricyclo[7.4.0.0<2,6>]trideca-1(9),3,5,7,10,12-hexaene, 2,4,5-triaza-3,8,11-trimethyl-7-(3-(4-diphenylmethyl)piperidyl)propyl)tricyclo[7.4.0.0<2,6>]trideca-1(9),3,5,7,10,12-hexaene, 2,4,5-triaza-3,8,11,12-tetramethyl-7-(3-(4-diphenylmethyl)piperidyl)propyl)tricyclo[7.4.0.0<2,6>]trideca-1(9),3,5,7,10,12-hexaene, 2,4,5-triaza-11-ethyl-3,8-dimethyl-7-(3-(4-diphenylmethyl)piperidyl)propyl)tricyclo[7.4.0.0<2,6>]trideca-1(9),3,5,7,10,12-hexaene, 2,4,5-triaza-3,8-dimethyl-1-(methylethyl)-7-(3-(4-diphenylmethyl)piperidyl)propyl)tricyclo[7.4.0.0<2,6>]trideca-1(9),3,5,7,10,12-hexaene, 2,4,5-triaza-3,8-dimethyl-11-methoxy-7-(3-(4-diphenylmethyl)piperidyl)propyl)tricyclo[7.4.0.0<2,6>]trideca-1(9),3,5,7,10,12-hexaene, 2,4,5-triaza-12-bromo-3,8-dimethyl-11-methoxy-7-(3-(4-diphenylmethyl)piperidyl)propyl)tricyclo[7.4.0.0<2,6>]trideca-1(9),3,5,7,10,12-hexaene, 2,4,5-triaza-11,13-dichloro-3,8-dimethyl-7-(3-(4-diphenylmethyl)piperidyl)propyl)tricyclo[7.4.0.0<2,6>]trideca-1(9),3,5,7, 10,12-hexaene, 2,4,5-triaza-11,13-difluoro-3,8-dimethyl-7-(3-(4-diphenylmethyl)piperidinyl)propyl)tricyclo[7.4.0.0<2,6>]trideca-1(9),3,5,7, 10,12-hexaene, 2,4,5-triaza-11-(trifluoromethyl)-3,8-dimethyl-7-(3-(4-diphenylmethyl)piperidyl)propyl)tricyclo[7.4.0.0<2,6>]trideca-1(9),3,5,7,10,12-hexaene, 2,4,5-triaza-3,8-dimethyl-11-methoxy-12-nitro-7-(3-(4-diphenylmethyl)piperidyl)propyl)tricyclo[7.4.0.0<2,6>]trideca-1(9),3,5,7,10,12-hexaene, 2,4,5-triaza-12-bromo-3,8-dimethyl-7-(3-(4-diphenylmethyl)piperidyl)propyl)tricyclo[7.4.0.0<2,6>]trideca-1(9),3,5,7,10,12-hexaene-11-ylamine, 2,4,5-triaza-3,8-dimethyl-7-(3-(4-diphenylmethyl)piperidyl)propyl)tricyclo[7.4.0.0<2,6>]trideca-1(9),3,5,7,10,12-hexaene-11,13-diol, 2,4,5-triaza-3,8,12-trimethyl-7-(3-(4-diphenylmethyl)piperidyl)propyl)tricyclo[7.4.0.0<2,6>]trideca-1(9),3,5,7,10,12-hexaene-11-yl)dimethylamine, (2,4,5-triaza-3,8,12-trimethyl-7-(3-(4-diphenylmethyl)piperidyl)propyl)tricyclo[7.4.0.0<2,6>]trideca-1(9),3,5,7,10,12-hexaene-11-yl)ethylamine, 2,4,5-triaza-11-(dimethylamino)-3,8-dimethyl-7-(3-(4-diphenylmethyl)piperidyl)propyl)tricyclo[7.4.0.0<2,6>]trideca-1(9),3,5,7,10,12-hexaene-13-ol, (2,4,5-triaza-12-chloro-3,8-dimethyl-7-(3-(4-diphenylmethyl)piperidyl)propyl)tricyclo[7.4.0.0<2,6>]trideca-1(9),3,5,7,10,12-hexaene-11-yl)dimethylamine, 2,4,5,7-tetraaza-3-phenyl-7-(3-(4-diphenylmethyl)piperazyl)propyl)tricyclo[7.4.0.0<2,6>]trideca-1(9),3,5,7,10,12-pentaene-8-one, 2,4,5,7-tetraaza-3-propyl-11-methoxy-7-(3-(4-diphenylmethyl)piperazinyl)propyl)tricyclo[7.4.0.0<2,6>]trideca-1(13),3,5,9(10),11-pentaene-8-one, 2,4,5,8-tetraaza-7-(3-(4-diphenylmethyl)piperidyl)propyl)tricyclo[7.4.0.0<2,6>]trideca-1(9),3,5,7,10,12-hexaene, 2,4,5,7-tetraaza-3-methyl-7-(2-((4-diphenylmethyl)piperidyl)methyl)phenyl)tricyclo[7.4.0.0<2,6>]trideca-1(9),3,5,7,10,12-pentaene-8-one, 2,4,5,7-tetraaza-3-methyl-7-(3-(4-diphenylmethyl)piperidyl)phenyl)tricyclo[7.4.0.0<2,6>]trideca-1(9),3,5,7,10,12-pentaene-8-one, 2,4,5,7-tetraaza-7-(1-ethyl-3-(4-diphenylmethyl)piperazinyl)propyl)-3-methyl tricyclo[7.4.0.0<2,6>]trideca-1(9),3,5,7,10,12-pentaene-8-one, 2,4,5,7-tetraaza-7-(3-(4-(3,4-dichlorobenzyl)piperazine-1-yl)propyl)-3-methyl tricyclo[7.4.0.0<2,6>]trideca-1(13),3,5,9(10),11-pentaene-8-one, 2,4,5-triaza-3,5-dimethyl-8-phenyl-7-(3-(4-diphenylmethyl)piperidyl)propyl)tricyclo[7.4.0.0<2,6>]trideca-1,3,7,10,12-pentaene, and 2,4,5-triaza-3,8-dimethyl-7-(3-(4-diphenylmethyl)piperidyl)propyl)tricyclo[7.4.0.0<2,6>]trideca-1(9),3,5,7,10,12-hexaene.

Processes for producing the compounds represented by Formula I ("the compounds represented by Formula I", for example, will also be hereinafter referred to as simply "Formula I") will now be described, but the process for producing each compound is not restricted thereto. Further, in the various production processes, the reaction conditions may be appropriately selected from those described in the following.

Among the compounds represented by Formula I, those wherein V is carbon atom and the bond between W and V is single bond, and $R_4$ and $R_5$ cooperatively form carbonyl group, which are represented by Formula IV:

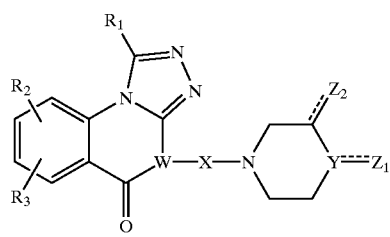

(wherein W, X, Y, $Z_1$, $Z_2$, $R_1$, $R_2$ and $R_3$ represent the same meanings as mentioned above)

may be produced by reacting Formula VI:

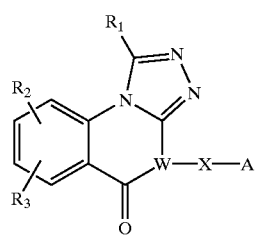

(wherein A represents chloro, bromo, mesyl or tosyl group, W, X, $R_1$, $R_2$ and $R_3$ represent the same meanings as mentioned above)

and Formula VII:

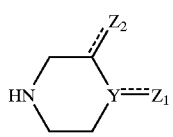

(wherein Y, $Z_1$ and $Z_2$ represent the same meanings as mentioned above); or may be produced by reacting Formula VIII:

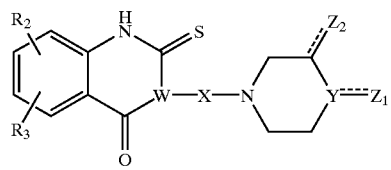

(wherein W, X, Y, $Z_1$, $Z_2$, $R_2$ and $R_3$ represent the same meanings as mentioned above)

with hydrazine and then with $R_1C(OR_9)_3$ (wherein $R_1$ represents the same meanings as mentioned above and $R_9$ represents methyl, ethyl or propyl group).

Among the compounds represented by Formula VI, those wherein W is nitrogen atom, which are represented by Formula XIII, may be produced by the steps shown in the following. In the present specification, "step" is indicated as "step" in chemical reaction formulae.

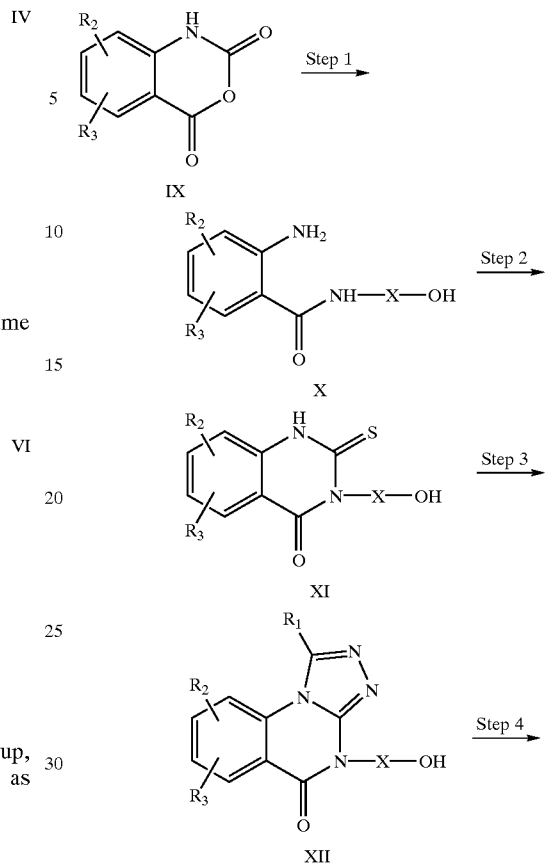

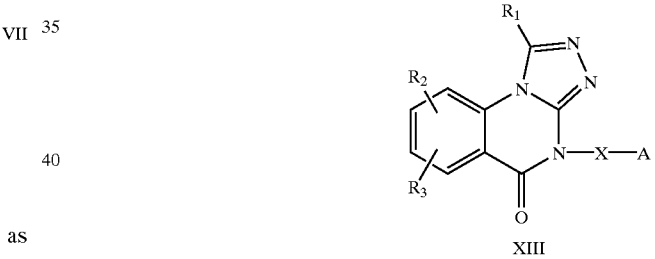

(wherein X, $R_1$, $R_2$, $R_3$ and A represent the same meanings as mentioned above).

Step 1 is the step in which an isatoic anhydride IX is reacted with NH—X—OH (wherein X represents the same meanings as mentioned above). This step may be carried out at 0° C. to 50° C., and sufficient reaction rate may be attained at room temperature. As the reaction solvent, an ether solvent such as tetrahydrofuran or dimethoxy ethane may usually be employed, but other solvents may also be employed. Although the reaction time may appropriately be selected depending on the reaction temperature and the like, it may usually be 1 to 24 hours.

Step 2 is the reaction for obtaining XI by reacting X with an excess amount of carbon disulfide in an alcoholic solvent such as methanol or ethanol. Usually, 2 to 4 equivalents of carbon disulfide is used, but more equivalents of carbon disulfide may be employed. The base used in this step may be sodium hydroxide, potassium hydroxide, pyridine, triethylamine or the like, but other bases may also be employed.

The reaction temperature may be 60 to 80° C., but other temperatures may also be employed. Although the reaction time may be appropriately selected depending on the reaction temperature and the like, usually the reaction time may be about 2 to 96 hours.

Step 3 may be carried out by reacting the reaction product with hydrazine hydrate, and then with $R_1C(OR_9)_3$. In cases where $R_1$ in $R_1C(OR_9)_3$ is methyl group, ortho triethyl acetate is usually employed as $R_1C(OR_9)_3$, although $R_1C(OR_9)_3$ is not restricted thereto. In the step of reacting the reaction product with hydrazine, although an alcoholic solvent such as methanol or ethanol is employed, non-polar solvents such as benzene, toluene and xylene, as well as polar solvents such as tetrahydrofuran and dimethylformamide may also be employed. The reaction proceeds also in the absence of a solvent. The reaction temperature may be room temperature to 200° C., and usually about 100° C. The mixing ratio of XI to hydrazine hydrate at the beginning of reaction may usually be about 1:10 to 1:100 by mole. Although the reaction time may appropriately be selected depending on the reaction temperature and the like, it may usually be 2 to 96 hours.

The next reaction wherein $R_1C(OR_9)_3$ is used is carried out in an alcoholic solvent such as methanol or ethanol, or in the absence of solvent. The reaction may be carried out at 60° C. to 150° C., and preferably at 100° C. to 120° C. Although the mixing ratio of the reaction product of Step 1 to $R_1C(OR_9)_3$ at the beginning of this second step is not restricted, usually about 1:2 to 1:30 by mole is preferred. Although the reaction time may appropriately be selected depending on the reaction temperature and the like, it may usually be about 1 to 8 hours.

Step 4 is the step for converting the hydroxyl group to chloro, bromo, tosyl or mesyl group. To convert the hydroxyl group to chloro, a chlorination reagent such as thionyl chloride, concentrated hydrochloric acid or carbon tetrachloride-triphenylphosphine may be employed, but other chlorination reagents may also be employed. To convert the hydroxyl group to bromo, a bromination reagent such as thionyl bromide, hydrobromic acid, carbon tetrabromide-triphenylphosphine may be employed, but other bromination reagents may also be employed. Conversion of the hydroxyl group to tosyl or mesyl group may be attained by reacting the reaction product with methanesulfonyl chloride or p-toluenesulfonyl chloride, respectively, in the presence of a base such as pyridine or triethylamine. The reaction may usually be carried out at −20° C. to room temperature, and preferably be carried out under cooling in ice. As the solvent, although a halogen-containing solvent such as methylene chloride or chloroform is employed, pyridine or the like may also be employed. Although the mixing ratio of XII in the reaction mixture to the chlorination reagent, bromination reagent, sulfonyl chloride or the like at the beginning of the reaction is not restricted, it may usually be 1:1 to 1:5 by mole. Although the reaction time may appropriately be selected depending on the reaction temperature and the like, it may usually be about 1 to 24 hours.

XI may also be produced by the following steps:

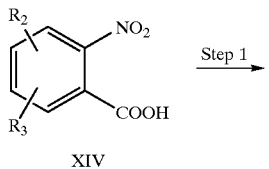

XIV

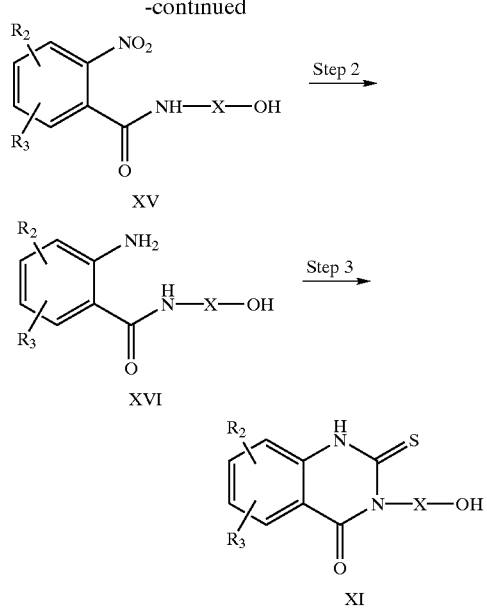

(wherein X, $R_2$ and $R_3$ represent the same meanings as mentioned above).

Step 1 is the step for condensing the o-nitrobenzoic acid derivative with $H_2N$—X—OH (wherein X represents the same meanings as mentioned above). As the condensation reagent, those used for carrying out condensation between amino acids, such as DCC, BOP and PyBOP may usually be used, but the condensation reagent is not restricted thereto. As the reaction solvent, dimethylformamide, methylene chloride or the like is employed. The reaction may preferably be carried out under cooling in ice to at room temperature, but the reaction may also be carried out at other temperatures. The mixing ratio of XIV, $H_2N$—X—OH and the condensation reagent at the beginning of the reaction is not restricted, but the mixing ratio of about 1:1:1 to 1:3:3 by mole is preferred. Although the reaction time may appropriately be selected depending on the reaction temperature and the like, it may usually be about 3 to 24 hours.

Step 2 is the step for reducing the nitro group to amino group. Usually, a hydrogenation method is employed, but other methods for reduction may also be employed. In case of hydrogenation reaction, usually, in an alcoholic solvent such as methanol or ethanol, a metal catalyst such as palladium/carbon, palladium hydroxide or platinum dioxide is employed, but other metal catalysts may also be employed. Although the reaction time may appropriately be selected depending on the reaction temperature and the like, it may usually be about 2 to 24 hours.

Step 3 is the step for reacting XVI with an excess amount of carbon disulfide in an alcoholic solvent such as methanol or ethanol. The base used in this step may be sodium hydroxide, potassium hydroxide, pyridine, triethylamine or the like. The reaction may be carried out between room temperature and 100° C. and may preferably be carried out at 60° C. to 80° C. The mixing ratio of XVI, carbon disulfide and the base at the beginning of the reaction is not restricted, and usually about 1:3:1 to 1:10:3 by mole is preferred. Although the reaction time may appropriately be selected depending on the reaction temperature and the like, it may usually be about 2 to 96 hours.

Among the compounds represented by Formula VII, those wherein Y is carbon atom, $Z_2$ does not exist, $Z_1$ and Y are bonded through double bond, $Z_1$ is represented by $QCR_6R_7R_8$ wherein Q and $R_6$ do not exist, and both $R_7$ and $R_8$ are phenyl groups, which are represented by Formula XX; and those wherein Y is carbon atom, $Z_2$ does not exist, $Z_1$ and Y are bonded through single bond, $Z_1$ is represented by $QCR_6R_7R_8$ wherein Q does not exist, $R_6$ is hydrogen and both $R_7$ and $R_8$ are phenyl groups, which are represented by Formula XXII, may be produced by the following processes.

of XVIII to the acid at the beginning of the reaction is not restricted, the mixing ratio of about 1:0.1 to 1:10 by mole is usually preferred. The reaction time may usually be about 5 to 24 hours.

Step 3 is the step for removing the protective group on the nitrogen atom. In cases where $R_{11}$ is acetyl group, this step may be carried out by adding aqueous sodium hydroxide

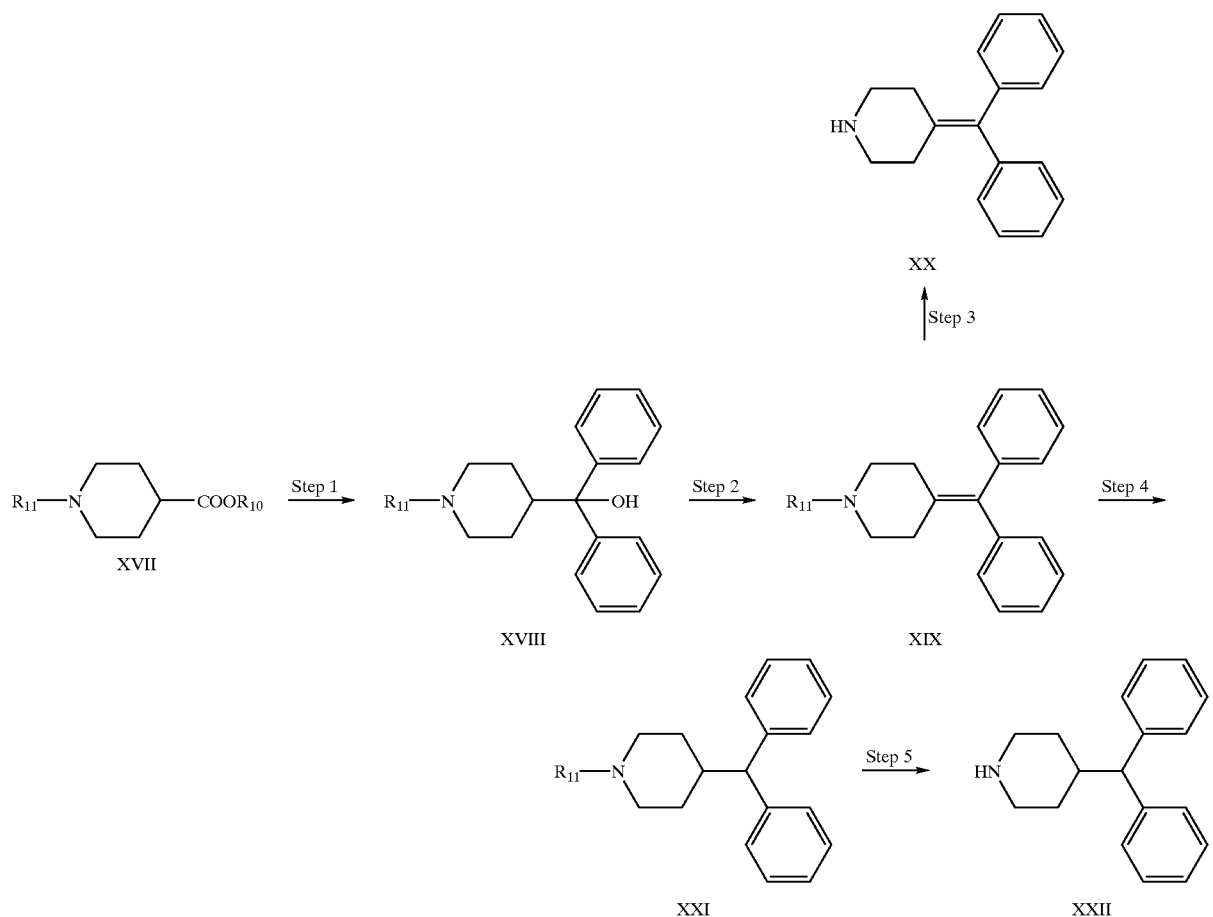

(wherein $R_{10}$ represents methyl or ethyl group, $R_{11}$ represents acetyl, Boc or benzyl group).

Step 1 is the step for reacting XVII with a phenyl metal reagent. As the phenyl metal reagent, a Grignard reagent such as phenyl magnesium bromide; phenyl lithium or the like may be employed, but the phenyl metal reagent is not restricted thereto. The reaction may proceed at −20° C. to 50° C., and may preferably be carried out under cooling in ice to at room temperature. As the reaction solvent, an ether solvent such as tetrahydrofuran or dimethoxyethane may usually be employed. Although the mixing ratio of XVII to the phenyl metal reagent at the beginning of the reaction is not restricted, the mixing ratio of about 1:2 to 1:4 by mole is usually preferred. Although the reaction time may appropriately be selected depending on the reaction temperature and the like, it may usually be about 2 to 24 hours.

Step 2 may be carried out by heating the reaction mixture to reflux in acetic anhydride, or by treating the reaction mixture with a dilute mineral acid such as dilute hydrochloric acid or dilute sulfuric acid in an alcoholic solvent such as methanol or ethanol. Organic acids such as formic acid and acetic acid may also be employed. Although the mixing ratio solution, aqueous potassium hydroxide solution or the like and heating the resultant to reflux in an alcoholic solvent such as methanol or ethanol. Although the mixing ratio of XIX to the base at the beginning of the reaction is not restricted, the mixing ratio of about 1:1 to 1:5 by mole is usually preferred. The reaction time may usually be about 5 to 20 hours.

In cases where $R_{11}$ is Boc group, this step may be carried out by treating the reaction mixture with an organic acid such as trifluoroacetic acid or with a dilute mineral acid such as dilute hydrochloric acid in a halogen-containing solvent such as chloroform or methylene chloride, thereby obtaining XX. This reaction may be carried out at −20° C. to 50° C., but usually carried out at room temperature. In this case, although the mixing ratio of XIX to the base at the beginning of the reaction is not restricted, the mixing ratio of about 1:0.1 to 1:10 by mole is usually preferred. The reaction time may usually be about 3 to 20 hours.

In cases where $R_{11}$ is benzyl group, the benzyl group may be removed by treating the reaction mixture with sodium or lithium in liquid ammonia. In this case, although the mixing ratio of XIX to the alkaline metal at the beginning of the reaction is not restricted, the mixing ratio of about 1:1 to 1:5 by mole is usually preferred. The reaction time may usually be about 1 to 10 hours.

Step 4 may be carried out by hydrogenation by using a palladium-based catalyst such as palladium/carbon or palladium hydroxide, or a platinum-based catalyst such as platinum dioxide in an alcoholic solvent such as methanol or ethanol, or in a polar solvent such as ethyl acetate, tetrahydrofuran or dioxane. Although the reaction temperature is not restricted, usually about 10° C. to 30° C. is preferred. The reaction time may usually be about 3 to 48 hours. In cases where $R_{11}$ is benzyl group, XXII may be directly obtained by Step 4.

Step 5 may be carried out similarly to Step 3.

Among the compounds represented by Formula VII, those wherein Y is carbon atom, $Z_1$ does not exist, the bond between $Z_2$ and the carbon atom is double bond, $Z_2$ is $QCR_6R_7R_8$ wherein Q and $R_6$ do not exist, both $R_7$ and $R_8$ are phenyl groups, which are represented by Formula XXIII; and those wherein Y is carbon atom, $Z_1$ does not exist, the bond between $Z_2$ and the carbon atom is single bond, $Z_2$ is $QCR_6R_7R_8$ wherein Q does not exist, $R_6$ is hydrogen, and both $R_7$ and $R_8$ are phenyl groups, which are represented by Formula XXI, may be produced in the similar manner to the production process of XX and XXII, using XXV as a starting material.

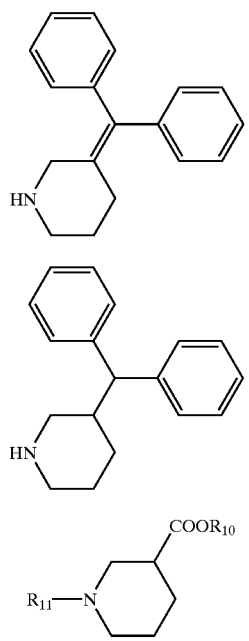

(wherein $R_{10}$ and $R_{11}$ represent the same meanings as mentioned above).

Among the compounds re presented by Formula VII, those wherein Y is carbon atom, $Z_2$ does not exist, the bond between Y and $Z_1$ is single bond, $Z_1$ is $QCR_6R_7R_8$ wherein Q is oxygen atom, $R_6$ is hydrogen, and both $R_7$ and $R_8$ are phenyl groups, which are represented by Formula XXVIII may be produced by the following process.

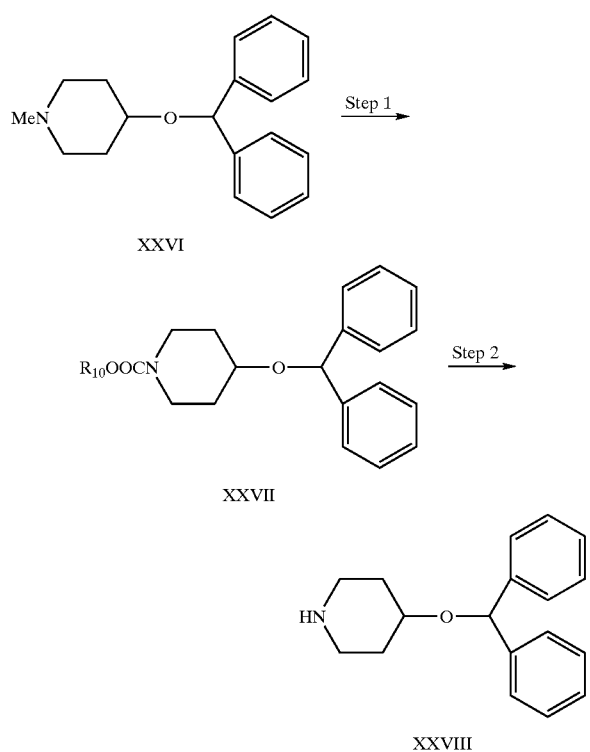

(wherein $R_{10}$ represents the same meanings as mentioned above).

Step 1 is the step for reacting diphenylmethoxy N-methylpiperidine XXVI with an alkyl chloroformate in a non-polar solvent such as benzene or toluene, thereby converting XXVI to XXVII. In this step, sufficient reaction rate may be obtained at 60° C. to 80° C., but the reaction may also be carried out at other temperatures. Although the mixing ratio of XXVI to the alkyl chloroformate at the beginning of the reaction is not restricted, a mixing ratio of about 1:1 to 1:3 by mole is usually preferred. The reaction time may appropriately be selected depending on the reaction temperature or the like, and may usually be about 10 to 24 hours.

Step 2 may be carried out by heating the reaction mixture to reflux under basic condition in an alcoholic solvent such as methanol or ethanol. As the base, aqueous sodium hydroxide solution or potassium hydroxide is preferred, but the base is not restricted to these. Although the mixing ratio of XXVII to the base at the beginning of the reaction is not restricted, a mixing ratio of about 1:2 to 1:5 by mole is usually preferred. The reaction time may usually be about 10 to 40 hours.

Among the compounds represented by Formula VII, those wherein Y is nitrogen atom, $Z_2$ does not exist, the bond between Y and $Z_1$ is single bond, $Z_1$ is $QCR_6R_7R_8$ wherein Q does not exist, $R_6$ is hydrogen, and both $R_6$ and $R_7$ are hydrogen, which are represented by Formula XXXI, may be produced from a piperazine derivative XXIX and a substituted or non-substituted aldehyde.

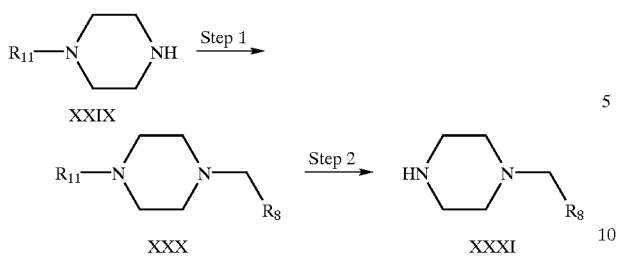

(wherein $R_8$ and $R_{11}$ represent the same meanings as mentioned above).

The condensation between the piperazine derivative XXIX and the substituted or non-substituted aldehyde may be carried out by azeotropic dehydration using Dean-Stark apparatus in a solvent such as benzene or toluene; or by using a Lewis acid such as trifluoroboron. In the latter case, although the reaction temperature is not restricted, usually about −20° C. to 30° C. is preferred. Although the mixing ratio of XXIX to the Lewis acid at the beginning of the reaction is not restricted, a mixing ratio of about 1:0.1 to 1:1 by mole is usually preferred. The reaction time may usually be about 1 to 10 hours. By reducing the reaction product with a reducing agent such as sodium borohydride in an alcoholic solvent such as methanol, XXX is obtained.

Alternatively, by treating a mixture of the piperazine derivative and the substituted or non-substituted aldehyde in an alcoholic solvent such as methanol with a reducing agent such as sodium triacetylboro hydride or sodium cyanoboro hydride, XXX may be obtained. In cases where sodium triacetylboro hydride, sodium cyanoboro hydride or the like is used as the reducing agent, the reaction may preferably be carried out at −20° C. to room temperature, but the reaction may also be carried out at other temperatures. As the acid to be used in the reaction, acetic acid or hydrochloric acid may usually be used, but the acid is not restricted thereto. Although the mixing ratio of the piperazine derivative, substituted or non-substituted aldehyde, the reducing agent and the acid at the beginning of the reaction is not restricted, a mixing ratio of about 1:1:1:1 to 1:1:3:2 by mole is usually preferred.

Step 2 may be carried out in the similar manner to Step 3 in producing XX.

Among the compounds represented by Formula VII, those wherein Y is nitrogen atom, $Z_2$ does not exist, the bond between Y and $Z_1$ is single bond, $Z_1$ is $C_6$–$C_{18}$ substituted or nion-substituted cyclohexyl may be produced in the similar manner to the process described above.

Among the compounds represented by Formula VIII, those wherein W is nitrogen atom, which are represented by Formula XXXIII, may be produced by the following process.

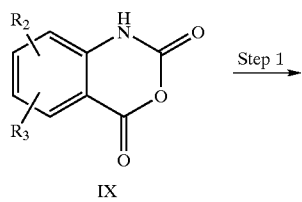

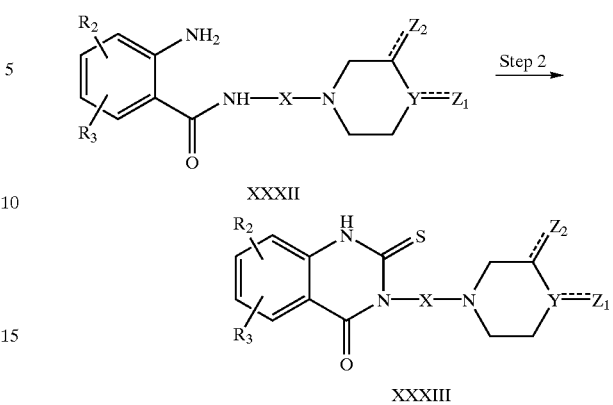

(wherein X, Y, $Z_1$, $Z_2$, $R_2$ and $R_3$ represent the same meanings as mentioned above).

Step 1 is the step for condensing the isatoic anhydride IX with XXXIV represented by the formula below. As the reaction solvent, an ether solvent such as tetrahydrofuran or dimethoxyethane may usually be used, but other solvents may also be used. The reaction may be carried out at 0° C. to 50° C., and sufficient reaction rate may be obtained at room temperature. The mixing ratio of IX to XXXIV at the beginning of the reaction is not restricted, but usually about 1:1 to 1:2 by mole is preferred. The reaction time may be appropriately selected depending on the reaction temperature or the like, and usually about 1 to 24 hours.

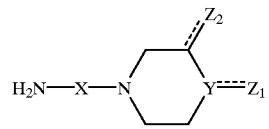

(wherein X, Y, $Z_1$ and $Z_2$ represent the same meanings as mentioned above).

Step 2 is the step for obtaining XXXIII by reacting XXXII with an excess amount of carbon disulfide in an alcoholic solvent such as methanol or ethanol. Carbon disulfide may usually be used in an amount of 2 to 4 equivalents, but more amounts of carbon disulfide may also be used. As the base, sodium hydroxide, potassium hydroxide, pyridine, triethylamine or the like may usually be employed, but other bases may also be employed. Although the mixing ratio of XXXII to the base at the beginning of the reaction is not restricted, usually about 1:1 to 1:3 by mole is preferred. The reaction time may be appropriately selected depending on the reaction temperature and the like, and usually about 2 to 96 hours.

Formula XXXIV may be produced by reacting NC—X—A (wherein A represents the same meanings as mentioned above) with VII in the presence of a base, in a polar solvent such as acetonitrile or dimethylformamide at room temperature to 100° C., preferably at 70° C. to 80° C., and then by reducing the cyano group. As the base, potassium carbonate or the like may usually be used, but other bases may also be used. Although the mixing ratio of NC—X—A, VII and the base at the beginning of the reaction is not restricted, usually about 1:1:1 to 1:2:4 by mole is preferred. The reaction time may be appropriately selected depending on the reaction temperature and the like, and usually about 2 to 48 hours. Reduction of the cyano group may be carried out by using a reducing agent such as lithium aluminum hydride in an ether solvent such as tetrahydrofuran or dimethoxyethane; or by hydrogenation employing a metal catalyst such as palladium/carbon, palladium hydroxide or platinum dioxide; but other reduction conditions may also be employed.

The step for obtaining IV by reacting VI with VII may be carried out as follows. This step may be carried out by heating the reaction mixture in a polar solvent such as dimethylformamide, acetonitrile or dimethylsulfoxide to a temperature between 50° C. and 100° C. Although the mixing ratio of VI to VII at the beginning of the reaction is not restricted, usually about 1:1 to 1:3 by mole is preferred. The reaction time may be appropriately selected depending on the reaction temperature and the like, and usually about 2 to 24 hours.

The step for, reacting Formula VIII with hydrazine, and then with $R_1C(OR_9)_3$ (wherein $R_1$ represent the same meanings as mentioned above and $R_9$ represents methyl, ethyl or propyl group) may be carried out in the similar manner to Step 3 in the production process of XIII.

Among the compounds represented by Formula I, those wherein W and V are carbon atoms, X is n-propyl group, $R_4$ does not exist, $R_5$ is hydrogen, $C_1$–$C_6$ straight alkyl group, $C_3$–$C_8$ branched alkyl group, $C_6$–$C_{22}$ substituted or non-substituted phenyl group, or $C_6$–$C_{22}$ substituted or non-substituted cycloalkyl group, and the bond between W and V is double bond, which are represented by Formula XXXV; and those wherein W and V are carbon atoms, X is n-propyl group, $R_4$ is hydrogen, $R_5$ is hydrogen, $C_1$–$C_6$ straight alkyl group, $C_3$–$C_8$ branched alkyl group, $C_6$–$C_{22}$ substituted or non-substituted phenyl group, or $C_6$–$C_{22}$ substituted or non-substituted cycloalkyl group, and the bond between W and V is single bond, which are represented by Formula XXXVI, may be produced by the following process.

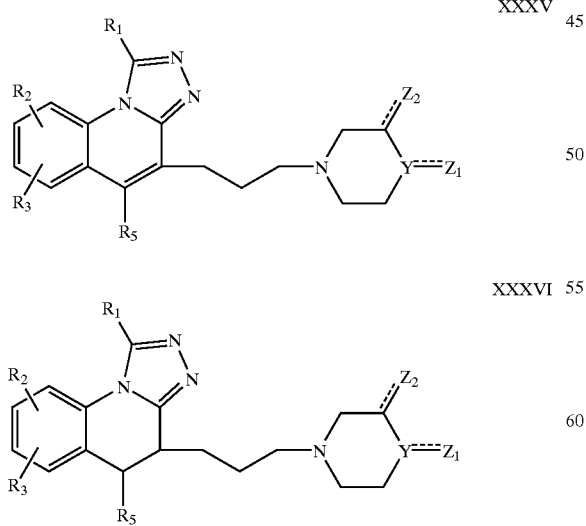

(wherein Y, $Z_1$, $Z_2$, $R_1$, $R_2$, $R_3$ and $R_5$ represent the same meanings as mentioned above)

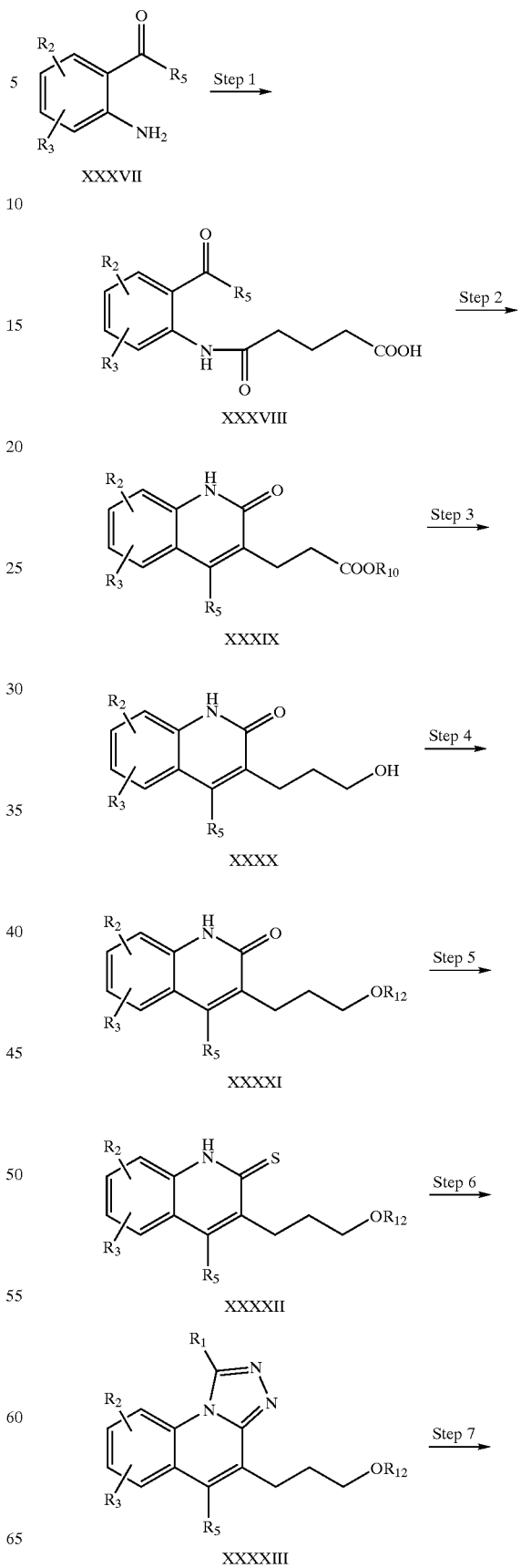

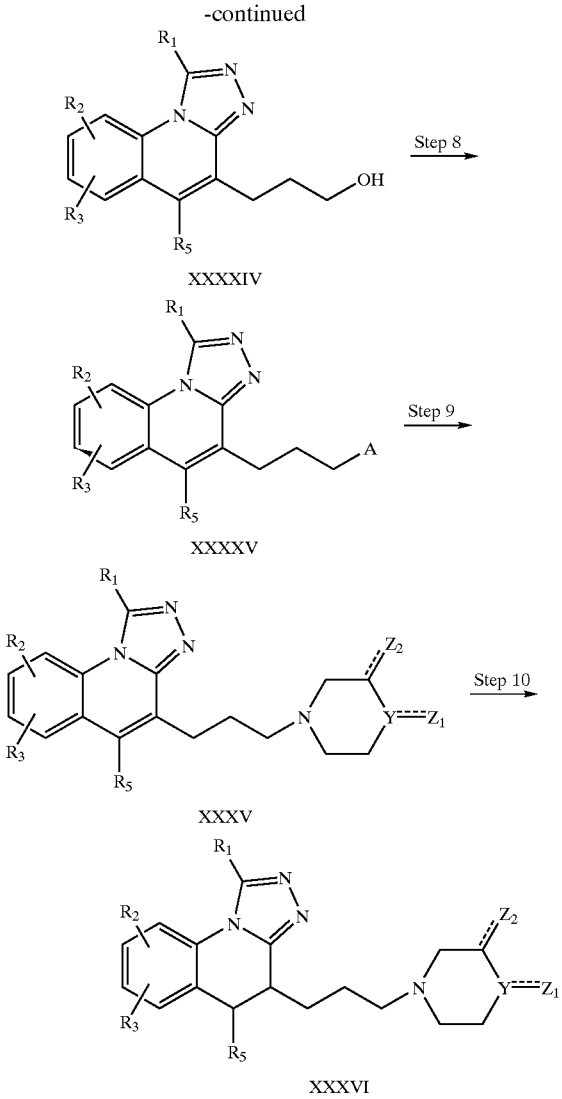

(wherein $R_2$, $R_3$, $R_5$ and $R_{10}$ represent the same meanings as mentioned above and $R_{12}$ represents benzyl, tetrapyranyl, methoxymethyl, t-butyldiphenylsilyl, t-butyldimethylsilyl or triethylsilyl group.)

Step 1 is the step for obtaining XXXVIII by reacting XXXVII with glutaric anhydride in a non polar solvent such as benzene or toluene. The reaction is usually carried out under heating to reflux, but the reaction proceeds at other temperatures. Although the mixing ratio of XXXVII to glutaric anhydride at the beginning of the reaction is not restricted, usually about 1:1 to 1:2 by mole is preferred. The reaction time may usually be about 4 to 12 hours.

Step 2 may be carried out by heating the reaction mixture in aqueous potassium hydroxide solution or aqueous sodium hydroxide solution to reflux to obtain a cyclized compound, and then heating the product to reflux under acidic condition attained by hydrochloric acid, sulfuric acid or the like, in methanol or ethanol. As the base used in the first step, usually aqueous potassium hydroxide solution or aqueous sodium hydroxide solution is used, but other bases such as potassium t-butoxide in an ether solvent such as tetrahydrofuran or dimethoxyethane may also be used. The mixing ratio of XXXVIII to the base at the beginning of the first step of the reaction is not restricted, but usually about 1:1 to 1:5 by mole is preferred. The reaction time may usually be about 4 to 12 hours. The reaction time of the second step may usually be about 3 to 8 hours.

Step 3 is the step for reducing the ester group. As the reducing agent, lithium aluminum hydride, diisobutyl aluminum hydride or the like may be employed, but other reducing agents may also be employed. As the reaction solvent, an ether solvent such as tetrahydrofuran or dimethoxyethane may be used. The reaction temperature is not restricted, but usually about $-10°$ C. to $30°$ C. is appropriate. Although the mixing ratio of XXXIX to the reducing agent is not restricted, usually about 1:1 to 1:3 by mole is appropriate. The reaction time may usually be about 2 to 6 hours.

Step 4 is the step for protecting the alcohol. In cases where $R_{12}$ is t-butyldiphenylsilyl, the step may usually be carried out by reacting the reaction product with t-butyldiphenylsilyl chloride using imidazole as a base in dimethylformamide. In cases where $R_{12}$ is t-butyldimethylsilyl group, usually, t-butyldimethylsilyl chloride is reacted with the reaction product using imidazole, morpholine or the like as a base in a polar solvent such as dimethylformamide or tetrahydrofuran. In cases where $R_{14}$ is trimethylsilyl group, the step may usually be carried out by reacting trimethylsilyl chloride with the reaction product using pyridine as a base in a halogen-containing solvent such as methylene chloride, but other methods may also be employed. In cases where $R_{12}$ is benzyl group, the step may usually be carried out by reacting benzyl bromide with the reaction product using a base such as sodium hydride or potassium t-butoxide in an ether solvent such as tetrahydrofuran or dimethoxyethane, but other methods may also be employed. In cases where $R_{12}$ is tetrahydropyranyl group, the step may be carried out by reacting dihydropyran with the reaction product under acidic condition, in a halogen-containing solvent such as methylene chloride. As the acid, p-toluenesulfonic acid is usually employed, but the acid is not restricted thereto. In cases where $R_{12}$ is methoxymethyl group, the step may be carried out by reacting chloromethylmethyl ether with the reaction product using diisopropylethylamine as a base in a halogen-containing solvent such as methylene chloride, but other methods may also be employed. In these cases, the reaction temperature is not restricted but usually about $0°$ C. to $30°$ C. is appropriate. Although the mixing ratio of XXXX to the base or the acid at the beginning of the reaction is not restricted, usually about 1:1 to 1:3 by mole is appropriate. The reaction time may appropriately be selected depending on the reaction temperature and the like, and usually about 1 to 24 hours.

Step 5 is the step for obtaining XXXXII by reacting XXXXI with an excess amount of diphosphorus pentasulfide or Lawesson's reagent. Diphosphorus pentasulfide or Lawesson's reagent may be used in an amount of 1 to 4 equivalents, but larger amounts may also be employed. In cases where diphosphorus pentasulfide is used, in an ether solvent such as tetrahydrofuran or dimethoxyethane, a base such as pyridine, triethylamine or sodium hydrogen carbonate may be used, but other bases may also be employed. The reaction may be carried out at $50°$ C. to $100°$ C., but the reaction may be carried out at other temperatures. In cases where Lawesson's reagent is used, XXXXII may be obtained at room temperature to $100°$ C. in a non-polar solvent such as toluene or in an ether solvent such as dimethoxyethane. Although the reaction time may be appropriately selected depending on the reaction temperature and the like, in case of using diphosphorus pentasulfide, the reaction time may usually be about 20 to 200 hours, and in case of using Lawesson's reagent, the reaction time may usually be about 2 to 10 hours.

Step 6 may be carried out by reacting the reaction product with hydrazine hydrate and then with $R_1C(OR_9)_3$. In cases where $R_1$ in $R_1C(OR_9)_3$ is methyl group, ortho triethyl acetate is usually used, but not restricted thereto. In this step, in the step of the reaction with hydrazine, an alcoholic solvent such as methanol or ethanol is usually used, but a non-polar solvent such as benzene, toluene or xylene, or a polar solvent such as tetrahydrofuran or dimethylformamide may also be employed. The reaction proceeds also in the absence of a solvent. The reaction temperature may be room temperature to 200° C., and usually about 100° C. Although the mixing ratio of XXXXII to the hydrazine hydrate at the beginning of the reaction is not restricted, usually about 1:10 to 1:100 is appropriate. The reaction time may be appropriately selected depending on the reaction temperature and the like, but the reaction time may usually be about 1 to 8 hours.

Step 7 is the step for removing the protective group of the hydroxyl group. In cases where $R_{12}$ is diphenylmethylsilyl, t-butyldimethylsilyl or trimethylsilyl group, the step may usually be carried out by reacting tetra n-butylammonium fluoride with the reaction product in a polar solvent such as dimethylformamide at room temperature, or by treating the reaction mixture with acetic acid in a mixed solvent such as tetrahydrofuran-water at room temperature to 60° C. Other reaction conditions may also be employed. In the former case, although the mixing ratio of XXXXIII to tetra n-butylammonium fluoride at the beginning of the reaction is not restricted, usually about 1:1 to 1:3 is appropriate. The reaction time may appropriately be selected depending on the reaction temperature and the like, and may usually be about 2 to 12 hours. In the latter case, although the mixing ratio of XXXXIII to acetic acid at the beginning of the reaction is not restricted, usually about 1:0.1 to 1:3 by mole is appropriate. The reaction time may appropriately be selected depending on the reaction temperature and the like, and may usually be about 1 to 10 hours.

In cases where $R_{12}$ is benzyl group, the step may usually. be carried out by hydrogenation by using a palladium-based catalyst such as palladium/carbon or palladium hydroxide, or using a platinum-based catalyst such as platinum dioxide in an alcoholic solvent such as methanol or ethanol, or in a polar solvent such as ethyl acetate, tetrahydrofuran or dioxane, but other methods may also be employed. Although the reaction temperature is not restricted, usually about 10° C. to 30° C. is appropriate. The reaction time may appropriately be selected depending on the reaction temperature and the like, and may usually be about 2 to 12 hours.

In cases where $R_{12}$ is tetrahydropyranyl group, the step may be carried out by treating the reaction mixture with a dilute mineral acid such as dilute hydrochloric acid or dilute sulfuric acid, or with an organic acid such as p-toluenesulfonic acid, in an alcoholic solvent such as methanol or ethanol, or in tetrahydrofuran, dimethoxyethane, dioxane or the like. The reaction may preferably be carried out under cooling in ice to at room temperature, but .the reaction temperature is not restricted thereto. Although the mixing ratio of XXXXIII to the organic acid at the beginning of the reaction is not restricted, usually about 1:0.1 to 1:1 by mole is appropriate. The reaction time may appropriately be selected depending on the reaction temperature and the like, and may usually be about 1 to 10 hours.

In cases where $R_{12}$ is methoxymethyl group, the step may be carried out by adding a dilute mineral acid such as dilute hydrochloric acid or dilute-sulfuric acid, or an organic acid such as p-toluenesulfonic acid and then heating the reaction mixture in a solvent such as methanol. The reaction temperature is not restricted, but usually about 10° C. to 60° C. is appropriate. Although the mixing ratio of XXXXIII to the organic acid at the beginning of the reaction is not restricted, usually about 1:0.1 to 1:10 by mole is appropriate. The reaction time may appropriately be selected depending on the reaction temperature and the like, and may usually be about 1 to 10 hours.

Step 8 is the step for converting the hydroxyl group to chloro, bromo, tosyl or mesyl group. To convert the hydroxyl group into chloro, a chlorination reagent such as thionyl chloride, concentrated hydrochloric acid or carbon tetrachloride-triphenylphosphine may be used, but other chlorination agents may also be employed. To convert the hydroxyl group into bromo, a bromination reagent such as thionyl bromide, hydrobromic acid or carbon tetrabromide-triphenylphosphine may be used, but other bromination agents may also be employed. To convert the hydroxyl group into tosyl or mesyl group, the reaction product is reacted with methanesulfonyl chloride or p-toluenesulfonyl chloride, respectively, in the presence of a base such as pyridine or triethylamine. This step may usually be carried out at −20° C. to room temperature, and preferably carried out under cooling in ice. As the solvent, a halogen-containing solvent such as methylene chloride or chloroform may be employed, but pyridine or the like may also be employed. Although the mixing ratio of XXXXIV to the chlorination agent, bromination agent or the reagent such as sulfonyl chloride or the like at the beginning of the reaction is not restricted, usually about 1:1 to 1:3 by mole is appropriate. The reaction time may appropriately be selected depending on the reaction temperature and the like, and may usually be about 2 to 30 hours.

Step 9 is the step for reacting XXXXV with VII at room temperature to 100° C., preferably at 70° C. to 80° C. in a polar solvent such as acetonitrile or dimethylformamide in the presence of a base. As the base, potassium carbonate is usually employed, but other bases may also be employed. Although the mixing ratio of XXXXV to VII at the beginning of the reaction is not restricted, usually about 1:1 to 1:2 by mole is appropriate. The reaction time may appropriately be selected depending on the reaction temperature and the like, and may usually be about 2 to 48 hours.

Step 10 is the step for reducing the double bond. The step may usually be carried out by hydrogenation by using a palladium-based catalyst such as palladium/carbon or palladium hydroxide, or using a platinum-based catalyst such as platinum dioxide, in an alcoholic solvent such as methanol or ethanol, or in a polar solvent such as ethyl acetate, tetrahydrofuran or dioxane, but other methods may also be employed. The reaction temperature is not restricted, and usually about 10° C. to 30° C. is appropriate. The reaction time may appropriately be selected depending on the reaction temperature and the like, and may usually be about 2 to 40 hours.

In cases where the novel triazolo derivative according to the present invention contains one or more asymmetric carbon atoms, racemic compounds, diastereomers and each of the optical isomers could exist, and any of these may be used in the present invention.

Examples of pharmaceutically acceptable salts of the compounds represented by Formula I include inorganic acid salts such as hydrochloric acid salt, hydrobromic acid salt, sulfuric acid salt, boric acid salt and phosphoric acid salt; organic acid salts such as maleic acid salt, fumaric acid salt, tartaric acid salt, succinic acid salt, malic acid salt, lactic acid salt, citric acid salt, malonic acid salt, benzoic acid salt, paratoluenesulfonic acid salt and methanesulfonic acid salt; and acid addition salts such as lysine, glycine, phenylalanine, asparagine and glutamine-added salts.

The triazolo derivatives represented by Formula I and pharmaceutically acceptable salts thereof may be used for therapy of various diseases utilizing inhibition of the actions of chemokines mediated through chemokine receptors such as CCR1, CCR2 and CCR3, especially, the actions of CC chemokines. For example, the triazolo derivatives represented by Formula I and pharmaceutically acceptable salts thereof are useful as therapeutic agents for allergic diseases such as bronchial asthma and atopic dermatitis; inflammatory diseases such as chronic rheumatoid arthritis; and for autoimmune diseases such as nephritis and ulcerative colitis; and as anti-AIDS drugs. They are also useful for prophylaxis and therapy of various diseases other than those mentioned above, in which chemokines are thought to participate.

The compounds represented by Formula I and acid addition salts thereof may be administered orally or parenterally (e.g., percutaneous, intravenous or rectal administration) as they are in the form of powder or as medical compositions in appropriate formulations to mammals. Examples of the formulations for administration include tablets, powders, balls, capsules, granules, syrups, liquids, injection solutions, emulsions, suspensions and suppositories. These formulations may be prepared by known methods, and include various carriers which are conventionally used in the field of formulation of medicines. Examples of these carriers include, for solid formulations, vehicles, lubricants, binders and disintegrators; for liquid formulations, solvents, solubilizers, suspending agents and soothing agents. Additives such as preservatives, antioxidants, coloring agents, sweetners, adsorbing agents and wetting agents may be used.

Examples of the vehicles include lactose, saccharose, D-mannitol, starch, sucrose, corn starch, crystalline cellulose and light anhydrous silicic acid. Examples of the lubricants include magnesium stearate, calcium stearate, talc and colloidal silica. Examples of the binders include crystalline cellulose, saccharose, D-mannitol, dextrin, hydroxyprqpyl cellulose, hydroxypropylmethyl cellulose, polyvinylpyrrolidone, starch, sucrose, gelatin, methyl cellulose and sodium carboxymethyl cellulose. Examples of the disintegrators include starch, carboxymethyl cellulose, potassium carboxymethyl cellulose, croscarmellose sodium, sodium carboxymethyl starch and L-hydroxypropyl cellulose. Examples of the solvents include water for injection, alcohol, propylene glycol, Macrogol, sesame oil and corn oil. Examples of the solubilizers include polyethylene glycol, propylene glycol, D-mannitol, benzyl benzoate, ethanol, cholesterol, triethanolamine, sodium carbonate and sodium citrate. Examples of the suspending agents include surfactants such as stearyl triethanolamine, sodium lauryl sulfate, lauryl aminopropionate, lecithin, benzalkonium chloride, benzethonium chloride and glycerin monostearate; and hydrophilic macromolecules such as polyvinyl alcohol, polyvinyl pyrrolidone, methyl cellulose, hydroxymethyl cellulose, hydroxyethyl cellulose and hydroxypropyl cellulose. Examples of the isotonic agents include glucose, sodium chloride, D-sorbitol and D-mannitol. Examples of the buffering agents include phosphoric acid salts, acetic acid salts, carbonic acid salts and citric acid salts. Examples of the soothing agents include benzyl alcohol. Examples of the antiseptics include paraoxy benzoic acid esters, chlorobutanol, benzyl alcohol, phenethyl alcohol, dehydroacetic acid and sorbic acid. Examples of the antioxidants include sulfurous acid salts and ascorbic acid.

The effective dose and the number of administration of the compound of Formula I or the pharmaceutically acceptable salt thereof vary depending on the formulation, and age, body weight, state or severity of the symptom of the patient, but usually 0.1 to 1000 mg, preferably 1 to 200 mg of the compound or the salt thereof may be administered to an adult per day in one time or in several times.

Unless undesirable interactions with the compound of Formula I or the pharmaceutically acceptable salt thereof occur, the formulation may include one or more of other therapeutically effective components. Examples of such therapeutic components include steroid drugs, nonsteroidal anti-inflammatory drugs, lipoxygenase inhibitors, leucotriene antagonists, bronchodilators, thromboxane synthesis inhibitors, thromboxane antagonists, histamine antagonists, histamine liberation inhibitors, platelet activating factor (PAF) antagonists, serotonin antagonists, adenosine receptor antagonists, adrenergic β-receptor antagonists, immunosuppressive agents and immunomodulators.

The effects of the present invention will now be described concretely by way of examples. It should be noted that the present invention is not restricted to the examples.

EXAMPLE 1

N-(3-Hydroxypropyl)(2-aminophenyl)formamide (1)

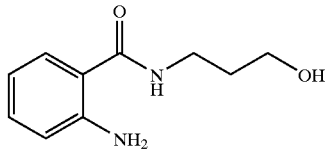

(1)

Isatoic anhydride (6.0 g) and 3-aminopropanol (2.8 ml) were dissolved in tetrahydrofuran (100 ml) and the mixture was stirred at room temperature for 4 hours. Tetrahydrofuran was removed and the residue was purified by silica gel chromatography (ethyl acetate) to obtain 5.94 g of N-(3-hydroxypropyl)(2-aminophenyl)formamide. Yield: 83%.

MS (EI, m/z): 194 (M$^+$); IR (KBr): 3467, 3358, 3280, 2943, 1627, 1542, 1267, 1062, 930, 748, 686 cm$^{-1}$; $^1$H NMR (300 MHz, CDCl$_3$) δ: 1.76(quint,J=6.0), 3.26(1H,brs), 3.58 (2H,q,J=6.0), 3.70(2H,q,J=5.5), 5.50(2H,s), 6.52(1H,brs), 6.61–6.69(2H,m), 7.21(1H,dt,J=7.1,1.4), 7.30(1H,dd,J=8.0, 1.4).

EXAMPLE 2

3-(3-Hydroxypropyl)-2-thioxohydroquinazoline-4-one (2)

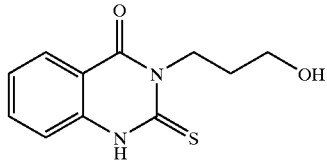

(2)

N-(3-hydroxypropyl)(2-aminophenyl)formamide (2.04 g), sodium hydroxide (817 mg) and carbon disulfide (2.4 ml) were added to ethanol (15 ml). The mixture was stirred at 60° C. for 5 hours, and then carbon disulfide (0.3 ml) was added, followed by stirring the mixture overnight. Water was added to the reaction mixture and the precipitates were recovered by filtration to obtain 2.23 g of 3-(3-hydroxypropyl)-2-thioxohydroquinazoline-4-one. Yield: 90%.

m.p.: 182–184° C. MS (EI, m/z): 236 (M+); IR (KBr): 3334, 3207, 2965, 2871, 1694, 1622, 1539, 1133, 1034, 687, 640 cm$^{-1}$; $^1$H NMR (300 MHz, DMSO); δ: 1.81(2H,quint, J=7.7), 3.46(2H,q,J=5.5), 4.42(2H,t,J=7.4), 4.50(1H,t,J= 5.2), 7.31(1H,t,J=8.0), 7.3 6(1H,d,J=8.2), 7.72(1H,t,J=8.2), 7.94(1H,d,J=8.0).

EXAMPLE 3

2,4,5,7-Tetraaza-7-(3-hydroxypropyl)-3-methyltricyclo[7.4.0.0<2,6>]trideca-1(13),3,5,9(10), 11-pentaene-8-one (3)

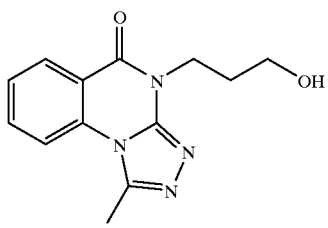

(3)

3-(3-hydroxypropyl)-2-thioxohydroquinazoline-4-one (2.04 g) was added to ethanol (40 ml) and hydrazine hydrate (20 ml), and the mixture was stirred at 80 to 90° C. for 3 hours. Ethanol and hydrazine were removed and n-butanol (30 ml) and orthotriethyl acetate (4.3 ml) were added to the residue, followed by stirring the resulting mixture at 110° C. for 3 hours. The solvent was removed and the residue was purified by silica gel column chromatography (dichloroethane:ethanol=6:1) to obtain 1.1 g of 2,4,5,7-tetraaza-7-(3-hydroxypropyl)-3-methyltricyclo[7.4.0.0<2, 6>]trideca-1(13),3,5,9(10),11-pentaene-8-one. Yield: 49.8%.

MS (m/z, EI): 258 (M+); IR (KBr): 3364, 2954, 1675, 1499, 1081, 764 cm$^{-1}$; $^1$H NMR (300 MHz, DMSO); δ: 1.87(2H,quint,J=6.6), 2.83(3H,s), 3.48(2H,t,J=6.2), 7.90 (1H,t,J=7.4), 8.03(1H,d,J=8.2), 8.24(1H,d,J=7.7).

EXAMPLE 4

2,4,5,7-Tetraaza-7-(3-chloropropyl)-3-methyltricyclo [7.4.0.0<2,6>]trideca-1(13),3,5,9(10),11-pentaene-8-one (4)

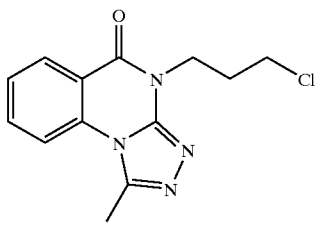

(4)

2,4,5,7-tetraaza-7-(3-hydroxypropyl)-3-methyltricyclo [7.4.0.0<2,6>]trideca-1(13),3,5,9(10),11-pentaene-8-one (980 mg) was dissolved in dichloromethane (70 ml), and carbon tetrachloride (1 ml) and triphenylphosphine (2.9 g) were added, followed by stirring the mixture overnight at room temperature. Carbon tetrachloride and triphenylphosphine were further added and the resulting mixture was stirred at room temperature for another two nights until the reaction completed. The solvent was removed and the residue was purified by silica gel chromatography (ethyl acetate:ethanol=8:1) to obtain 915 mg of 2,4,5,7-tetraaza-7-(3-chloropropyl)-3-methyltricyclo[7.4.0.0<2,6>]trideca-1 (13),3,5,9(10),11-pentaene-8-one. Yield 87%.

m.p.: 157–159° C. MS (EI, m/z): 276 (M+); IR (KBr): 1676, 1568, 1491, 1441, 764 cm$^{-1}$; $^1$H NMR (300 MHz, CDCl$_3$); δ: 2.38(2H,quint,J=6.9), 2.95(3H,s), 3.66(2H,t,J= 6.9), 4.53(2H,t,J=7.2) 7.57(1H,t,J=7.2), 7.83(1H,t,J=7.2), 7.89(1H,d,J=7.7), 8.46(1H,d,J=7.8).

EXAMPLE 5

2,4,5,7-Tetraaza-7-(3-(3-indole-3-ylpiperidyl) propyl)-3-methyltricyclo[7.4.0.0<2,6>]trideca-1(13), 3,5,9(10),11-pentaene-8-one (5)

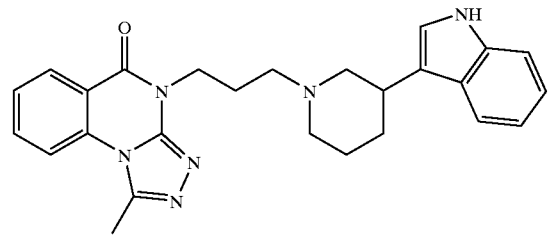

(5)

3-(3-piperidino)indole (225 mg), 2,4,5,7-tetraaza-7-(3-chloropropyl)-3-methyltricyclo[7.4.0.0<2,6>]trideca-1(13), 3,5,9(10),11-pentaene-8-one (285 potassium carbonate (142 mg) were added to dimethylformamide (7 ml), and the mixture was stirred at 70° C. for 6 hours and then at 90° C. for 2 hours, followed by removal of dimethylformamide. Water was added to the residue and the resultant was extracted three times with dichloromethane. The organic layers were combined and dried over anhydrous sodium sulfate. Dichloromethane was removed and the residue was purified by silica gel column chromatography (ethyl acetate:ethanol=3:1) to obtain 193 mg of 2,4,5,7-tetraaza-7-(3-(4-indole-3-ylpiperidyl)propyl)-3-methyltricyclo [7.4.0.0<2,6>]trideca-1(13),3,5,9(10),11-pentaene-8-one. Yield: 42%.

m.p.: 207–209° C. (decomposed); IR (KBr): 3244, 2922, 1680, 1608, 1573, 1491, 1438, 754 cm$^{-1}$; $^1$H NMR (300 MHz, CDCl$_3$) δ: 1.3–2.1(5H,m), 2.11(2H,quint,J=7.2), 2.55 (2H,t,J=7.2), 2.90(3H,m), 2.92(3H,s), 3.12(1H,brd), 4.47 (2H,t,J=7.2), 6.97(1H,s), 7.05–7.09(2H,m), 7.33(1H,d,J= 7.8), 7.55(1H,t,J=8.0), 7.62(1H,d,J=8.7), 7.81(1H,t,J=7.8), 7.81(1H,t,J=7.8), 7.86(1H,t,J=8.0), 7.98(1H,brs), 8.46(1H, d,J=7.2); HR-MS: Calcd.: C$_{26}$H$_{28}$N$_6$O 440.2325; Found: 440.2307.

EXAMPLE 6

2,4,5,7-Tetraaza-7-(3-(4-indole-3-ylpiperidyl)propyl)-3-methyltricyclo[7.4.0.0<2,6>]trideca-1(13),3,5,9(10),11-pentaene-8-one (6)

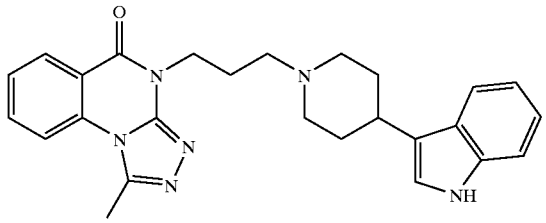

(6)

3-(3-piperidino)indole (280 mg), 2,4,5,7-tetraaza-7-(3-chloropropyl)-3-methyltricyclo[7.4.0.0<2,6>]trideca-1(13),3,5,9(110),11-pentaene-8-one (270 mg) a potassium carbonate (220 mg) were added to dimethylformamide (7 ml) and the mixture was stirred at 80° C. for 7 hours, followed by removal of dimethylformamide. Water was added to the residue and the resultant was extracted three times with dichloromethane. The organic layers were combined and dried over anhydrous sodium sulfate. Dichloromethane was removed and the residue was purified by silica gel column chromatography (ethyl acetate:ethanol=5:1) to obtain 135 mg of 2,4,5,7-tetraaza-7-(3-(3-indole-3-ylpiperidyl)propyl)-3-methyltricyclo[7.4.0.0<2,6>]trideca-1(13),3,5,9(10),11-pentaene-8-one. Yield: 31%.

m.p.: 207–212° C. (decomposed); IR (KBr): 3250, 2925, 1681, 1609, 1574, 1490, 1437, 757 cm$^{-1}$; $^1$H NMR (300 MHz, CDCl$_3$) δ: 1.95–2.17(8H,m), 2.58(2H,t,J=7.2), 2.76 (1H,m), 2.94(3H,s), 3.00(2H,brd,J=11.8), 4.47(2H t,J=6.8), 6.87(1H,s), 7.07(1H,t,J=8.0), 7.17(1H,t,J=8.0), 7.34(1H,d, J=8.0), 7.57(1H,mt,J=7.2), 7.81(1H,t,J=8.4), 7.87(1H,s), 7.90(1H,t,J=8.0), 8.48(1H,d,J=8.0); HR-MS: Calcd.: C$_{26}$H$_{28}$N$_6$O 440.2325 Found: 440.2295.

EXAMPLE 7

2,4,5,7-Tetraaza-3-methyl-7-(3-(4-diphenylmethylene)piperidyl)propyl)tricyclo[7.4.0.0<2,6>]trideca-1(13),3,5,9(10),11-pentaene-8-one (7)

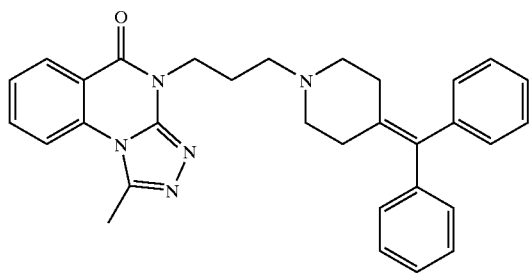

(7)

Diphenylmethylenepiperidine (390 mg), 2,4,5,7-tetraaza-7-(3-chloropropyl)-3-methyltricyclo[7.4.0.0<2,6>]trideca-1 (13),3,5,9(10),11-pentaene-8-one (312 mg) and potassium carbonate (360 mg) were added to dimethylformamide (7 ml), and the mixture was stirred at 70° C. for 8 hours, followed by removal of dimethylformamide. Water was added to the residue and the resultant was extracted with dichloromethane. Organic layers were combined and dried over anhydrous sodium sulfate. Dichloromethane was removed and the residue was purified by silica gel column chromatography (ethyl acetate:ethanol=5:1) to obtain 194 mg of 2,4,5,7-tetraaza-3-methyl-7-(3-(4-diphenylmethylene)piperidyl)propyl)tricyclo[7.4.0.0<2,6>]trideca-1(13),3,5,9(10),11-pentaene-8-one. Yield: 35%.

m.p.: 157–159° C. IR (KBr): 2953, 2806, 1675, 1571, 1491, 761, 704 cm$^{-1}$; $^1$H NMR (300 MHz, CDCl$_3$); δ: 2.08(2H,q,J=7.0), 2.29(4H,m), 2.46(4H,m), 2.53(2H,t,J=7.8), 2.94(3H,s), 4.44(2H,t,J=7.4), 7.56(1H,t,J=8.0), 7.82 (1H,d,8.2), 7.87(1H,d,8.2), 8.45(1H,d,J=8.0); HR-MS: Calcd.: C$_{31}$H$_{31}$N$_5$O 489.2529 Found: 489.2545.

EXAMPLE 8

Ethyl 4-(Diphenylmethoxy)piperidine Carboxylate (8)

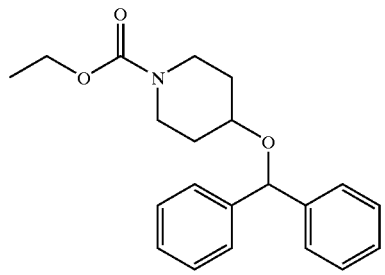

(8)

Aqueous sodium hydroxide solution (4.2 g, 70 ml) was added to diphenylmethoxypiperidine hydrochloride, and the mixture was extracted twice with dichloromethane. Organic layers were combined and dried over anhydrous sodium sulfate. After removing dichloromethane, the residue was dissolved in toluene (75 ml) and ethyl chloroformate (3.9 ml) was added thereto. The mixture was stirred at 70° C. for 10 hours, and then ethyl chloroformate (3.5 ml) was added, followed by stirring the resulting mixture at 7° C. for another 10 hours. Water was added to the reaction solution and the mixture was extracted twice with ethyl acetate. Organic layers were combined and dried over anhydrous sodium sulfate. The solvent was removed and the residue was purified by silica gel column chromatography (ethyl acetate:hexane=5:1) to obtain 9.7 g of ethyl 4-(diphenylmethoxy)piperidine carboxylate. Yield: 75%.

$^1$H NMR (300 MHz, CDCl$_3$) δ: 1.24(3H,t,J=7.1), 1.58–1.89(4H,m), 3.15–3.24(2H,m), 3.55–3.66(1H,m), 3.75–3.78(2H,m), 4.11(2H,q,J=7.1), 5.52((1H,s), 7.22–7.35 (10H,m).

EXAMPLE 9

4-Diphenylmethoxypiperidine (9)

(9)

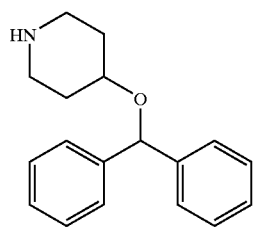

Ethyl 4-(diphenylmethoxy)piperidine carboxylate (9.7 g) was dissolved in ethanol (85 ml) and water (35 ml), and sodium hydroxide (6.1 g) was added to the mixture, followed by heating the mixture to reflux for 40 hours. Ethanol was removed and water was added to the residue, followed by extraction of the resultant with dichloromethane. Organic layers were combined and dried over anhydrous sodium sulfate. Dichloromethane was removed and the residue was purified with Chromatorex® column chromatography for amines (ethyl acetate:ethanol=5:1) to obtain 7.1 of 4-diphenylmethoxypiperidine. Yield: 90%.

IR (KBr): 3288, 2934, 1450, 1090, 700 cm$^{-1}$; $^1$H NMR (300 MHz, CDCl$_3$) δ: 1.40–1.60(2H,m), 1.85–1.97(2H,m), 2.50–2.62(2H,m), 3.02–3.15(2H,m), 3.40–3.57(2H,m), 5.55 (1H,s), 7.20–7.42(10H,m).

EXAMPLE 10

2,4,5,7-Tetraaza-3-methyl-7-(3-(4-diphenylmethoxy) piperidyl)propyl)tricyclo[7.4.0.0<2,6>]trideca-1(13), 3,5,9(10),11-pentaene-8-one (10)

(10)

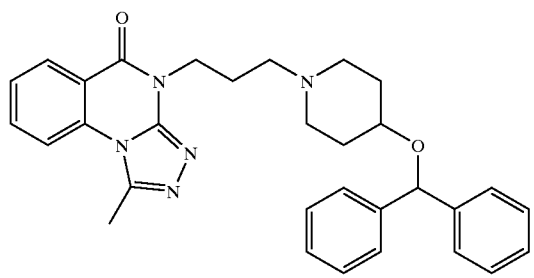

4-diphenylmethoxypiperidine (370 mg), 2,4,5,7-tetraaza-7-(3-chloropropyl)-3-methyltricyclo[7.4.0.0<2,6>]trideca-1 (13),3,5,9(10),11-pentaene-8-one (370 mg) and potassium carbonate (190 mg) were added to dimethylformamide (7 ml) and the mixture was stirred at 80° C. for 16 hours, followed by removal of dimethylformamide. Water was added to the residue and the mixture was extracted three times with dichloromethane. Organic layers were combined and dried over anhydrous sodium sulfate. Dichloromethane was removed and the residue was purified by silica gel column chromatography (ethyl acetate:ethanol 8:1) to obtain 255 mg of 2,4,5,7-tetraaza-3-methyl-7-(3-(4-diphenylmethoxy)piperidyl)propyl)tricyclo[7.4.0.0<2,6>] trideca-1(13),3,5,9(10),11-pentaene-8-one. Yield: 36%.

IR (KBr): 2940, 1678, 1613, 1572, 1071, 758, 703 cm$^{-1}$; $^1$H NMR (300 MHz, CDCl$_3$) δ: 1.40–1.83(4H,m), 1.92–2.11 (4H,m), 2.47(2H,t,J=7.1), 2.60–2.74(2H,m), 2.93(3H,m), 3.34(1H,m), 5.45(1H,s), 7.14–7.42(10H,m), 7.55(1H,t,J= 8.0), 7.80(1H,t,J=7.7), 7.86(1H,d,J=7.7) 8.44(1H,dd,J=8.0, 1.0); HR-MS: Calcd.: C$_{31}$H$_{31}$N$_5$O 507.2635 Found: 507.2642.

EXAMPLE 11

2,4,5,7-Tetraaza-3-methyl-7-(3-(4-((2-phenylphenyl) methyl)piperazinyl)propyl)tricyclo[7.4.0.0<2,6>] trideca-1(13),3,5,9(10),11-pentaene-8-one (11)

(11)

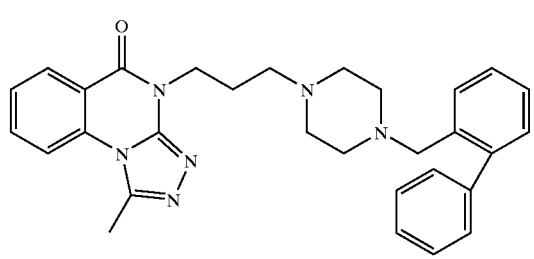

2,4,5,7-tetraaza-7-(3-chloropropyl)-3-methyltricyclo [7.4.0.0<2,6>]trideca-1(13),3,5,9(10),11-pentaene-8-one (226 mg), N-(2-phenylbenzyl)piperazine (230 mg) and potassium carbonate (240 mg) were added to acetonitrile (8 ml) and the mixture was stirred at 80° C. for 2 days and nights. Water was added to the reaction mixture and the resultant was extracted with dichloromethane. Organic layers were combined and dried over anhydrous sodium sulfate. Dichloromethane was removed and the residue was purified by silica gel column chromatography (ethyl acetate:ethanol= 12:1) to obtain 165 mg of 2,4,5,7-tetraaza-3-methyl-7-(3-(4-((2-phenylphenyl)methyl)piperazinyl)propyl)tricyclo [7.4.0.0<2,6>]trideca-1(13),3,5,9(10),11 pentaene-8-one. Yield: 41%.

IR (KBr): 3478, 2984, 1696, 1634, 1443, 952, 760 cm$^{-1}$; $^1$H NMR (300 MHz, CDCl$_3$) δ: 2.03(2H,quint,J=7.0), 2.0–2.40(8H,m), 2.47(2H,t,J=7.0), 2.90(3H,s), 3.26(2H,s), 4.42(2H,t,J=7.2), 7.2–7.55(10H,m), 7.75(1H,d,J=7.8), 7.78 (1H,t,J=7.4), 8.43(1H,d,J=7.8); HR-MS: Calcd.: C$_{30}$H$_{32}$N$_6$O$_2$ 492.2637 Found: 492.2610.

EXAMPLE 12

2,4,5,7-Tetraaza-3-methyl-7-(3-(4-cyclohexyl) piperazinyl)propyl)tricyclo[7.4.0.0<2,6>]trideca-1 (13),3,5,9(10),11-pentaene-8-one (12)

(12)

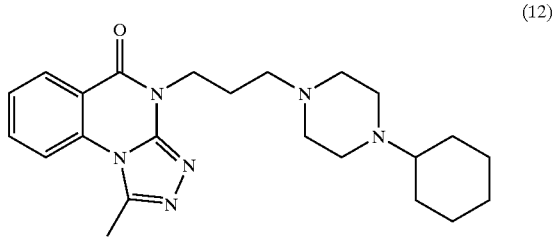

2,4,5,7-tetraaza-7-(3-chloropropyl)-3-methyltricyclo [7.4.0.0<2,6>]trideca-1(13),3,5,9(10),11-pentaene-8-one (204 mg), cyclohexylpiperazine (176 mg) and potassium carbonate (142 mg) were added to acetonitrile (10 ml), and the mixture was stirred at 90° C. for 20 hours. Acetonitrile was removed and water was added to the residue, followed by extracting the mixture 3 times with dichloromethane. Organic layers were combined and the residue was purified by silica gel column chromatography (dichloromethane:ethanol=3:1) to obtain 145 mg of 2,4,5,7-tetraaza-3-methyl-7-(3-(4-cyclohexyl)piperazinyl)propyl) tricyclo[7.4.0.0<2,6>]trideca-1(13),3,5,9(10),11-pentaene-8-one. Yield: 48%.

m.p.: 118–120° C. IR (KBr): 2926, 2853, 2815, 1675, 1569, 1492, 1445, 1159, 761 cm$^{-1}$; $^1$H NMR (300 MHz, CDCl$_3$) δ: 1.00–1.30(6H,m), 1.60–1.85(4H,m), 2.10–2.23 (1H,m), 2.25–2.60(8H,m), 2.51(2H,t,J=7.2), 2.94(3H,s), 4.44(2H,t,J=7.2), 7.56(1H,t,J=7.2), 7.81(1H,td,J=7.2,1.4), 8.45(1H,dd,J=8.0,1.4), 7.85(1H,d,J=7.4); HR-MS: Calcd.: C$_{23}$H$_{33}$N$_6$ (M+H)$^+$ 409.2716 Found: 409.2718.

EXAMPLE 13

4-Diphenylmethylpiperidine (13)

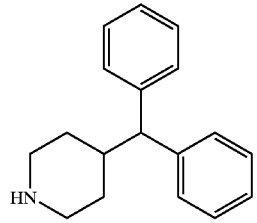

(13)

4-diphenylmethylenepiperidine hydrochloride (6.21 g) was added to methanol (30 ml) and the atmosphere was replaced with argon. To the mixture, 10% palladium-carbon (1.54 g) and a small amount of concentrated hydrochloric acid were added and the atmosphere was replaced with hydrogen, followed by allowing the mixture to react at 3.5 atm at room temperature for 10.5 hours. Then 10% palladium-carbon was removed through Celite and the filtrate was concentrated. The residue was again dissolved in methanol (30 ml) and 10% palladium-carbon (10 g) and a small amount of hydrochloric acid were added. The atmosphere was replaced with hydrogen, and the mixture was allowed to react at 3.5 atm at room temperature for 21 hours. The reaction mixture was filtered through Celite and the filtrate was concentrated, followed by recrystallizing the residue from methanol/ether to obtain 2.38g of 4-diphenylmethylpiperidine hydrochloride. Yield: 38%.

m.p.: 259–268° C. (hydrochloride); MS (FAB, m/z): 252((M+H)$^+$); IR (KBr): 2923, 2794, 2494, 1635, 1578, 1494, 1447, 1429, 1317, 1280, 1138, 1073, 958 cm$^{-1}$; $^1$H NMR (300 MHz, CD$_3$OD) δ: 1.35(1H,ddd,J=28.3,15.1,4.1), 1.76(2H,d,J=14.3), 2.57(1H,ddt,J=22.8,11.3,3.3), 2.97(2H, dt,J=12.9,3.0), 3.29–3.35(2H,m), 3.58(2H,d,J=11.3), 7.16 (2H,tt,J=6.3,1.4), 7.27(4H,t,J=6.6), 7.36(4H,d,J=7.1).

EXAMPLE 14

2,4,5,7-Tetraaza-3-methyl-7-(3-(4-diphenylmethyl) piperidyl)propyl)tricyclo[7.4.0.0<2,6>]trideca-1(13), 3,5,9(10),11-pentaene-8-one (14)

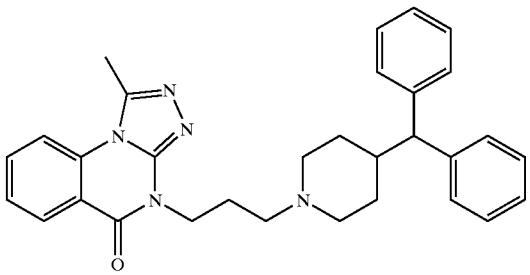

(14)

4-diphenylmethylpiperidine hydrochloride (230 mg), 2,4, 5,7-tetraaza-7-(3-chloropropyl)-3-methyltricyclo[7.4.0.0<2, 6>]trideca-1(13),3,5,9(10),11-pentaene-8-one (328 mg) and potassium carbonate (909 mg) were added to acetonitrile (8 ml) and the mixture was stirred at 110° C. for 44 hours. The reaction mixture was filtered and the filtrate was concentrated, followed by purifying the residue by silica gel column chromatography (ethyl acetate-methanol:chloroform=1:100–1:10) to obtain 332 mg of 2,4, 5,7-tetraaza-3-methyl-7-(3-(4-diphenylmethyl)piperidyl) propyl)tricyclo[7.4.0.0<2,6>]trideca-1(13),3,5,9(10),11-pentaene-8-one (Yield: 84%). The free compound was dissolved in 5 ml of methanol and 0.3 ml of hydrochloric acid/methanol (2.5 M) was added at room temperature (pH=2) to obtain the corresponding hydrochloride. After concentration, the obtained crystals were recrystallized from methanol/ether to obtain 231 mg of the corresponding hydrochloride. Crystallization Yield: 65%.

m.p.: 172.8–190.5° C. (hydrochloride); MS (free compound, EI, m/z): 491 (M$^+$); IR (free compound, neat): 2942, 2245, 1680, 1613, 1600, 1573, 1537, 1493, 1443, 910, 757, 732 cm$^{-1}$; $^1$H NMR (free compound, 300MHz, CDCl$_3$) δ: 1.01(2H,dd,J=21.7,11.8 Hz), 1.46(2H,d,J=11.5 Hz), 2.01–2.09(3H,m), 2.48(2H,t,J=6.9), 2.83(2H,d,J=11.8), 2.93 (3H,s), 3.34(2H,d,J=11.0), 7.10–7.19(2H,m), 7.21–7.27(8H, m), 7.57(1H,dt,J=7.1,1.4), 7.81–7.91(2H,m), 8.45(1H,dd,J= 8.2,1.4).

EXAMPLE 15

1-Acetyl-4-((3-phenoxyphenyl)methyl)piperazine (15)

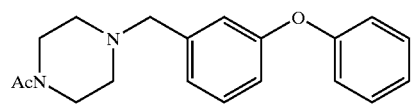

(15)

3-phenoxybenzaldehyde (1.0 g) and 1-acetylpiperazine (739 mg) were dissolved in 1,2-dichloroethane (10 ml) and sodium triacetoxyboro hydride (1.72 g) and acetic acid (300 mg) were added. The atmosphere was replaced with argon and the mixture was stirred at room temperature for 6.5 hours. Water (5 ml) and saturated sodium hydrogen carbonate (20 ml) were added and the aqueous layer was extracted 5 times with chloroform. Organic layers were combined and dried over anhydrous sodium sulfate. Chloroform was removed and the residue was purified by silica gel column chromatography (ethyl adetate-ethyl acetate:methanol=20:1–10:1) to obtain 1.32 g of 1-acetyl-4-((3-phenoxyphenyl)methyl)piperazine. Yield: 84%.

MS (EI, m/z): 310 (M$^+$); IR (neat): 2915, 2809, 2767, 2240, 1736, 1641, 1584, 1487, 1442, 1251, 1215, 1000, 911 cm$^{-1}$; $^1$H NMR (300 MHz, CDCl$_3$) δ: 2.08(3H,s), 2.42(4H,dd,J=5.5,10.4), 3.44(2H,t,J=5.5), 3.50(2H,s), 3.61(2H,t,J=4.9), 6.90(1H,ddd,J=8.2,2.5,1.1), 6.98–7.13(5H,m), 7.25–7.37(3H,m).

EXAMPLE 16

1-((3-Phenoxyphenyl)methyl)piperazine (16)

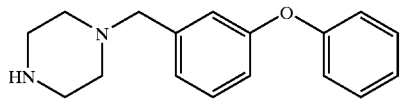

(16)

300 mg of 1-((3-phenoxyphenyl)methyl)piperazine was dissolved in ethanol (20 ml) and aqueous potassium hydroxide solution (3 ml, potassium hydroxide 1 g) was added, followed by heating the mixture to reflux for 4 hours. Water was added to the reaction mixture and the resultant was extracted 3 times with chloroform. Organic layers were combined and dried over anhydrous sodium sulfate, followed by removal of chloroform to obtain 237 mg of 1-((3-phenoxyphenyl)methyl)piperazine. Yield: 91%.

MS (EI, m/z): 268 (M$^+$); IR (neat): 2943, 2811, 1584, 1488, 1442, 1253, 1215, 909 cm$^{-1}$; $^1$H NMR (300 MHz, CDCl$_3$); δ: 2.40(4H,bs), 2.87(2H,t,J=4.9), 3.47(2H,s), 6.88 (1H,ddd,J=8.1,2.5,0.8), 6.99–7.12(5H,m), 7.24–7.37(3H,m).

EXAMPLE 17

2,4,5,7-Tetraaza-3-methyl-7-(3-(4-((3-phenoxyphenyl)methyl)piperazinyl)propyl)tricyclo[7.4.0.0<2,6>]trideca-1(13),3,5,9(10),11-pentaene-8-one (17)

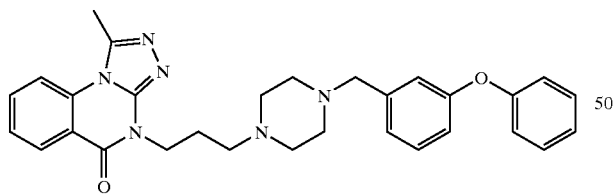

(17)

1-((3-phenoxyphenyl)methyl)piperazine (237 mg), 2,4,5,7-tetraaza-7-(3-chloropropyl)-3-methyltricyclo[7.4.0.0<2,6>]trideca-1(13),3,5,9(10),11-pentaene-8-one (274 mg), potassium carbonate (628 mg) and potassium iodide (176 mg) were added to acetonitrile (8 ml) and the atmosphere was replaced with argon, followed by stirring the mixture at 110° C. for 10 hours. The reaction mixture was filtered and the filtrate was concentrated. The residue was purified by preparative thin layer chromatography (methanol:chloroform=1:15) to obtain 210 mg of 2,4,5,7-tetraaza-3-methyl-7-(3-(4-((3-phenoxyphenyl)methyl)piperazinyl)propyl)tricyclo[7.4.0.0<2,6>]trideca-1(13),3,5, 9(10),11-pentaene-8-one. Yield: 42%. The free compound was dissolved in methanol (5 ml) and hydrochloric acid/methanol (2.5 M, 0.2 ml) was added at room temperature (pH=2) to obtain the corresponding hydrochloride. After concentration, the obtained colorless crystals were recrystallized from methanol/ether to obtain 163 mg of the corresponding hydrochloride. Crystallization Yield: 72%.

m.p.: 225–230.5° C. (hydrochloride); MS (free compound, CI, m/z): 509((M+H)$^+$); IR (free compound, neat): 2942, 2814, 2250, 1678, 1614, 1600, 1574, 1492, 909, 733 cm$^{-1}$; $^1$H NMR (free compound, 300 MHz, CDCl$_3$) δ: 2.06(2H,t,J=7.1), 2.40(8H,bs), 2.51(2H,t,J=7.1), 2.94(3H,s), 3.39(2H,s), 4.44(2H,t,J=7.1), 6.87(1H,ddd,J=8.0,2.5,0.8), 6.95–7.02(4H,m), 7.09(1H,tt,J=6.9,1.1), 7.22–7.37(3H,m), 7.55(1H,tt,J=8.0,1.1), 7.79–7.89(2H,m), 8.45(1H,dd,J=8.0, 1.1).

EXAMPLE 18

1-Acetyl-4-((4-phenoxyphenyl)methyl)piperazine (18)

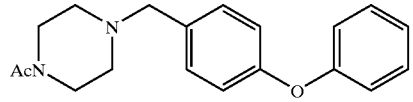

(18)

4-phenoxybenzaldehyde (989 mg) and 1-acetylpiperazine (713 mg) were dissolved in 1,2-dichloroethane (11 ml), and sodium triacetoxyboro hydride (1.60 g) and acetic acid (300 mg) were added. The atmosphere was replaced with argon and the mixture was stirred at room temperature for 7 hours. Water (5 ml) and aqueous saturated sodium hydrogen carbonate solution (20 ml) were added and the mixture was extracted 5 times with chloroform. Organic layers were combined and dried over anhydrous sodium sulfate. Chloroform was removed and the residue was purified by silica gel column chromatography (ethyl acetate-ethyl acetate:methanol=20:1–10:1) to quantitatively obtain 1.55 g of 1-acetyl-4-(4-phenoxybenzyl)piperazine.

MS (EI, m/z): 310 (M$^+$); IR (neat): 3002, 2916, 2805, 2238, 1736, 1642, 1590, 1489, 1000, 872, 753, 693 cm$^{-1}$; $^1$H NMR (300 MHz, CDCl$_3$) δ: 2.08(3H,s), 2.43(4H,dd,J=4.7, 10.2), 3.46(2H,t,J=4.9), 3.49(2H,s), 3.63(2H,t,J=4.9), 6.94–7.03(4H,m), 7.10(1H,dt,J=7.1,1.1), 7.25–7.37(4H,m).

EXAMPLE 19

1-((4-Phenoxyphenyl)methyl)piperazine (19)

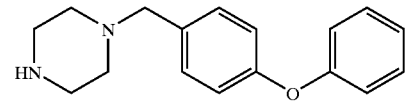

(19)

1-acetyl-4-((4-phenoxyphenyl)methyl)piperazine (316 mg) was dissolved in ethanol (20 ml), and aqueous potassium hydroxide solution (3 ml, potassium hydroxide 1 g) was added, followed by heating the mixture to reflux for 4 hours. Water was added to the reaction mixture and the mixture was extracted 3 times with chloroform. Organic layers were combined and dried over anhydrous sodium sulfate, followed by removal of chloroform to obtain 267 mg of 1-((4-phenoxyphenyl)methyl)piperazine. Yield: 98%.

MS (EI, m/z): 268 (M+); IR (neat): 2942, 2813, 1590, 1505, 1489, 1239, 754 cm$^{-1}$; $^1$H NMR (300 MHz CDCl$_3$) δ: 2.41(4H,bs), 2.88(2H,t,J=4.9), 3.46(2H,s), 6.93–7.02(4H, m), 7.08(1H,dt,J=7.1,1.1), 7.25–7.36(4H,m).

EXAMPLE 20

2,4,5,7-Tetraaza-3-methyl-7-(3-(4-((4-phenoxyphenyl)methyl)piperazinyl)propyl)tricyclo[7.4.0.0<2,6>]trideca-1(13),3,5,9(10),11-pentaene-8-one (20)

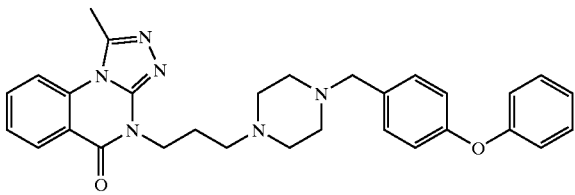

(20)

1-((4-phenoxyphenyl)methyl)piperazine (111 mg), 2,4,5, 7-tetraaza-7-(3-chloropropyl)-3-methyltricyclo[7.4.0.0<2, 6>]trideca-1(13),3,5,9(10),11-pentaene-8-one (429 mg), potassium carbonate (291 mg) and 70 mg of potassium iodide were dissolved in acetonitrile (8 ml), and the atmosphere was replaced with argon, followed by stirring the mixture at 110° C. for 9 hours. The reaction mixture was filtered and the filtrate was concentrated, followed by purifying the residue by preparative thin layer chromatography (methanol:chloroform=1:15) to obtain 706 mg of 2,4,5,7-tetraaza-3-methyl-7-(3-(4-((4-phenoxyphenyl)methyl) piperazinyl)propyl)tricyclo[7.4.0.0<2,6>]trideca-1(13),3,5, 9(10),11-pentaene-8-one. Yield: 36%. The free compound was dissolved in 1 ml of methanol and 0.1 ml of hydrochloric acid/methanol (2.5 M) was added at room temperature. After concentration, the obtained crystals were recrystallized from methanol/ether to obtain 45.6 mg of the corresponding hydrochloride. Crystallization Yield: 60%.

m.p.: 229–237° C. (hydrochloride); MS (free compound, EI, m/z): 508 (M+); IR (free compound, neat): 2938, 2812, 1679, 1613, 1599, 1573, 1492, 758, 731 cm$^{-1}$; $^1$H NMR (free compound, 300 MHz, CDCl$_3$); δ: 2.07(2H,t,J=6.9), 2.42(8H,bs), 2.53(2H,t,J=6.9), 2.95(3H,s), 3.40(2H,s), 4.44 (2H,t,J=6.9), 6.99(4H,dd,J=7.7,1.1), 7.09(1H,dt,J=8.5,1.1), 7.22(2H,d,J=8.5), 7.33(2H,t,J=8.5), 7.57(1H,t,J=7.1), 7.80–7.90(2H,m), 8.45(1H,dd,J=7.7,0.8).

EXAMPLE 21

1-Acetyl-3-(diphenylhydroxymethyl)piperidine (21)

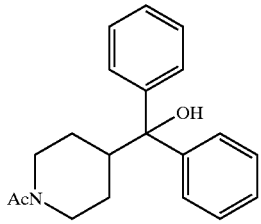

(21)

To 10 ml of ethyl nipecotate, 6.0 ml of acetic anhydride was added and the mixture was stirred at room temperature for 2 hours. Water was added to the reaction solution and the mixture was once extracted with ethyl acetate, followed by drying the organic layer over anhydrous sodium sulfate. The solvent was removed and the residue was purified by silica gel chromatography (ethyl acetate). 7.0 g of aliquot thereof was dissolved in 150 ml of anhydrous tetrahydrofuran and 105 ml of phenylmagnesium bromide solution (in 1 M tetrahydrofuran) was added dropwise under stirring at 0° C. The mixture was stirred at 0° C. for 30 minutes and then at room temperature for 2.5 hours. Aqueous saturated ammonium chloride solution was added and the mixture was extracted 3 times with dichloromethane. Organic layers were combined and dried over anhydrous sodium sulfate. The solvent was removed and the residue was recrystallized from ethyl acetate to obtain 4.8 g of 1-acetyl-3-(diphenylhydroxymethyl)piperidine. Yield: 44%.

MS (EI, m/z): 309 (M+); IR (KBr): 3422, 2955, 1606, 1444, 1361, 258, 1168, 1062, 970, 754, 703 cm$^{-1}$; $^1$H NMR (300 MHz, CDCl$_3$) δ: 1.30–1.88(4H,m), 1.82(1.5H,s), 2.08 (1.5H,s), 2.30–2.65(3H,m), 2.85–3.04(1H,m), 3.56(0.5H,d, J=1.4), 3.73(0.5H,d,J=1.4), 4.52–4.65(1H,m), 7.15–7.56 (10H,m).

EXAMPLE 22

1-Acetyl-3-(diphenylmethyl)piperidine (22)

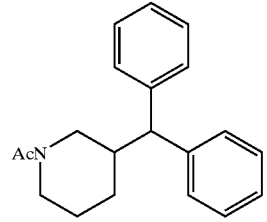

(22)

To 1-acetyl-3-(diphenylhydroxymethyl)piperidine (500 mg), acetic anhydride (2 ml) was added and the mixture was stirred at 140° C. for 16 hours. After concentration of the reaction solution, 10 ml of methanol and 30 mg of 10% palladium-carbon were added, followed by stirring the mixture under hydrogen atmosphere for 17 hours. Palladium was removed by filtration through Celite and the filtrate was concentrated to obtain 250 mg of 1-acetyl-3-(diphenylmethyl)piperidine. Yield: 52%.

MS (EI, m/z): 293 (M+); IR (neat): 3060, 2940, 2856, 1632, 1451, 1268, 748, 711, 578 cm$^{-1}$; $^1$H NMR (300 MHz, CDCl$_3$) δ: 1.03–1.27(1H,m), 1.34–1.52(1H,m), 1.62–1.80 (1.65H,m), 1.79(1.95H,s), 2.07(1.05H,s), 2.17(0.3 5H,t,J= 12.9), 2.25–2.44(1H,m), 2.77(1.3H,dd,J=9.9,13.5), 2.96 (0.35H,t,J=9.9), 3.44–3.61(2H,m), 3.76(0.35H,d,J=12.9), 4.28(0.65H,d,J=12.9), 4.54(0.35H,d,J=12.9), 7.14–7.32 (10H,m).

EXAMPLE 23

3-(Diphenylmethyl)piperidine (23)

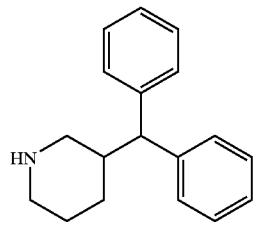

(23)

1-acetyl-3-(diphenylmethyl)piperidine (250 mg) was added to methanol (12 ml) and 10N aqueous potassium hydroxide solution (4 ml), and the mixture was stirred at 80° C. for 3 hours. Aqueous saturated potassium carbonate solution was added to the reaction solution and the mixture was extracted once with ethyl acetate, followed by drying the organic layer over anhydrous sodium sulfate. The solvent was removed to obtain 220 mg of 3-(diphenylmethyl)piperidine. Yield: 100%.

MS (EI, m/z): 251 (M$^+$); IR (KBr): 3024, 2939, 2798, 1492, 1450, 1155, 1063, 750, 706, 602, 526 cm$^{-1}$; $^1$H NMR (300 MHz, CDCl$_3$) δ: 0.92–1.08(1H,m), 1.39–1.56(1H,m), 1.58–1.74(2H,m), 2.18–2.42(3H,m), 2.53(1H,dt,J=2.4, 11.0), 2.91(1H,d,J=12.0), 3.00(1H,d,J=12.0), 3.51(1H,d,J=10.8), 7.10–7.18(2H,m), 7.21–7.33(8H,m).

EXAMPLE 24

2,4,5,7-Tetraaza-3-methyl-7-(3-(3-diphenylmethyl)piperidyl)propyl)tricyclo[7.4.0.0<2,6>]trideca-1(13),3,5,9(10),11-pentaene-8-one (24)

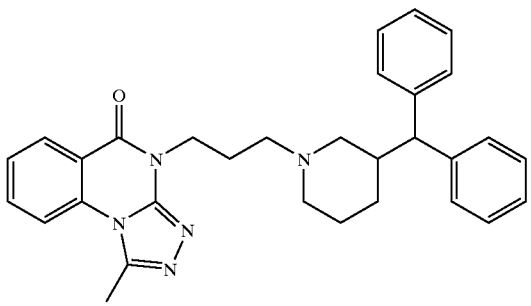

(24)

3-(diphenylmethyl)piperidine (80 mg), 2,4,5,7-tetraaza-7-(3-chloropropyl)-3-methyltricyclo[7.4.0.0<2,6>]trideca-1(13),3,5,9(10),11-pentaene-8-one (90 potassium iodide (54 mg) and potassium carbonate (140 mg) were added to acetonitrile (4 ml) and the mixture was stirred at 80° C. for 46 hours. To the reaction solution, aqueous saturated sodium hydrogen carbonate solution was added and the mixture was extracted once with ethyl acetate, followed by drying the organic layer over anhydrous sodium sulfate. The solvent was removed and the residue was purified by silica gel column chromatography to obtain 60 mg of 2,4,5,7-tetraaza-3-methyl-7-(3-(3-diphenylmethyl)piperidyl)propyl)tricyclo[7.4.0.0<2,6>]trideca-1(13),3,5,9(10),11-pentaene-8-one. Yield: 38%.

IR (KBr): 3026, 2941, 2772, 1681, 1573, 1493, 1443, 758, 705 cm$^{-1}$; $^1$H NMR (300 MHz, CDCl$_3$) δ: 8.46(1H,d,J=8.0), 7.84(2H,dt,J=13.7,8.2), 7.57(1H,t,J=7.4), 7.28–7.09(10H, m), 4.37(2H,t,J=7.1), 3.49(1H,d,J=1.0), 2.94(3H,s), 2.84(1H,m), 2.71(1H,m), 2.51–2.20(3H,m), 2.10–1.75(3H,m), 1.70–1.33(4H,m), 0.92–0.75(1H,m); HR-MS: Calcd.: C$_{31}$H$_{33}$N$_5$O 491.2685 Found: 491.2699.

EXAMPLE 25

N-(3-(4-(Diphenylmethyl)piperazinyl)propyl)(2-aminophenyl)formamide (25)

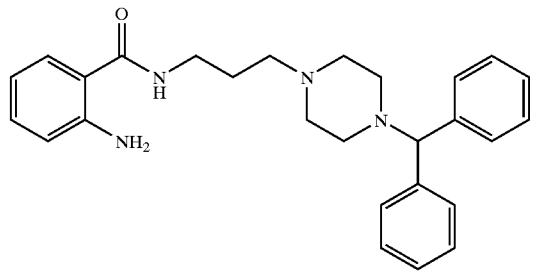

(25)

Isatoic anhydride (1.02 g) and 1-diphenylmethyl-4-(3-aminopropyl)piperazine (2.12 g) were dissolved in 1,4-dioxane (20 ml) and the mixture was stirred at room temperature for 4 hours. 1,4-dioxane was removed and the residue was purified by silica gel column chromatography (ethyl acetate), followed by recrystallization of the resultant from ethyl acetate-hexane to obtain 2.47 g of N-(3-(4-(diphenylmethyl)piperazinyl)propyl)(2-aminophenyl)formamide. Yield: 92%.

MS (EI, m/z): 462 (M$^+$); IR (KBr): 3450, 3348, 2818, 1636, 1528, 1141, 748, 692 cm$^{-1}$; $^1$H NMR (300 MHz, CDCl$_3$) δ: 1.71(2H,m), 2.30–2.68(10H,m), 3.48(2H,q,J=5.8), 4.18(1H,s), 5.58(2H,s), 6.70–7.55(14H,m), 8.22(1H, br).

EXAMPLE 26

2,4,5,7-Tetraaza-3-methyl-7-(3-(4-diphenylmethyl)piperazinyl)propyl)tricyclo[7.4.0.0<2,6>]trideca-1(13),3,5,9(10),11-pentaene-8-one (26)

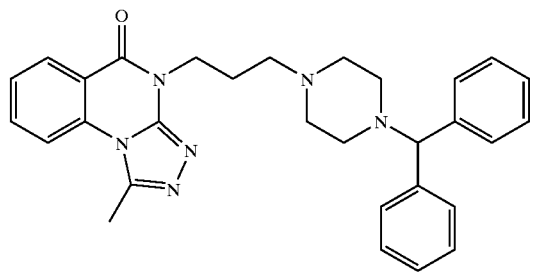

(26)

N-(3-(4-(diphenylmethyl)piperazinyl)propyl(2-aminophenyl)formamide (2.29 g), sodium hydroxide (380 mg) and carbon disulfide (0.7 ml) were added to ethanol (10 ml). The mixture was stirred at room temperature for 2 hours and then heated to reflux for 4 hours. Dilute hydrochloric acid was added to the reaction solution and the precipitates were recovered by filtration. 2.28 g of aliquot thereof was added to ethanol (20 ml) and hydrazine hydrate (14 ml), and the mixture was heated to reflux for 3 hours. Water was added to the reaction solution and the mixture was extracted 3 times with ethyl acetate, followed by drying the organic layers over anhydrous sodium sulfate. After removing the solvent, xylene (30 ml) and ortho-triethyl acetate (5.4 ml) were added to the residue and the mixture was heated to reflux for 4 hours. The reaction solution was concentrated and the residue was recrystallized from ethyl acetate-hexane to obtain 1.6 g of 2,4,5,7-tetraaza-3-methyl-7-(3-(4-diphenylmethyl)piperazinyl)propyl)tricyclo[7.4.0.0<2,6>]trideca-1(13),3,5,9(10),11-pentaene-8-one. Yield: 66%.

m.p.: 168–173° C. IR (KBr): 2954, 2816, 1680, 1663, 1574, 1493, 1284, 1151, 760, 706 cm$^{-1}$; $^1$H NMR (300 MHz, CDCl$_3$) δ: 1.88(2H,quint,J=7.0), 1.94–2.35(8H,m), 2.37(2H,t,J=6.7), 3.34(3H,s), 4.06(1H,s), 4.23(1H,t,J=7.0), 7.16(2H,t,J=7.4), 7.26(4H,t,J=7.6), 7.35(4H,d,J=7.4), 7.59 (1H,t,J=7.6), 7.94(1H,dt,J=7.4,1.8), 8.23(1H,dd,J=7.9,1.2), 8.06(1H,d,J=8.5); HR-MS: Calcd.: C$_{31}$H$_{34}$N$_6$O$_2$ 492.2638 Found: 492.2677.

EXAMPLE 27

2,4,5,7-Tetraaza-3-ethyl-7-(3-(4-diphenylmethyl) piperazinyl)propyl)tricyclo[7.4.0.0<2,6>]trideca-1 (13),3,5,9(10),11-pentaene-8-one (27)

(27)

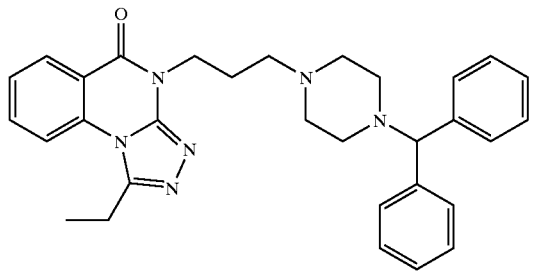

N-(3-(4-(diphenylmethyl)piperazinyl)propyl)(2-aminophenyl)formamide (4.50 g), sodium hydroxide (660 mg) and carbon disulfide (3 ml) were added to ethanol (30 ml). The mixture was stirred at room temperature for 2 hours and heated to reflux for 4 hours. Water was added to the reaction solution and the precipitates were recovered by filtration. 1.67 g of aliquot of the precipitates was added to ethanol (18 ml) and hydrazine hydrate (7 ml), and the mixture was heated to reflux for 5 hours, followed by concentrating the reaction mixture. To 970 mg aliquot thereof, n-butanol (20 ml) and ortho-triethyl acetate (3 ml) were added and the mixture was stirred at 110° C. for 5 hours. The solvent was removed and the residue was purified by silica gel column chromatography (ethyl acetate:ethanol= 12:1) to obtain 736 mg of 2,4,5,7-tetraaza-3-ethyl-7-(3-(4-diphenylmethyl)piperazinyl)propyl)tricyclo[7.4.0.0<2,6>] trideca-1(13),3,5,9(10),11-pentaene-8-one. Yield: 70%.

m.p.: 199–201° C. IR (KBr): 2937, 2807, 1675, 15691489, 1286, 1155, 760, 708 cm$^{-1}$; $^1$H NMR (300 MHz, CDCl$_3$); δ: 1.55(3H,t,7.2), 2.41(2H,quint,J=7.2), 3.23(2H,t, J=7.4), 4.09(1H,s), 4.42(2H,t,J=7.2), 7.:10–7.41(10H,m), 7.46–7.77(1H,m), 7.73–7.88(2H,m), 8.43(1H,d,J=8.0), HR-MS: Calcd.: C$_{31}$H$_{34}$N$_6$O 506.2794 Found: 506.2776.

EXAMPLE 28

2,4,5,7-Tetraaza-3-propyl-7-(3-(4-diphenylmethyl) piperazinyl)propyl)tricyclo[7.4.0.0<2,6>]trideca-1 (13),3,5,9(10),11-pentaene-8-one (28)

(28)

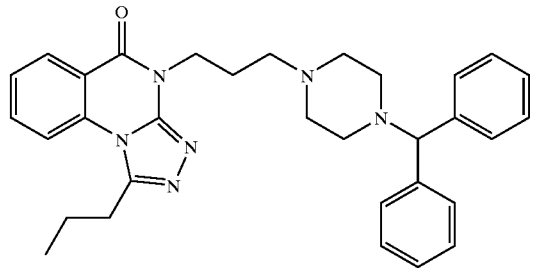

N-(3-(4-(diphenylmethyl)piperazyl)propyl)(2-aminophenyl)formamide (4.5 g) was dissolved in ethanol, and sodium hydroxide (660 mg) and carbon disulfide (3 ml) were added, followed by heating the mixture to reflux for 4 hours. Water was added to the reaction solution and the precipitates were recovered by filtration. 1.67 g of aliquot of the precipitates was dissolved in ethanol (18 ml) and hydrazine hydrate (7 ml) was added to the mixture. The mixture was heated to reflux for 5 hours and the resultant was concentrated. To 627 mg aliquot thereof, n-butanol (15 ml) and ortho-triethyl acetate (2 ml) were added and the mixture was stirred at 110° C. for 7 hours. The solvent was removed and the residue was purified by silica gel column chromatography (ethyl acetate:ethanol=13:1) to obtain 482 mg of 2,4,5,7-tetraaza-3-propyl-7-(3-(4-diphenylmethyl) piperazinyl)propyl)tricyclo[7.4.0.0<2,6>]trideca-1(13),3,5, 9(10),11-pentaene-8-one. Yield: 69%.

m.p.: 150–152° C. IR (KBr): 2967, 2803, 1680, 1568, 1489, 1451, 1283, 153, 761, 710 cm$^{-1}$; $^1$H NMR (300 MHz, CDCl$_3$) δ: 1.14(3H,t,J=7.1), 1.91–2.11(6H,m), 2.0–2.6(8H, m), 2.51(2H,t,J=7.2), 3.17(2H,t,J=7.7), 4.07(1H,s), 4.42(2H, t,J=7.2), 7.10–7.38(10H,m), 7.54(1H,t,J=8.0), 7.77–7.84 (2H,m), 8.43(1H,d,J=8.0); HR-MS: Calcd.: C$_{32}$H$_{36}$N$_6$O 520.2950 Found: 520.2957.

EXAMPLE 29

N-(3-(4-Indole-3-ylpiperidyl)ethyl)(2-aminophenyl) formamide (29)

(29)

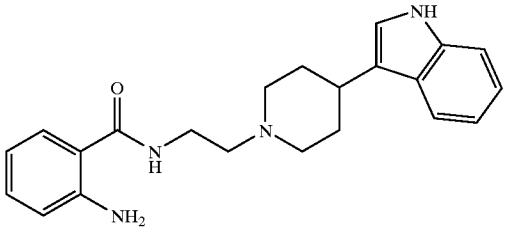

Isatoic anhydride (309 mg) and amine (494 mg) were dissolved in 1,4-dioxane (5 ml) and the mixture was stirred at room temperature for 4 hours. After removing 1,4- dioxane, the residue was purified by silica gel column chromatography (ethyl acetate) to obtain 656 mg of N-(3-(4-indole-3-ylpiperidyl)ethyl)(2-aminophenyl)formamide. Yield: 96%.

MS (EI, m/z): 462 (M+); IR (KBr): 3450, 3348, 2818, 1636, 1528, 1141, 748, 692 cm$^{-1}$; $^1$H NMR (300 MHz, CDCl$_3$) δ: 1.71(2H,m), 2.30–2.68(10H,m), 3.48(2H,q,J=5.8), 4.18(1H,s), 5.58(2H,s), 6.70–7.55(14H,m), 8.22(1H,br).

EXAMPLE 30

3-(2-(4-Indole-3-ylpiperidyl)ethyl)-2-thioxohydroquinazoline-4-one

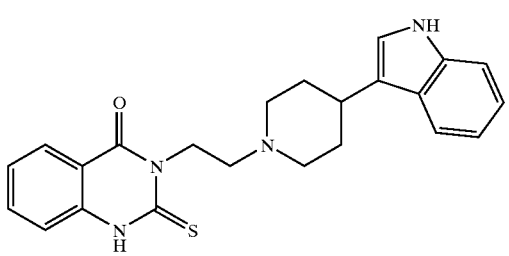

(30)

N-(3-(4-indole-3-ylpiperidyl)ethyl)(2-aminophenyl) formamide (656 mg), sodium hydroxide (196 mg) and carbon disulfide (1 ml) were added to ethanol (5 ml) and the mixture was stirred at room temperature for 1.5 hours and then heated to reflux for 3.5 hours. Water was added to the reaction solution and the precipitates were recovered by filtration, followed by recrystallization from acetone-ethyl acetate to obtain 541 mg of 3-(2-(4-indole-3-ylpiperidyl) ethyl)-2-thioxohydroquinazoline-4-one. Yield: 74%.

MS (EI, m/z): 404 (M+); IR (KBr): 3406, 2928, 1655, 1539, 1129, 758 cm$^{-1}$; $^1$H NMR (300 MHz, CDCl$_3$) δ: 1.6–3.5(11H,m), 4.62(2H,q,J=6.6), 6.8–8.1(10H,m).

EXAMPLE 31

2,4,5,7-Tetraaza-7-(2-(4-indole-3-ylpiperidyl)ethyl)-3-methyltricyclo[7.4.0.0<2,6>]trideca-1(13),3,5,9(10),11-pentaene-8-one (31)

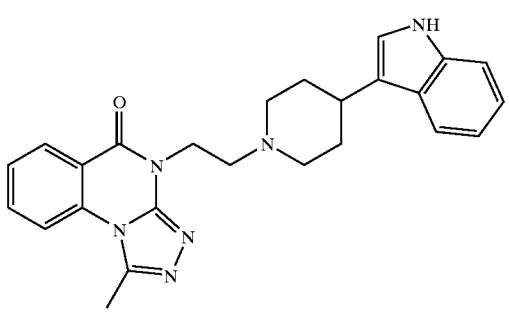

(31)

3-(2-(4-indole-3-ylpiperidyl)ethyl)-2-thioxohydroquinazoline-4-one (541 mg) was added to ethanol (6 ml) and hydrazine hydrate (4 ml), and the mixture was heated to reflux for 2.5 hours. Water was added to the reaction solution and the mixture was extracted 3 times with ethyl acetate. Organic layers were combined and dried over anhydrous sodium sulfate. Ethyl acetate was removed and xylene (10 ml) and ortho-triethyl acetate (318 mg) were added, followed by heating the mixture to reflux for 5 hours. The reaction solution was concentrated and the residue was washed with ethanol to obtain 249 mg of 2,4,5,7-tetraaza-7-(2-(4-indole-3-ylpiperidyl)ethyl)-3-methyltricyclo [7.4.0.0<2,6>]trideca-1(13),3,5,9(10),11-pentaene-8-one. Yield: 44%.

MS (EI, m/z): 426 (M+); IR (KBr): 2942, 2814, 1669, 1615, 1599, 1495, 1338, 706 cm$^{-1}$; $^1$H NMR (300 MHz, CDCl$_3$); δ: 1.62(2H,m), 1.91(2H,m), 2.20(3H,m), 2.75(2H, m), 2.87(3H,s), 3.07(2H,m), 4.35(2H,m), 6.93(1H,m), 7.05 (2H,m), 7.50(1H,d,7.8), 7.31(1H,d,J=7.8), 7.62(1H,t,J=7.6), 7.93(1H,t,J=7.2), 8.07(1H,d,J=7.4), 10.74(1H,s).

EXAMPLE 32

6-Methoxy-3-(3-(4-(diphenylmethyl)piperazinyl) propyl)-2-thioxohydroquinazoline-4-one (32)

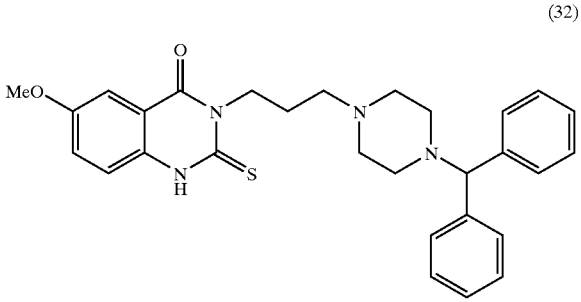

(32)

5-methoxyanthranilic acid (1.1 g) and 1-diphenylmethyl-4-(3-aminopropyl)piperazine (2.2 g) were dissolved in dimethylformamide, and PyBop (3.1 g) and N-methylmorpholine (0.67 ml) were added, followed by stirring the mixture overnight at room temperature. Dimethylformamide was removed and the residue was extracted with dichloromethane. Organic layers were combined and dried over anhydrous sodium sulfate. After removing dichloromethane, the residue was crudely purified by Chromatorex® column chromatography (ethyl acetate) for amines, and sodium hydroxide (250 mg), carbon disulfide (1.5 ml) and ethanol (25 ml) were added, followed by stirring the mixture at 60° C. for 4 hours. Then carbon disulfide (0.5 ml) was added and the mixture was stirred overnight at room temperature. Water was added to the reaction mixture and precipitates were recovered by filtration to obtain 2.3 g of 6-methoxy-3-(3-(4-(diphenylmethyl) piperazinyl)propyl)-2-thioxohydroquinazoline-4-one. Yield: 70%.

m.p.: 209–211° C. IR (KBr): 3244, 2933, 2813, 1650, 1536, 1496, 1154, 701 cm$^{-1}$; $^1$H NMR (300 MHz, CDCl$_3$) δ: 2.04(2H,quint,J=7.4), 2.1–2.65(8H,m), 2.51(2H,t,J=7.2), 3.86(3H,s), 4.12(1H,s), 4.57(2H,t,J=7.2), 7.00–7.40(12H, m), 7.49(1H,d,2.7).

EXAMPLE 33

2,4,5,7-Tetraaza-3-methyl-11-methoxy-7-(3-(4-diphenylmethyl)piperazinyl)propyl)tricyclo[7.4.0.0<2,6>]trideca-1(13),3,5,9(10),11-pentaene-8-one (33)

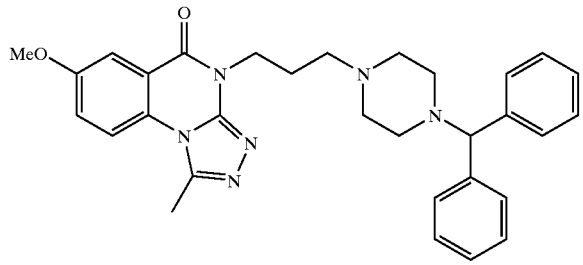

(33)

6-methoxy-3-(3-(4-(diphenylmethyl)piperazinyl)propyl)-2-thioxohydroquinazoline-4-one (1.0 g) was added to ethanol (10 ml) and hydrazine hydrate (8 ml) and the mixture was stirred at 80 to 100° C. for 6 hours. Ethanol and hydrazine were removed, and n-butanol (15 ml) and ortho-triethyl acetate (2 ml) were added to the residue, followed by stirring the mixture at 110° C. for 3 hours. The solvent was removed and the residue was purified by silica gel column chromatography (ethyl acetate:ethanol=8:1) to obtain 770 mg of 2,4,5,7-tetraaza-3-methyl-11-methoxy-7-(3-(4-diphenylmethyl)piperazinyl)propyl)tricyclo[7.4.0.0<2,6>]trideca-1(13),3,5,9(10),11-pentaene-8-one. Yield: 74%.

m.p.: 194–196° C. IR (KBr): 2949, 2812, 1675, 1571, 1498, 1276, 1146, 756, 706 cm$^{-1}$; $^1$H NMR (300 MHz, CDCl$_3$) δ: 2.04(2H,quint,J=7.4), 2.0–2.60(8H,m), 2.51(2H, t,J=7.2), 2.88(3H,s), 3.93(3H,s), 4.10(1H,s), 4.42(2H,t,J= 7.4), 7.10–7.52(11H,m), 7.78(1H,d,J=9.1), 7.84(1H,d,J= 3.1); HR-MS: Calcd.: C$_{31}$H$_{34}$N$_6$O$_2$ 552.2743 Found: 552.2766.

EXAMPLE 34

6,7-Dimethoxy-3-(3-(4-(diphenylmethyl)piperazinyl)propyl-2-thioxohydroquinazoline-4-one (34)

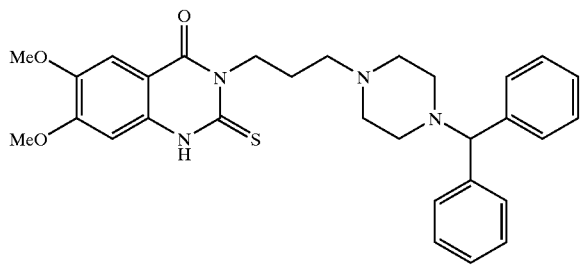

(34)

4,5-dimethoxyanthranilic acid (1.0 g) and 1-diphenylmethyl-4-(3-aminopropyl)piperazine (2.0 g) were dissolved in dimethylformamide, and PyBop (2.9 g) and N-methylmorpholine (0.67 ml) were added, followed by stirring the mixture overnight at room temperature. Dimethylformamide was removed and the residue was extracted with dichloromethane. Organic layers were combined and dried over anhydrous sodium sulfate. After removing dichloromethane, the residue was crudely purified by Chromatorex® column chromatography (ethyl acetate) for amines, and sodium hydroxide (388 mg), carbon disulfide (3 ml) and ethanol (20 ml) were added, followed by stirring the mixture at 70° C. for 3 hours. Water was added to the reaction mixture and the precipitates were recovered by filtration to obtain 2.5 g of 6,7-dimethoxy-3-(3-(4-(diphenylmethyl)piperazinyl)propyl)-2-thioxohydroquinazoline-4-one. Yield: 89%.

m.p.: 249–251° C. IR (KBr): 3118, 2957, 2811, 1684, 1547, 1508, 1284, 1131, 758 cm$^{-1}$; $^1$H NMR (300 MHz, CDCl$_3$) δ: 1.99(2H,quint,J=7.7), 2.19–2.65(8H,m), 2.50(2H, t,J=6.8) 3.93(3H,s), 3.94(3H,s), 4.13(1H,s), 4.55(2H,t,J= 7.4), 6.54(1H,s), 7.13–7.40(11H,m), 7.43(1H,s).

EXAMPLE 35

2,4,5,7-Tetraaza-3-methyl-11,12-dimethoxy-7-(3-(4-diphenylmethyl)piperazinyl)propyl)tricyclo[7.4.0.0<2,6>]trideca-1(1.3),3,5,9(10),11-pentaene-8-one (35)

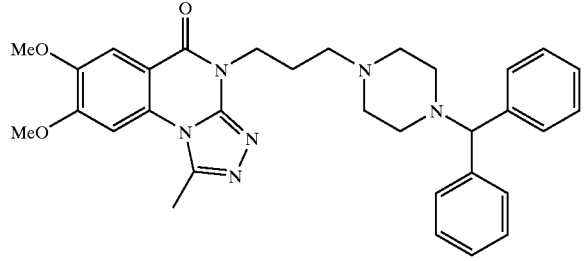

(35)

6,7-dimethoxy-3-(3-(4-(diphenylmethyl)piperazinyl)propyl-2-thioxohydroquinazoline-4-one (1.0 g) was added to ethanol (14 ml) and hydrazine hydrate (7.5 ml), and the mixture was stirred at 90 to 110° C. for 10 hours. Ethanol and hydrazine were removed, and n-butanol (15 ml) and ortho-triethyl acetate (2 ml) were added to the residue, followed by stirring the mixture at 110° C. for 3 hours. After removing n-butanol, the residue was purified by silica gel column chromatography (ethyl acetate:ethanol=7:1) to obtain 780 mg of 2,4,5,7-tetraaza-3-methyl-11,12-dimethoxy-7-(3-(4-diphenylmethyl)piperazinyl)propyl)tricyclo[7.4.0.0<2,6>]trideca-1(13),3,5,9(10),11-pentaene-8-one. Yield: 75%.

m.p.: 184–186° C. IR (KBr): 2958, 2813, 1669, 1618, 1571, 1506, 1263, 1146, 1014, 760, 708 cm$^{-1}$; $^1$H NMR (300 MHz, CDCl$_3$) δ: 2.04(2H,quint,J=7.2), 2.10–2.55(8H,m), 2.51(2H,t,J=7.0), 2.93(3H,s), 4.00(3H,s), 4.06(3H,s), 4.11 (1H,s), 4.40(2H,t,J=7.4), 7.11–7.40(11H,m), 7.76(1H,s); HR-MS: Calcd.: C$_{32}$H$_{36}$N$_6$O$_3$ 552.2849 Found: 552.2822.

EXAMPLE 36

N-(3-(4-(Diphenylmethylpiperazinyl)propyl(3-chloro-6-aminophenyl)formamide (36)

(36)

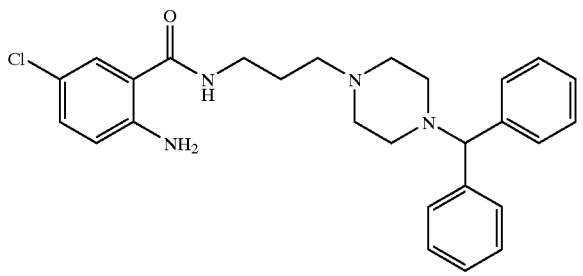

5-chloroisatoic anhydride (2.0 g) and 1-diphenylmethyl-4-(3-aminopropyl)piperazine (3.3 g) were dissolved in tetrahydrofuran (110 ml), and the mixture was stirred at room temperature for 7 hours. After removing tetrahydrofuran, the residue was purified by silica gel column chromatography (ethyl acetate) and then recrystallized from ether-hexane to obtain 4.46 g of N-(3-(4-(diphenylmethylpiperazinyl)propyl (3-chloro-6-aminophenyl)formamide. Yield: 95%.

m.p.: 142–144° C. MS (EI, m/z): 462 (M$^+$); IR (KBr): 3478, 3355, 3285, 2952, 2803, 1624, 1539, 1147, 753, 705 cm$^{-1}$; $^1$H NMR (300 MHz, CDCl$_3$) δ: 1.73(2H,m), 2.2–2.8 (8H,m), 2.58(2H,t,J=5.8), 3.50(2H,q,J=5.8), 4.31(1H,s), 5.65(2H,s), 7.27–7.13(8H,m), 7.40–7.43(5H,m), 8.74(1H,s).

EXAMPLE 37

6-Chloro-3-(3-(4-(diphenylmethyl)piperazinyl) propyl)-2-thioxohydroquinazoline-4-one (37)

(37)

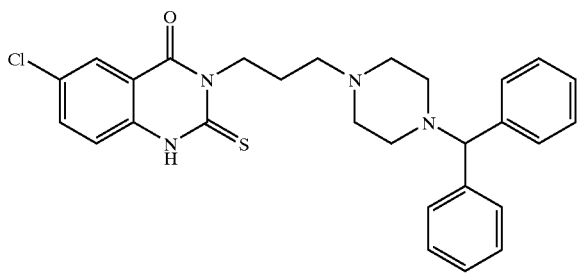

N-(3-(4-(diphenylmethylpiperazinyl)propyl)(3-chloro-6-aminophenyl)formamide (3.10 g), sodium hydroxide (460 mg) and carbon disulfide (2 ml) were added to ethanol (22 ml) and the mixture was stirred at 65° C. for 9 hours. Then carbon disulfide (2 ml) was added and the mixture was stirred overnight at room temperature. Water was added to the reaction mixture and the precipitates were recovered by filtration to obtain 2.83 g of 6-chloro-3-(3-(4-(diphenylmethyl)piperazinyl)propyl)-2-thioxohydroquinazoline-4-one. Yield: 84%.

m.p.: 221–223° C. MS (EI, m/z): 504 (M$^+$); IR (KBr): 3289, 2956, 1659, 1521, 1335, 1156, 705 cm$^{-1}$; $^1$H NMR (300 MHz, CDCl$_3$) δ: 2.01(2H,quint,J=7.4), 2.1–2.7(8H,m), 2.52(2H,t,J=7.4), 4.11(1H,s), 4.54(2H,t,J=7.4), 7.13(1H,d, J=8.5), 7.13–7.40(11H,m), 7.56(1H,dd,J=8.5,2.5), 8.07(1H, d,J=2.5).

EXAMPLE 38

2,4,5,7-Tetraaza-3-methyl-11-chloro-7-(3-(4-diphenylmethyl)piperazinyl)propyl)tricyclo [7.4.0.0<2,6>]trideca-1(13),3,5,9(10),11-pentaene-8-one (38)

(38)

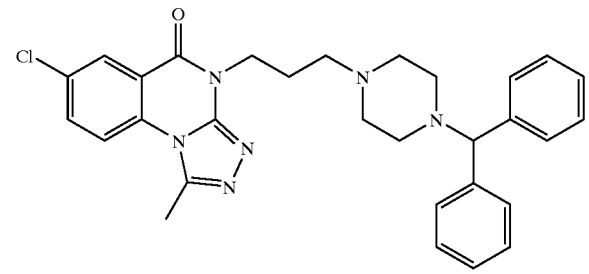

6-Chloro-3-(3-(4-(diphenylmethyl)piperazinyl)propyl)-2-thioxohydroquinazoline-4-one (1.47 g) was added to ethanol (18 ml) and hydrazine hydrate (7 ml) and the mixture was stirred at 100 to 110° C. for 4 hours. Ethanol and hydrazine were removed, and n-butanol (30 ml) and ortho-triethyl acetate (3 ml) were added to the residue, followed by stirring the mixture at 110° C. for 3 hours. After removing n-butanol, the residue was purified by silica gel column chromatography (ethyl acetate:ethanol=6:1) to obtain 1.48 g of 2,4,5,7-tetraaza-3-methyl-11-chloro-7-(3-(4-diphenylmethyl) piperazinyl)propyl)tricyclo[7.4.0.0<2,6>]trideca-1(13),3,5, 9(10),11-pentaene-8-one. Yield: 96%.

m.p.: 116–118° C. IR (KBr): 2950, 2815, 1693, 1603, 1576, 1491, 1454, 1152, 763, 710 cm$^{-1}$; $^1$H NMR (300 MHz, CDCl$_3$) δ: 2.03(2H,m), 2.1–2.6(8H,m), 2.50(2H,t,J= 7.7), 2.89(3H,s), 4.09(1H,s), 4.41(2H,t,J=7.7), 7.13–7.36 (10H,m), 7.77(2H,s), 8.39(1H,d,J=2.0), HR-MS: Calcd.: C$_{30}$H$_{31}$ClN$_6$O 526.2248 Found: 526.2252; Elementary Analysis: C$_{30}$H$_{31}$ClN$_6$O/0.5H$_2$O: Calcd.: C, 67.21%, H, 6.01%, N, 15.68%, C, 16.61% Found: C, 67.24%, H, 6.04%, N, 15.68%, C, 16.58%.

EXAMPLE 39

6-Hydroxy-3-(3-(4-(diphenylmethyl)piperazinyl) propyl)-2-thioxohydroquinazoline-4-one (39)

(39)

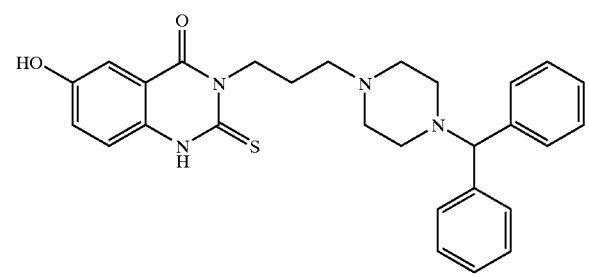

5-hydroxyanthranilic acid (701 mg) and 1-diphenylmethyl-4-(3-aminopropyl)piperazine (1.7 g) were dissolved in dimethylformamide, and PyBop (2.61 g) and N-methylmorpholine (0.74 ml) were added to the mixture. The mixture was stirred overnight at room temperature, and PyBop (1.2 g) and N-methylmorpholine (0.4 ml) were further added, followed by stirring the mixture overnight at room temperature. Dimethylformamide was removed and the residue was extracted with dichloromethane. Organic layers were combined and dried over anhydrous sodium sulfate. After removing dichloromethane, the residue was crudely purified by Chromatorex® column chromatography (ethyl acetate) for amines, and sodium hydroxide (200 mg), carbon disulfide (2 ml) and ethanol (15 ml) were added, followed by stirring the mixture at 50° C. for 5 hours. Water was added to the reaction mixture and the mixture was extracted 3 times with dichloromethane. Organic layers were combined and dried over anhydrous sodium sulfate. Dichloromethane was removed and the residue was purified by silica gel column chromatography (dichloromethane:ethyl acetate=1:2) to obtain 1.10 g of 6-hydroxy-3-(3-(4-(diphenylmethyl)piperazinyl)propyl)-2-thioxohydroquinazoline-4-one.

m.p.: 238–240° C. MS (EI, m/z): 486 (M$^+$); IR (KBr): 3202, 3058, 2957, 2814, 1685, 1520, 1451, 1249, 1151, 752, 705 cm$^{-1}$; $^1$H NMR (300 MHz, CDCl$_3$) δ: 1.95(2H,m), 2.2–3.0(10H,m), 4.13(1H,s), 4.44(2H,brt), 7.06–7.40(11H, m), 6.98(1H,d.7.0).

EXAMPLE 40

2,4,5,7-Tetraaza-3-methyl-11-hydroxy-7-(3-(4-diphenylmethyl)piperazinyl)propyl)tricyclo[7.4.0.0<2,6>]trideca-1(13),3,5,9(10),11-pentaene-8-one (40)

(40)

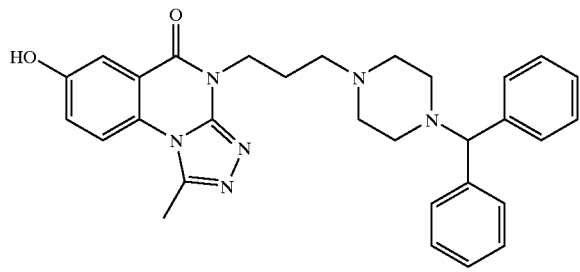

6-hydroxy-3-(3-(4-(diphenylmethyl)piperazinyl)propyl)-2-thioxohydroquinazoline-4-one (586 mg) was added to ethanol (10 ml) and hydrazine hydrate (5 ml), and the mixture was stirred at 80° C. for 5 hours. Ethanol and hydrazine were removed, and n-butanol (15 ml) and orthotriethyl acetate (2 ml) were added to the residue, followed by stirring the mixture at 110° C. for 3 hours. After removing n-butanol, the residue was purified by silica gel column chromatography (dichloromethane:ethanol=10:1) to obtain 396 mg of 2,4,5,7-tetraaza-3-methyl-11-hydroxy-7-(3-(4-diphenylmethyl)piperazinyl)propyl)tricyclo[7.4.0.0<2,6>]trideca-1(13),3,5,9(10),11-pentaene-8-one. Yield: 63%.

m.p.: 225–228° C. IR (KBr): 3420, 2958, 2810, 1678, 1575, 1498, 1450, 1316, 747, 706 cm$^{-1}$; $^1$H NMR (300 MHz, DMSO) δ: 1.84(2H,quint,J=7.0), 1.90–2.40(8H,m), 2.34(2H,t,J=6.3), 2.76(3H,s), 4.03(1H,s), 4.20(2H,t,J=7.2), 7.1–7.35(11H,m), 7.90(1H,d,J=8.8), 7.55(1H,d,J=3.0); HR-MS: Calcd.: C$_{30}$H$_{32}$N$_6$O$_2$ 508.2587 Found: 508.2593.

EXAMPLE 41

2,4,5,7-Tetraaza-3-methyl-11-isopropoxy-7-(3-(4-diphenylmethyl)piperazinyl)propyl)tricyclo[7.4.0.0<2,6>]trideca-1(13),3,5,9(10),11-pentaene-8-one (41)

(41)

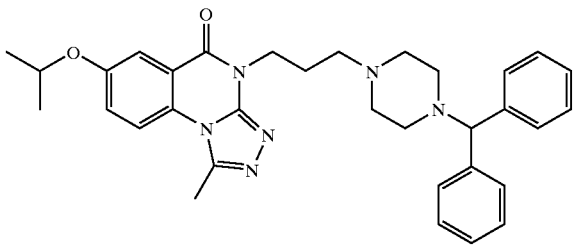

2,4,5,7-tetraaza-3-methyl-11-hydroxy-7-(3-(4-diphenylmethyl)piperazinyl)propyl)tricyclo[7.4.0.0<2,6>]trideca-1(13),3,5,9(10),11-pentaene-8-one (70 mg), potassium carbonate (40 mg) and 2-iodopropane (0.035 ml) were added to dimethylformamide, and the mixture was stirred at 70 to 80° C. for 10 hours. Dimethylformamide was removed and water was added to the residue, followed by extraction of the mixture with dichloromethane. Organic layers were combined and dried over anhydrous sodium sulfate. Dichloromethane was removed and the residue was purified by silica gel column chromatography (dichloromethane:ethanol=14:1) to obtain 74 mg of 2,4,5,7-tetraaza-3-methyl-11-isopropoxy-7-(3-(4-diphenylmethyl)piperazinyl)propyl)tricyclo[7.4.0.0<2,6>]trideca-1(13),3,5,9(10),11-pentaene-8-one. Yield: 99%.

$^1$H NMR (300 MHz, CDCl$_3$) δ: 1.38(6H,d,J=6.0), 2.04 (2H,quint,J=7.0), 2.00–2.60(8H,m), 2.51(2H,t,J=7.2), 2.88 (3H,s), 4.09(1H,s), 4.42(2H,t,J=7.2), 4.70(1H,sep,J=6.0), 7.83(1H,d,J=3.0); HR-MS: Calcd.: C$_{30}$H$_{32}$N$_6$O$_2$ 550.3056 Found: 550.3056.

EXAMPLE 42

N-(3-(4-(Diphenylmethylpiperazinyl)propyl)(2-nitro-6-trifluorophenyl)formamide (42)

(42)

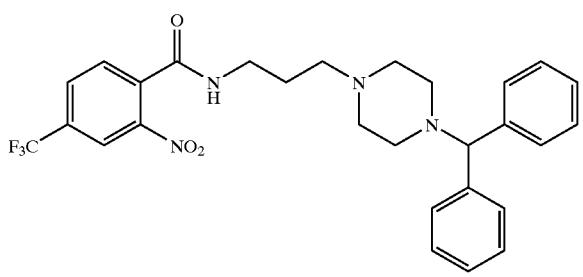

2-nitro-α,α,α-trifluoro-p-toluilic acid (942 mg), 1-diphenylmethyl-4-(3-aminopropyl)piperazine (1.36 g) and PyBop (2.30 g) were dissolved in dimethylformamide, and N-methylmorpholine (0.5 ml) was dropped to the mixture, followed by stirring the mixture at room temperature for 24 hours. Water (5 ml) was added to the reaction mixture and the mixture was extracted 3 times with dichloromethane. Organic layers were combined and dried over anhydrous sodium sulfate. The solvent was removed and the residue was purified by Chromatorex® column chromatography for amines (n-hexane:ethyl acetate 2:1–1:1) to obtain 1.60 g of N-(3-(4-(diphenylmethylpiperazinyl)propyl)(2-nitro-6-trifluorophenyl)formamide. Yield: 76%.

MS (EI, m/z): 526 (M$^+$); $^1$H NMR (300MHz, CDCl$_3$) δ: 1.72–1.80(2H,m), 2.30–2.54(8H,m), 2.57(2H,t,J=5.5), 3.55–3.61(2H,m), 3.76(1H,s), 7.13–7.30(10H,m), 7.67(1H,d,J=8.0), 7.94(1H,dd,J=9.0,1.1), 8.35(1H,d,J=0.82).

EXAMPLE 43

N-(3-(4-(Diphenylmethylpiperazinyl)propyl)(2-amino-4-trifluorophenyl)formamide (43)

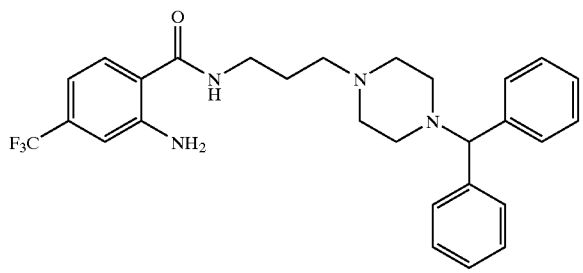

(43)

Under argon atmosphere, N-(3-(4-(diphenylmethylpiperazinyl)propyl)(2-nitro-6-trifluorophenyl)formamide (1.60 g) was dissolved in ethanol (1 ml), and small amounts of concentrated hydrochloric acid (1 ml) and stannous chloride (II) dihydrate (627 mg) were added at 0° C., followed by stirring the mixture at room temperature for 20 hours. The precipitates were dissolved in water-ethanol mixture, and saturated aqueous ammonia was added thereto, followed by extraction of the mixture 3 times with chloroform. Organic layers were combined and dried over anhydrous sodium sulfate. Chloroform was removed and the residue was purified by Chromatorex® column chromatography for amines (n-hexane:ethyl acetate=4:1) to obtain 268 mg of N-(3-(4-(diphenylmethylpiperazinyl)propyl)(2-amino-4-trifluorophenyl)formamide. Yield: 54%.

MS (EI, m/z): 496 (M$^+$); $^1$H NMR (300 MHz, CDCl$_3$) δ: 1.70–1.80(2H,m), 2.22–2.80(8H,m), 2.58(2H,t,J=5.2), 3.48–3.53(2H,m), 4.17(1H,s), 6.83(1H,d,J=8.2), 6.90(1H,s), 7.16–7.30(6H,m), 7.38(4H,d,J=7.1), 7.45(1H,d,J=8.24).

EXAMPLE 44

7-Trifluoromethyl-3-(3-(4-(diphenylmethyl)piperazinyl)propyl)-2-thioxohydroquinazoline-4-one (44)

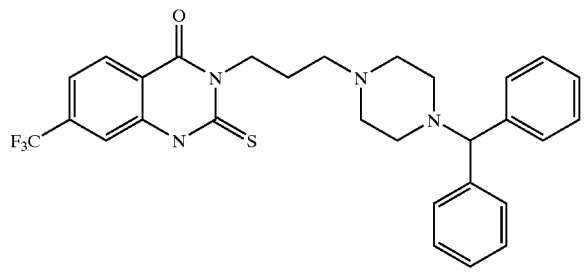

(44)

N-(3-(4-(diphenylmethylpiperazinyl)propyl)(2-amino-4-trifluorophenyl)formamide (268 mg) was dissolved in ethanol (5 ml), and sodium hydroxide (36.8 mg) and carbon disulfide (170 ml) were added thereto, followed by stirring the mixture at 60° C. for 6 hours. Carbon disulfide (5.6 ml) was further added and the mixture was stirred at 80° C. for 14 hours and then at 90° C. for 79 hours. Water (10 ml) was added to the reaction mixture and the mixture was extracted 3 times with dichloromethane. Organic layers were combined and dried over anhydrous sodium sulfate. Dichloromethane was removed and the residue was purified by Chromatorex® column chromatography for amines (n-hexane:ethyl acetate=1:1–2:3–1:2) to obtain 260 mg of 7-trifluoromethyl-3-(3-(4-(diphenylmethyl)piperazinyl)propyl)-2-thioxohydroquinazoline-4-one. Yield: 89%.

MS (EI, m/z): 538 (M$^+$); IR (neat) 2816, 1694, 1637, 1552, 1495, 1446, 1323, 1249, 1173, 1135, 756, 698 cm$^{-1}$; $^1$H NMR (300 MHz, CDCl$_3$) δ: 2.03(2H,t,J=6.9), 2.34(8H, bs), 2.55(2H,t,J=6.6), 4.06(1H,s), 4.57(2H,t,J=6.6), 7.15 (2H,d,J=7.1 Hz), 7.22–7.27(4H,m), 7.37(2H,d,J=6.3), 7.49 (2H,d,J=8.2), 8.22(2H,d,J=8.2).

EXAMPLE 45

2,4,5,7-Tetraaza-3-methyl-12-trifluoromethyl-7-(3-(4-diphenylmethyl)piperazinyl)propyl)tricyclo[7.4.0.0<2,6>]trideca-1(13),3,5,9(10),11-pentaene-8-one (45)

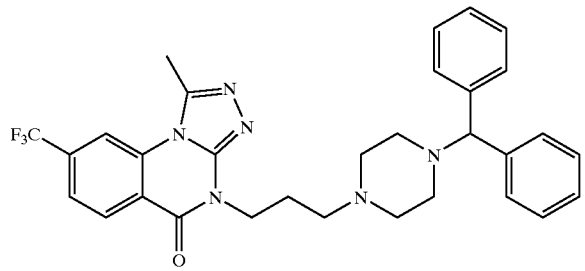

(45)

7-trifluoromethyl-3-(3-(4-(diphenylmethyl)piperazinyl)propyl)-2-thioxohydroquinazoline-4-one (260 mg) was dissolved in ethanol (12 ml) and hydrazine hydrate (2 ml) was added to the mixture, followed by stirring the mixture at 110° C. for 6.5 hours. Ethanol and hydrazine hydrate were removed, and 1-butanol (30 ml) and ortho-triethyl acetate 3 ml were added to the residue, followed by stirring the mixture at 120° C. for 5 hours. The solvent was removed and the residue was purified by silica gel column chromatography (ethyl acetate ethyl acetate:methanol=10:1) to obtain 233 mg of 2,4,5,7-tetraaza-3-methyl-12-trifluoromethyl-7-(3-(4-diphenylmethyl)piperazinyl)propyl)tricyclo [7.4.0.0<2,6>]trideca-1(13),3,5,9(10),11-pentaene-8-one. Yield: 86%. The free compound was dissolved in 5 ml of methanol, and 0.18 ml of hydrochloric acid/methanol (2.5 M) was added at room temperature. The reaction solution was concentrated and the residue was recrystallized from methanol-ether to obtain 81.2 mg of the corresponding hydrochloride. Crystallization Yield: 31%.

m.p.: 154–159.5° C. (hydrochloric acid); MS (free compound, EI, m/z): 560 (M+); IR (free compound, neat); 2960, 2813, 2247, 1684, 1602, 1574, 1484, 1287, 1177, 1142, 909, 733 cm$^{-1}$; $^1$H NMR (free compound, 300 MHz, CDCl$_3$) δ: 2.05(2H,t,J=6.9), 2.38(8H,bs), 2.51(2H,t,J=6.9), 2.94(3H,s), 4.02(1H,s), 4.45(2H,t,J=6.6), 7.16(2H,d,J=7.1), 7.22–7.26(4H,m), 7.34(2H,d,J=7.4 Hz), 7.80(2H,d,J=8.2), 8.10(1H,s), 8.57(2H,d,J=8.5).

EXAMPLE 46

6-Dimethylamino-3-(3-(4-diphenylmethyl)piperazinyl)propyl)-2-thioxohydroquinazoline-4-one (46)

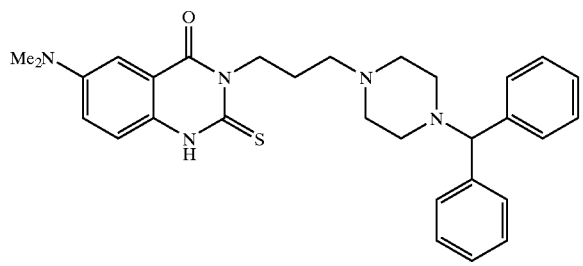

(46)

5-dimethylaminoanthranilic acid (293 mg) and N-diphenylmethyl-N'-aminopropylpiperazine (511 mg) were dissolved in dimethylformamide (10 ml), and Pybop (940 mg) and N-methylmorpholine (170 ml) were added thereto, followed by stirring the mixture overnight at room temperature. Water was added to the reaction solution and the mixture was extracted with dichloromethane. Organic layers were combined and dried over anhydrous sodium sulfate. Dichloromethane was removed and the residue was purified by Chromatorex® column chromatography for amines (hexane:ethyl acetate=3:1). To the obtained product, sodium hydroxide (93 mg), carbon disulfide (1 ml) and ethanol (10 ml) were added and the resulting mixture was stirred at 70° C. for 4 hours. Water was added to the reaction mixture and the resulting mixture was extracted 3 times with dichloromethane. Organic layers were combined and dried over anhydrous sodium sulfate. Dichloromethane was removed and the. residue was purified by silica gel column chromatography (hexane:ethyl acetate=1:1) to obtain 405 mg of 6-dimethylamino-3-(3-(4-(diphenylmethyl)piperazinyl)propyl)-2-thioxohydroquinazoline-4-one. Yield: 69%.

m.p.: 239–242° C. MS (EI, m/z): 513 (M+); IR (KBr): 2956, 2811, 1680, 1533, 1368, 1082, 703 cm$^{-1}$; $^1$H NMR (300 MHz, CDCl$_3$) δ: 1.99(2H,quint,J=7.1), 2.20–2.60(8H,m), 2.50(2H,t,J=7.1), 3.00(6H,s), 4.13(1H,s), 4.57(2H,t,J=8.0), 6.96–7.41(13H,m).

EXAMPLE 47

2,4,5,7-Tetraaza-3-methyl-11-dimethylamino-7-(3-(4-diphenylmethyl)piperazinyl)propyl)tricyclo [7.4.0.0<2,6>]trideca-1(13),3,5,9(10),11-pentaene-8-one (47)

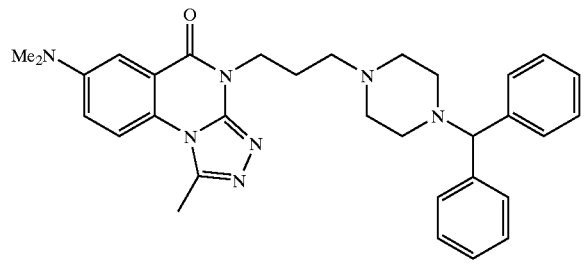

(47)

6-dimethylamino-3-(3-(4-diphenylmethyl)piperazinyl) propyl)-2-thioxohydroquinazoline-4-one (384 mg) was dissolved in ethanol (6 ml) and hydrazine hydrate (5 ml), and the mixture was stirred at 80 to 105° C. for 4 hours. Ethanol and hydrazine were removed, and n-butanol (10 ml) and ortho-ethyl acetate (2 ml) were added to the residue, followed by stirring the mixture at 110° C. for 3 hours. After removing n-butanol, the residue was purified by silica gel column chromatography (ethyl acetate:ethanol=6:1) to obtain 277 mg of 2,4,5,7-tetraaza-3-methyl-11-dimethylamino-7-(3-(4-diphenylmethyl)piperazinyl)propyl) tricyclo[7.4.0.0<2,6>]trideca-1(13),3,5,9(10),11-pentaene-8-one. Yield: 69%.

m.p.: 189–191° C. IR (KBr): 2926, 2807, 2807, 1670, 1567, 1511, 1376, 1150, 749 cm$^{-1}$; $^1$H NMR (300 MHz, CDCl$_3$) δ: 2.17(2H,quint,J=7.4), 2.15–2.62(8H,m), 2.51(2H, t,J=7.2), 2.87(3H,s), 3.07(6H,s), 4.11(1H,s), 4.41(2H,t,J=7.4), 7.08–7.42(11H,m), 7.59(1H,d,J=3.0), 7.71(1H,d,J=9.0); HR-MS: Calcd. C$_{32}$H$_{37}$N$_7$O (M+H)$^+$ 535.3060 Found: 535.3079.

EXAMPLE 48

N-(3-(4-(Diphenylmethylpiperazinyl)ethyl)(2-aminophenyl)formamide (48)

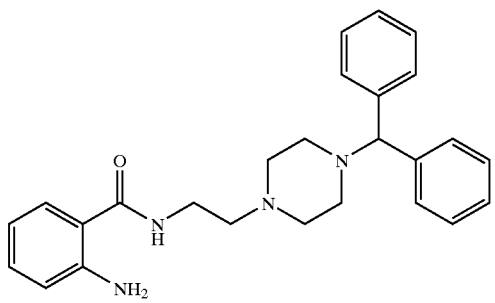

(48)

1-diphenylmethyl-4-(2-aminoethyl)piperazine (1.46 g) and isatoic anhydride (800 mg) were dissolved in tetrahydrofuran (25 ml), and the mixture was stirred overnight at room temperature. Tetrahydrofuran was removed and the residue was purified by silica gel column chromatography (ethyl acetate:hexane=4:1) to obtain 1.67 g of N-(3-(4-(diphenylmethylpiperazinyl)ethyl)(2-aminophenyl) formamide.

MS (EI, m/z): 414 (M$^+$); IR (KBr): 3361, 3291, 2806, 1653, 1619, 1529, 1327, 747, 702 cm$^{-1}$; $^1$H NMR (300 MHz, CDCl$_3$) δ: 2.2–2.6(8H,m), 2.58(2H,t,J=6.0), 3.47(2H,q,J=6.0), 5.51(2H,s), 6.66(1H,t,J=6.8), 7.14–7.31(10H,m), 7.40–7.43(4H,m).

EXAMPLE 49

3-(2-(4-(Diphenylmethyl)piperazinyl)ethyl)-2-thioxohydroquinazoline-4-one (49)

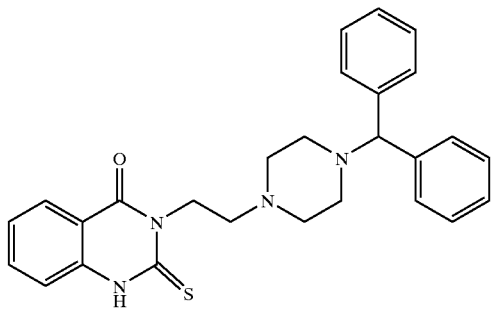

(49)

N-(3-(4-(diphenylmethylpiperazinyl)ethyl)(2-aminophenyl)formamide (1.56 g), sodium hydroxide (180 mg) and carbon disulfide (1 ml) were added to ethanol (15 ml), and the mixture was stirred at 60° C. for 8 hours. Carbon disulfide (2 ml) was added and the mixture was stirred overnight. Water was added to the reaction mixture and the generated precipitates were recovered by filtration to quantitatively obtain 3-(2-(4-(diphenylmethyl)piperazinyl)ethyl)-2-thioxohydroquinazoline-4-one.

m.p.: 198–200° C. MS (EI, m/z): 456 (M$^+$); IR (KBr): 3248, 2958, 2811, 1658, 1534, 1134, 758, 704 cm$^{-1}$; $^1$H NMR (300 MHz, CDCl$_3$) δ: 2.41(4H,brs), 2.66(4H,brs), 2.77(2H,t,J=7.7), 4.20(1H,s), 4.67(2H,t,J=7.7), 7.04(1H,d,J=7.7), 7.13–7.42(11H,m), 7.64(1H,t,J=7.5), 8.11(1H,dd,J=8.0,1.1).

EXAMPLE 50

2,4,5,7-Tetraaza-3-methyl-7-(2-(4-diphenylmethyl)piperazinyl)ethyl)tricyclo[7.4.0.0<2,6>]trideca-1(13),3,5,9(10),11-pentaene-8-one (50)

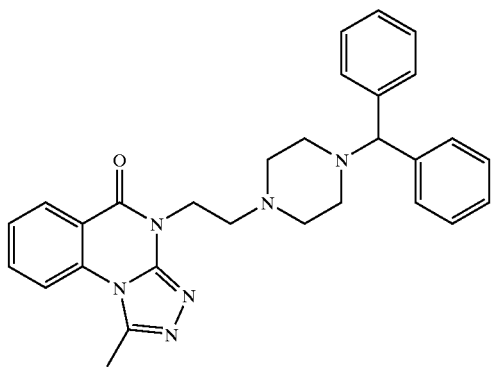

(50)

3-(2-(4-(diphenylmethyl)piperazinyl)ethyl)-2-thioxohydroquinazoline 4-one (1.0 g) was added to ethanol (24 ml) and hydrazine hydrate (7 ml), and the mixture was stirred at 80 to 90° C. for 4 hours. Ethanol and hydrazine were removed, and n-butanol (20 ml) and ortho-triethyl acetate (3.5 ml) were added to the residue, followed by stirring the mixture at 110° C. for 3 hours. After removing n-butanol, the residue was purified by silica gel column chromatography (ethyl acetate:ethanol=14:1) to obtain 701 mg of 2,4,5,7-tetraaza-3-methyl-7-(2-(4-diphenylmethyl)piperazinyl)ethyl)tricyclo[7.4.0.0<2,6>]trideca-1(13),3,5,9(10),11-pentaene-8-one.

m.p.: 217–219° C. IR (KBr): 2941, 2813, 1668, 1571.1493, 1154, 759, 702 cm$^{-1}$; $^1$H NMR (300 MHz, CDCl$_3$) δ: 2.37(4H,brs), 2.63(4H,brs), 2.84(2H,t,J=6.8), 2.93(3H,s), 4.17(1H,s), 4.48(2H,t,J=6.8), 7.10–7.41(10H,m), 7.55(1H,td,J=7.7,1.5), 7.81(1H,td,7.4,1.5), 7.86(1H,t,7.7), 8.43(1H,dd,7.4,1.5); HR-MS: Calcd.: C$_{30}$H$_{32}$N$_6$O$_2$ 478.2481 Found: 478.2502.

EXAMPLE 51

N-(4-Hydroxybutyl)(2-aminophenyl)formamide (51)

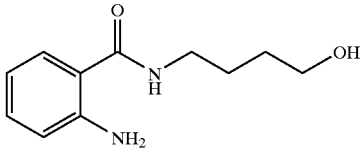

(51)

Isatoic anhydride (4.5 g), 3-aminopropanol (2.66 ml) were added to tetrahydrofuran (70 ml), and the mixture was stirred at room temperature for 4 hours. Tetrahydrofuran was removed and the residue was purified by silica gel column chromatography (ethyl acetate) to obtain 4.7 g of N-(4-hydroxybutyl)(2-aminophenyl)formamide. Yield: 82%.

m.p.: 77–79° C. MS (EI, m/z): 208 (M$^+$); IR (KBr): 3475, 3368, 3289, 2937, 1624, 1547, 1264, 1061, 750 cm$^{-1}$; $^1$H NMR (300 MHz, CDCl$_3$) δ: 1.6–1.8(4H,m), 3.44(2H,q,J=6.4), 3.71(2H,t,J=6.0), 5.49(2H,s), 6.38(1H,s), 6.65(1H,t,J=8.0), 6.67(1H,d,J=8.0), 7.30(1H,dd,J=8.0,1.4), 7.19(1H,td, J=8.2,1.4).

EXAMPLE 52

3-(4-Hydroxybutyl)-2-thioxohydroquinazoline-4-one (52)

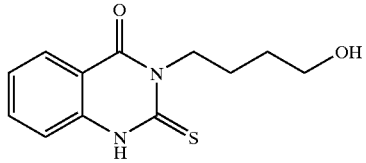

(52)

N-(4-hydroxybutyl)(2-aminophenyl)formamide (4.2 g), sodium hydroxide (1.6 g) and carbon disulfide (4.5 ml) were added to ethanol (30 ml), and the mixture was stirred at 80° C. for 10 hours. Carbon disulfide (2 ml) was further added and the mixture was stirred overnight at room temperature. Water was added to the reaction mixture and the precipitates were recovered by filtration to quantitatively obtain 3-(4-hydroxybutyl)-2-thioxohydroquinazoline-4-one.

m.p.: 175–176° C. MS (EI, m/z): 249((M−H)$^+$); IR (KBr): 3250, 2939, 1650, 1535, 1149, 763 cm$^{-1}$; $^1$H NMR (300 MHz, CDCl$_3$) δ: 1.71(2H,quint,J=6.6), 1.91(2H,quint,J=7.4), 3.75(2H,q,J=6.0), 4.55(2H,t,J=7.7), 7.08(1H,d,J=8.8), 7.32(1H,t,J=7.8), 8.13(1H,d,J=7.4), 9.85(1H,brs).

EXAMPLE 53

2,4,5,7-Tetraaza-7-(4-hydroxybutyl)-3-methyltricyclo[7.4.0.0<2,6>]trideca-1(13),3,5,9(10),11-pentaene-8-one (53)

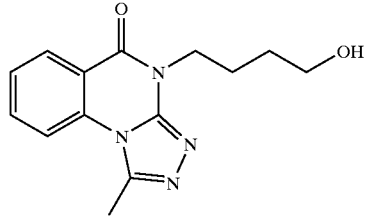

(53)

3-(4-hydroxybutyl)-2-thioxohydroquinazoline-4-one (2.4 g) was added to ethanol (30 ml) and hydrazine hydrate (18 ml), and the mixture was stirred at 80 to 105° C. for 3 hours. Ethanol and hydrazine were removed, and n-butanol (30 ml) and ortho-triethyl acetate (4.3 ml) were added to the residue, followed by stirring the mixture at 110° C. for 3 hours. After removing n-butanol, the residue was purified by silica gel column chromatography (dichloromethane:ethanol=12:1) to obtain 1.5 g of 2,4,5,7-tetraaza-7-(4-hydroxybutyl)-3-methyltricyclo[7.4.0.0<2,6>]trideca-1(13),3,5,9(10),11-pentaene-8-one. Yield: 57.6%.

m.p.: 157–159° C. MS (EI, m/z): 272 (M$^+$); IR (KBr): 3363, 3221, 2953, 1676, 1609, 1495, 1083, 761 cm$^{-1}$; $^1$H NMR (300 MHz, CDCl$_3$) δ: 1.69(2H,quint,J=6.3), 1.98(2H, quint,J=7.4), 2.30(1H,s), 2.94(3H,s), 3.75(2H,q,J=6.0), 4.42 (2H,t,J=7.4), 7.56(1H,t,J=7.2), 7.82(1H,td,J=7.2,1.5), 7.89 (1H,d,J=7.7), 8.45(1H,dd,J=8.0, 1.4).

EXAMPLE 54

2,4,5,7-Tetraaza-7-(4-chlorobutyl)-3-methyltricyclo[7.4.0.0<2,6>]trideca-1(13),3,5,9(10),11-pentaene-8-one (54)

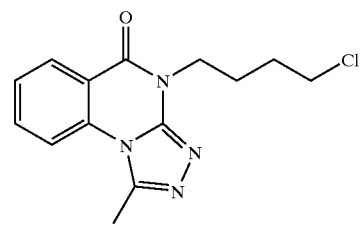

(54)

2,4,5,7-tetraaza-7-(4-hydroxybutyl)-3-methyltricyclo[7.4.0.0<2,6>]trideca-1(13),3,5,9(10),11-pentaene-8-one (1.2 g) was dissolved in dichloromethane (40 ml), and carbon tetrachloride (2 ml) and triphenylphosphine (2.5 g) were added, followed by stirring the mixture overnight at room temperature. Carbon tetrachloride and triphenylphosphine were further added until reaction completed. Dichloromethane was removed and the residue was purified by silica gel column (ethyl acetate:ethanol=10:1) to obtain 1.2 g of 2,4,5,7-tetraaza-7-(4-chlorobutyl)-3-methyltricyclo[7.4.0.0<2,6>]trideca-1(13),3,5,9(10),11-pentaene-8-one.

m.p.: 152–154° C. MS (EI, m/z): 290 (M$^+$); IR (KBr): 2950, 1676, 1567, 1490, 1440, 763, 713 cm$^{-1}$; $^1$H NMR (300 MHz, CDCl$_3$) δ: 1.90(2H,quint,J=6.6), 2.05(2H,quint, J=7.4), 2.95(3H,s), 3.60(2H,q,J=6.6), 4.41(2H,t,J=7.4), 7.57 (1H,t,J=7.8), 7.83(1H,t,J=7.2,1.1), 7.89(1H,d,J=7.6), 8.46 (1H,dd,J=8.0,1.1).

EXAMPLE 55

2,4,5,7-Tetraaza-3-methyl-7-(4-(4-diphenylmethyl)piperazinyl)butyl)tricyclo[7.4.0.0<2,6>]trideca-1(13),3,5,9(10),11-pentaene-8-one (55)

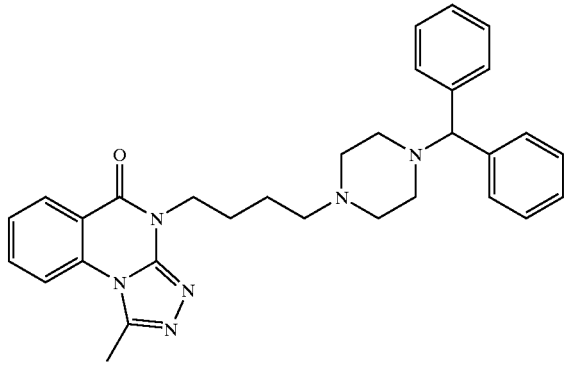

(55)

2,4,5,7-tetraaza-7-(4-chlorobutyl)-3-methyltricyclo[7.4.0.0<2,6>]trideca-1(13),3,5,9(10),11-pentaene-8-one (355 mg), diphenylmethylpiperazine (320 mg) and potassium carbonate (170 mg) were added to dimethylformamide (15 ml) and the mixture was stirred at 70 to 90° C. for 20 hours. Dimethylformamide was removed, and water was added to the residue, followed by extraction of the resultant with dichloromethane. Organic layers were combined and dried over anhydrous sodium sulfate. Dichloromethane was removed and the residue was purified by silica gel column chromatography (ethyl acetate:ethanol=6:1) to obtain 167 mg of 2,4,5,7-tetraaza-3-methyl-7-(4-(4-diphenylmethyl)piperazinyl)butyl)tricyclo[7.4.0.0<2,6>]trideca-1(13),3,5,9 (10),11-pentaene-8-one. Yield: 27%.

m.p.: 157–159° C. IR (KBr): 2941, 2812, 1672, 1571, 1493, 1155, 759, 706 cm$^{-1}$; $^1$H NMR (300 MHz, CDCl$_3$) δ: 1.88(2H,quint,J=6.9), 2.38(2H,t,J=7.4), 2.2–2.6(8H,m), 2.93 (3H,s), 4.18(1H,s), 4.37(2H,t,J=7.4), 7.10–7.43(10H,m), 8.43(1H,dd,J=8.0,1.1), 7.89(1H,d,J=7.6), 7.81(1H,t,J=7.2), 7.55(1H,t,J=6.9), HR-MS: Calcd.: C$_{31}$H$_{34}$N$_6$O$_2$ 506.2794 Found: 506.2765.

EXAMPLE 56

2,4,5,7-Tetraaza-3-methyl-7-(4-(4-diphenylmethyl)piperidyl)butyl)tricyclo[7.4.0.0<2,6>]trideca-1(13),3,5,9(10),11-pentaene-8-one (56)

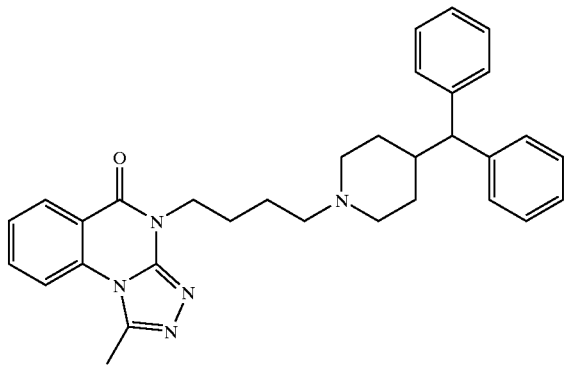

(56)

4-diphenylmethylpiperidine hydrochloride (327 mg), 2,4,5,7-tetraaza-3-methyl-7-(4-(4-diphenylmethyl)piperazinyl)butyl)tricyclo[7.4.0.0<2,6>]trideca-1(13),3,5,9(10),11-pentaene-8-one (462 mg), potassium carbonate (548 mg) and acetonitrile (6 ml) were added and the mixture was stirred at 110° C. for 82.5 hours. The reaction mixture was filtered and the filtrate was concentrated, followed by purifying the residue by silica gel column chromatography (ethyl acetate-methanol:chloroform=1:10) to obtain 433 mg of 2,4,5,7-tetraaza-3-methyl-7-(4-(4-diphenylmethyl)piperidyl)butyl)tricyclo[7.4.0.0<2,6>]trideca-1(13),3,5,9(10),11-pentaene-8-one. Yield: 75%.

Then the free compound was dissolved in methanol (30 ml) and hydrochloric acid/methanol (2.5 M, 0.2 ml) was added thereto at room temperature. The solvent was concentrated and the residue was recrystallized from methanol/ether to obtain 322 mg of the corresponding hydrochloride. Crystallization Yield: 69%.

m.p.: 166.5–180.0° C. (hydrochloride); MS (EI, m/z): 505 (M$^+$); IR (neat): 2945, 1679, 1614, 1599, 1573, 1537, 1493, 1443, 909, 731 cm$^{-1}$; $^1$H NMR (300 MHz, CDCl$_3$) δ: 1.59(4H,bs), 1.76(2H,bs), 1.86–1.97(2H,m), 2.20(2H,bs), 2.67(2H,bs), 2.94(3H,s), 3.09(2H,bs), 3.54(2H,d,J=11.3), 4.37(2H,t,J=7.1), 7.12–7.27(10H,m), 7.56(1H,dt,J=8.0,1.4), 7.82(1H,dt,J=7.5,1.6), 7.88(1H,d,J=7.7), 8.43(1H,dd,J=8.0,1.4).

EXAMPLE 57

4-(N-(2-Formylphenyl)carbamoyl)butanoic Acid (57)

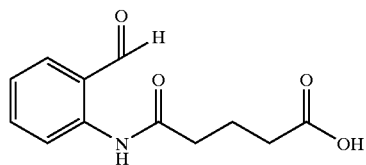
(57)

2-aminobenzaldehyde (2.87 g) and glutaric anhydride (3.26 g) were dissolved in benzene (60 ml) and the mixture was heated to reflux for 10.5 hours. Benzene was removed and the residue was purified by silica gel column chromatography (ethyl acetate:hexane=1:1- ethyl acetate) to obtain 5.12 g of 4-(N-(2-formylphenyl)carbamoyl)butanoic acid. Yield: 93%.

MS (EI, m/z): 235 (M$^+$); IR (neat): 2958, 2255, 1731, 1567, 1612, 1585, 1531, 1542, 1291, 1195, 1150, 751, 635 cm$^{-1}$; $^1$H NMR (300 MHz, CDCl$_3$) δ: 2.05–2.14(2H,m), 2.50(2H,t,J=7.1), 2.57(2H,t,J=7.4), 7.23(1H,dt,J=7.4,0.8), 7.61(1H,dt,J=7.7,1.4), 7.67(1H,dd,J=7.7,0.8), 8.73(1H,d,J=8.5), 9.91(1H,s).

EXAMPLE 58

3-(2-Oxo-3-hydroquinolyl)propanoic Acid (58)

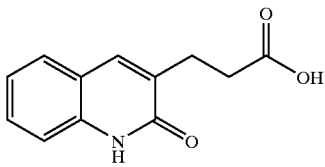
(58)

4-(N-(2-formylphenyl)carbamoyl)butanoic acid (5.12 g) was dissolved in 2% aqueous potassium hydroxide solution (250 ml) and the solution was heated to reflux for 3 hours. Concentrated hydrochloric acid was added to the reaction mixture and the generated precipitates were recovered by filtration. The precipitates were recrystallized from methanol/ether to obtain 2.14 g of 3-(2-oxo-3-hydroquinolyl)propanoic acid. Yield: 45%.

MS (EI, m/z): 217 (M$^+$); IR (neat): 2525, 2078, 1648, 1450, 1214, 1116, 971 cm$^{-1}$; $^1$H NMR (300 MHz, CD$_3$OD); δ: 2.71(2H,t,J=7.1), 2.93(2H,t,J=7.4), 7.23(1H,dt,J=8.2,1.1), 7.32(1H,d,J=8.2), 7.48(1H,dt,J=8.2,1.4), 7.58(1H,d,J=8.0), 7.78(1H,s).

EXAMPLE 59

Ethyl 3-(2-Oxo-3-hydroquinolyl)propanoate (59)

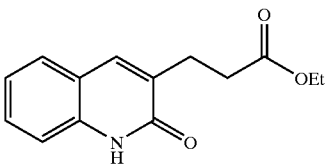
(59)

In ethanol (50 ml), 2.09 g of 3-(2-oxo-3-hydroquinolyl)propanoic acid was dissolved and concentrated hydrochloric acid (1 ml) was added, followed by heating the mixture to reflux for 1.5 hours. Ethanol was removed and the residue was purified by silica gel column chromatography (ethyl acetate:hexane=1:1–3:2–2:1-ethyl acetate) to obtain 2.10 g of ethyl 3-(2-oxo-3-hydroquinolyl)propanoate. Yield: 93%.

MS (EI, m/z): 245 (M$^-$); IR (neat): 2857, 1728, 1657, 1574, 1441, 1374, 1296, 1281, 1259, 1176, 895, 756, 732 cm$^{-1}$; $^1$H NMR (300MHz, CD$_3$OD); δ: 1.23(3H,t,J=7.1), 2.78(2H,t,J=7.1), 3.02(2H,t,J=7.4), 4.14(2H,q,J=7.1), 7.22(1H,dt,J=8.5,1.4H), 7.42(1H,d,J=8.2), 7.48(2H,ddd,J=8.2,2.7), 7.73(1H,s).

EXAMPLE 60

3-(3-Hydroxypropyl)hydroquinoline-2-one (60)

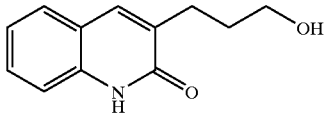
(60)

Lithium aluminum hydride (998 mg) was suspended in anhydrous THF (20 ml), and ethyl 3-(2-oxo-3- hydroquinolyl)propanoate (2.10 g) dissolved in anhydrous tetrahydrofuran (20 ml) was added dropwise to the suspension under cooling in ice, followed by stirring the resulting mixture at room temperature for 1.5 hours. Under cooling in ice, aqueous saturated sodium sulfate solution was added dropwise to the mixture, and then anhydrous sodium sulfate was added, followed by filtration of the mixture. The filtrate was concentrated and the residue was purified by silica gel column chromatography (ethyl acetate:hexane 3:2- ethyl acetate-methanol:ethyl acetate=1:10) to obtain 1.06 g of 3-(3-hydroxypropyl)hydroquinoline-2-one. Yield: 61%.

MS (EI, m/z): 203 (M+); IR (neat): 2361, 1734, 1716, 1653, 1558, 1541, 1506, 1419, 1063 cm$^{-1}$; $^1$H NMR (300 MHz, CD$_3$OD) δ: 1.80–1.90(2H,m), 2.64(2H,t,J=7.4), 3.61 (2H,t,J=6.3), 7.17(1H,dt,J=8.2,1.1), 7.29(1H,d,J=8.2), 7.43 (1H,tt,J=8.2,1.1), 7.54(1H,d,J=7.7), 7.72(1H,s).

EXAMPLE 61

3-(3-(1,1,2,2-Tetramethyl-1-silapropoxy)propyl) hydroquinoline-2-one (61)

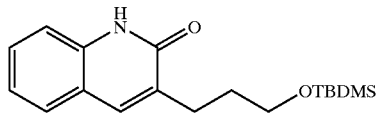

(61)

3-(3-hydroxypropyl)hydroquinoline-2-one (630 mg) was dissolved in tetrahydrofuran (8 ml), and imidazole (380 mg) and t-butyldimethylsilyl chloride (600 mg) were added to the solution, followed by stirring the mixture at room temperature for 2 days. Brine was added to the reaction solution and the mixture was extracted with dichloromethane. Organic layers were combined and dried over anhydrous sodium sulfate. Dichloromethane was removed and the residue was purified by silica gel column chromatography (hexane:ethyl acetate=3:1) to obtain 819 mg of 3-(3-(1,1,2,2-tetramethyl-1-silapropoxy)propyl) hydroquinoline-2-one. Yield: 83%.

m.p.: 117–119° C. MS (EI, m/z): 317 (M+); IR (KBr): 2937, 2855, 1660, 1576, 1245, 1097, 832, 778, 757 cm$^{-1}$; $^1$H NMR (300 MHz, CDCl$_3$); δ: 0.07(6H,s), 0.92(9H,s), 1.93 (2H,quint,J=7.0), 2.74(2H,t,J=7.6), 3.72(2H,t,J=7.3), 7.18 (1H,t,J=7.2), 7.30(1H,d,J=8.5), 7.44(1H,t,J=7.2), 7.50(1H,d, J=7.7), 7.63(1H,s), 11.13(1H,s).

EXAMPLE 62

3-(3-(1,1,2,2-Tetramethyl-1-silapropoxy)propyl) hydroquinoline-2-thione (62)

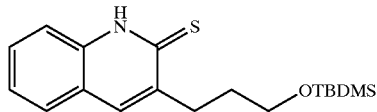

(62)

3-(3-(1,1,2,2-tetramethyl-1-silapropoxy)propyl) hydroquinoline-2-one (804 mg), sodium hydrogen carbonate (300 mg) and diphosphorus pentasulfide (780 mg) were added to pyridine (10 ml) and dimethoxyethane (5 ml), and the mixture was stirred at 65° C. for 8 hours. Sodium hydrogen carbonate (1.0 g) and diphosphorus pentasulfide (1.7 g) were further added and the mixture was stirred at 80° C. for 10 days. Water was added to the reaction mixture and the resultant was extracted with dichloromethane. Organic layers were combined and dried over anhydrous sodium sulfate. Dichloromethane was removed and the residue was purified by silica gel column chromatography (hexane:ethyl acetate=5:1) to obtain 581 mg of 3-(3-(1,1,2,2-tetramethyl-1-silapropoxy)propyl)hydroquinoline-2-thione. Yield: 69%.

m.p.: 134–136° C. MS (EI, m/z): 333 (M+); IR (KBr): 2930, 2856, 1628, 1576, 1251, 1167, 1099, 838, 775 cm$^{-1}$; $^1$H NMR (300 MHz, CDCl$_3$); δ: 0.08(6H,s), 0.93(9H,s), 2.02(2H,quint,J=7.0), 3.02(2H,t,J=7.5), 3.71(2H,t,J=6.3), 7.32(1H,t,J=7.2), 7.49–7.56(2H,m), 7.61(1H,d,J=8.2), 7.69 (1H,s).

EXAMPLE 63

2,4,5-Triaza-7-(3-(1,1,2,2-tetramethyl-1-silapropoxy)propyl)-3-methyltricyclo[7.4.0.0<2,6>] trideca-1(13),3,5,7,9(10),11-hexaene (63)

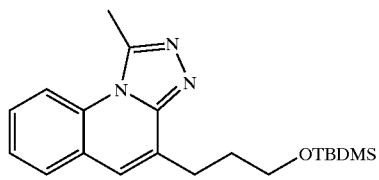

(63)

3-(3-(1,1,2,2-tetramethyl-1-silapropoxy)propyl) hydroquinoline-2-thione (549 mg) was added to ethanol (7.5 ml) and hydrazine hydrate (2.5 ml), and the mixture was stirred at 80 to 105° C. for 14 hours. Ethanol and hydrazine were removed and n-butanol (7 ml) and ortho-triethyl acetate (2.5 ml) were added to the residue, followed by stirring the resulting mixture at 100° C. for 3 hours. After removing n-butanol, the residue was purified by silica gel column chromatography (ethyl acetate) to obtain 466 mg of 2,4,5-triaza-7-(3-(1,1,2,2-tetramethyl-1-silapropoxy) propyl)-3-methyltricyclo[7.4.0.0<2,6>]trideca-1(13),3,5,7,9 (10),11-hexaene. Yield: 80%.

m.p.: 76–78° C. MS (EI, m/z): 355 (M+); IR (KBr): 2928, 2858, 1532, 1412, 1254, 1105, 837, 773 cm$^{-1}$; $^1$H NMR (300 MHz, CDCl$_3$); δ: 0.59(6H,s), 0.91(9H,s), 2.09(2H,quint,J= 6.6), 3.13(2H,t,J=6.9), 3.15(3H,s), 3.73(2H,t,J=6.3), 7.29 (1H,s), 7.50(1H,t,J=7.7), 7.59(1H,td,J=7.7,1.4), 7.75(1H,dd, J=7.7,1.4), 8.21(1H,d,J=8.5).

EXAMPLE 64

2,4,5-Triaza-7-(3-hydroxypropyl)-3-methyltricyclo [7.4.0.0<2,6>]trideca-1(13),3,5,7,9(10), 11-hexaene (64)

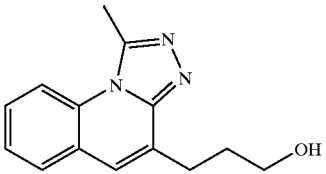

(64)

2,4,5-triaza-7-(3-(1,1,2,2-tetramethyl-1-silapropoxy) propyl)-3-methyltricyclo[7.4.0.0<2,6>]trideca-1(13),3,5,9 (10),11-hexaene (454 mg) was dissolved in tetrahydrofuran (8 ml), and tetrabutylammonium fluoride solution (in 1N tetrahydrofuran, 0.6 ml) was added to the solution, followed by stirring the mixture overnight at room temperature. To the reaction solution, brine was added and the mixture was extracted with dichloromethane. Organic layers were combined and dried over anhydrous sodium sulfate. Dichloromethane was removed and the residue was purified by Chromatorex® column chromatography for amines (ethanol:ethyl acetate=1:10) to obtain 290 mg of 2,4,5-triaza-7-(3-hydroxypropyl)-3-methyltricyclo[7.4.0.0<2,6>]trideca-1(13),3,5,7,9(10),11-hexaene. Yield: 94%.

m.p.: 151–152° C. MS (EI, m/z): 241 (M+); IR (KBr): 3425, 3342, 2858, 1533, 1414, 1064, 757 cm$^{-1}$; $^1$H NMR (300 MHz, CDCl$_3$); δ: 2.05(2H,quint,J=6.2), 3.16(3H,s), 3.19(2H,t,J=6.9), 3.60(2H,q,J=6.2), 3.83(1H,t,J=6.2), 7.34 (1H,s), 7.53(1H,t,J=7.4), 7.63(1H,td,J=7.4,1.4), 7.77(1H,dd, J=7.7,1.6), 8.23(1H,d,J=8.6).

EXAMPLE 65

2,4,5-Triaza-7-(3-chloropropyl)-3-methyltricyclo [7.4.0.0<2,6>]trideca-1(13),3,5,7,9(10), 11-hexaene (65)

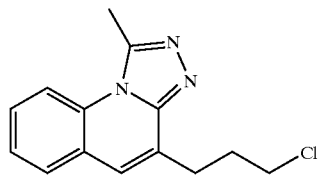

(65)

2,4,5-triaza-7-(3-hydroxypropyl)-3-methyltricyclo [7.4.0.0<2,6>]trideca-1(13),3,5,7,9(10),11-hexaene (238 mg) was dissolved in dichloromethane (9 ml), and carbon tetrachloride (1 ml) and triphenylphosphine (683 mg) were added thereto, followed by stirring the resulting mixture overnight at room temperature. Triphenylphosphine (683 mg) was further added and the mixture was stirred at room temperature for 4 hours. Dichloromethane was removed and the residue was purified by silica gel column chromatography (ethanol:ethyl acetate=1:8) to obtain 230 mg of 2,4,5-triaza-7-(3-chloropropyl)-3-methyltricyclo[7.4.0.0<2,6>] trideca-1(13),3,5,7,9(10),11-hexaene. Yield: 90%.

m.p.: 119–120° C. MS (EI, m/z): 259 (M+); IR (KBr): 3016, 1533, 1414, 749, 721 cm$^{-1}$; $^1$H NMR (300 MHz, CDCl$_3$) δ: 2.41(2H,quint,J=6.6), 3.15(3H,s), 3.23(2H,t,J= 6.6), 3.63(2H,t,J=6.6), 7.33(1H,s), 7.52(1H,td,J=7.4,1.4), 7.62(1H,td,J=7.4,1.4), 7.78(1H,dd,J=8.0,1.4), 8.22(1H,d,J= 8.2).

EXAMPLE 66

2,4,5-Triaza-3-methyl-7-(3-(4-diphenylmethyl) piperazinyl)propyl)tricyclo[7.4.0.0<2,6>]trideca-1 (13),3,5,7,9(10),11-hexaene (66)

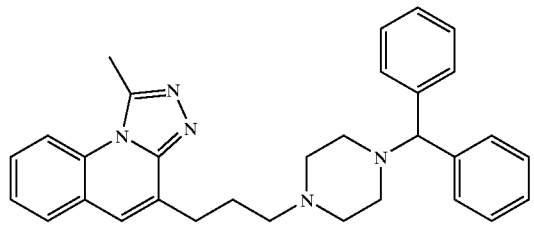

(66)

2,4,5-triaza-7-(3-chloropropyl)-3-methyltricyclo [7.4.0.0<2,6>]trideca-1(13),3,5,7,9(10),11-hexaene (200 mg), diphenylmethylpiperazine (350 mg) and potassium carbonate (160 mg) were added to acetonitrile (7 ml), and the mixture was stirred at 80° C. for 20 hours. Water was added to the reaction solution and the mixture was extracted with dichloromethane. Organic layers were combined and dried over anhydrous sodium sulfate. Dichloromethane was removed and the residue was purified by silica gel column chromatography (ethyl acetate:ethanol=7:1) to obtain 183 mg of 2,4,5-triaza-3-methyl-7-(3-(4-diphenylmethyl) piperazinyl)propyl)tricyclo[7.4.0.0<2,6>]trideca-1(13),3,5, 7,9(10),11-hexaene. Yield: 48%.

IR (KBr): 3404, 2931, 2810, 1534, 1450, 1413, 1141, 1007, 753, 704 cm$^{-1}$; $^1$H NMR (300 MHz, CDCl$_3$) δ: 2.08(2H,quint,J=7.4), 2.30–2.70(8H,m), 2.53(2H,t,J=7.8), 3.08(2H,t,J=7.4), 3.14(3H,s), 4.21(1H,s), 7.13–7.13–7.40 (10H,m), 7.49(1H,t,J=7.4), 7.60(1H,t,J=7.4), 7.74(1H,d,J= 7.7), 8.20(1H,d,J=8.5); HR-MS: Calcd.: C$_{31}$H$_{33}$N$_5$ 475.2736 Found: 475.2744.

EXAMPLE 67

2,4,5,7-Tetraaza-3-phenyl-7-(3-(4-diphenylmethyl) piperazyl)propyl)tricyclo[7.4.0.0<2,6>]trideca-1(9), 3,5,7,10,12-pentaene-8-one (67)

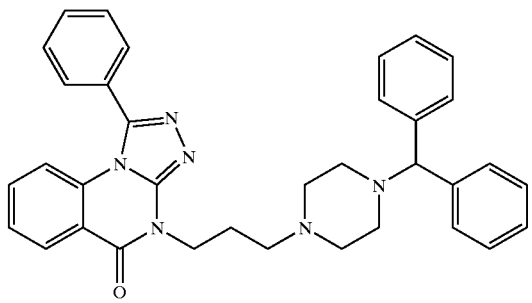

(67)

N-(3-(4-(diphenylmethyl)piperazyl)propyl(2-aminophenyl)formamide (4.5 g) was dissolved in ethanol, and sodium hydroxide (660 mg) and carbon disulfide (3 ml) were added thereto, followed by heating the mixture to reflux for 4 hours. Water was added to the reaction solution and the generated precipitates were recovered by filtration. In ethanol (25 ml), 722 mg aliquot of the precipitates was dissolved, and hydrazine hydrate (10 ml) was added to the solution, followed by heating the mixture to reflux for 7 hours. The reaction mixture was concentrated, and toluene (20 ml), pyridine (20 ml) and benzoyl chloride (0.85 ml) were added to the residue, followed by heating the resulting mixture to reflux for 2 hours. Toluene and pyridine were removed and water was added to the residue, followed by extraction of the resultant 3 times with ethyl acetate. Organic layers were combined and washed with brine. The solution was dried over anhydrous sodium sulfate and the resultant was concentrated, followed by purifying the residue by silica gel column chromatography (dichloromethane:ethanol=20:1) to obtain 207 mg of amorphous 2,4,5,7-tetraaza-3-phenyl-7-(3-(4-diphenylmethyl) piperazyl)propyl)tricyclo[7.4.0.0<2,6>]trideca-1(9),3,5,7, 10,12-pentaene-8-one Yield: 24%.

MS (m/z): 554 (M+); IR (KBr): 3446, 3059, 3027, 2957, 2812, 1680, 1599, 1563, 1495, 1550, 1282, 1151, 1074, 1007, 758, 704 cm$^{-1}$; $^1$H-NMR (300 MHz, CDCl$_3$, δ ppm): 2.18(2H,quint,J=6.9), 1.96–2.35(8H,m), 2.69(2H,t,J=7.1), 4.08(1H,s), 4.11(1H,t,J=7.1), 4.91(2H,t,J=7.1), 7.10–76 (17H,m), 7.97(1H,d,J=7.1), 7.59(1H,d,J=7.0); HR-MS: as C$_{35}$H$_{34}$N$_6$O Calcd.: 554.2794, Found: 554.2799.

EXAMPLE 68

2,4,5,7-Tetraaza-3-propyl-11-methoxy-7-(3-(4-diphenylmethyl)piperazinyl)propyl)tricyclo[7.4.0.0<2,6>]trideca-1(13),3,5,9(10),11-pentaene-8-one (68)

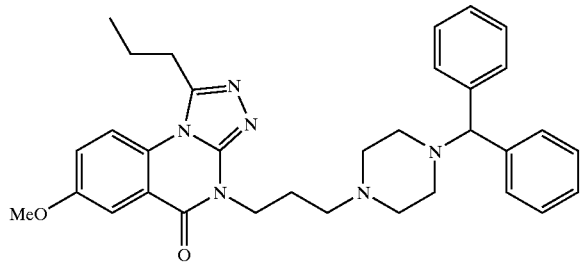

(68)

To 6-methoxy-3-(3-(4-(diphenylmethyl)piperazinyl)propyl)-2-thioxohydroquinazoline-4-one (190 mg), ethanol (5 ml) and hydrazine hydrate (2 ml) were added and the resultant was stirred at 80 to 100° C. for 6 hours. Ethanol and hydrazine were removed, and n-butanol (7 ml) and ortho-triethyl acetate (1 ml) were added to the residue, followed by stirring the mixture at 110° C. for 3 hours. After removing n-butanol, the residue was purified by silica gel column chromatography (ethyl acetate:ethanol=8:1) to obtain 153 mg of amorphous 2,4,5,7-tetraaza-3-propyl-11-methoxy-7-(3-(4-diphenylmethyl)piperazinyl)propyl)tricyclo[7.4.0.0<2,6>]trideca-1(13),3,5,9(10),11-pentaene-8-one Yield: 73%.

LR-MS (m/z): 550 (M+); IR (KBr): 3432, 2963, 1679, 1575, 1501, 1456, 1032, 758, 708 cm$^{-1}$; $^1$H-NMR (300 MHz, CDCl$_3$, δ ppm): 1.13(3H,t,J=7.4), 1.98(2H,quint,J=7.4), 2.04(2H,t,J=8.0), 2.00–2.65(8H,m), 2.52(2H,t,J=7.2), 3.14(2H,t,J=7.4), 3.93(3H,s), 4.09(1H,s), 4.43(2H,t,J=7.2), 7.10–55(1H,m), 7.72(1H,d,J=9.3), 7.85(1H,s); HR-MS: as C$_{33}$H$_{38}$N$_6$O$_2$ Calcd.: 550.3056, Found: 550.3068.

EXAMPLE 69

Methyl 3-(3-Hydroxyquinoxaline-2-yl)propanoate (69)

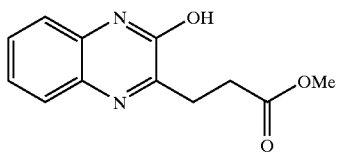

(69)

Dimethyl 2-ketoglutarate (3.75 g) and o-phenylenediamine (2.5 g) were dissolved in methanol (30 ml), and the mixture was stirred overnight. The precipitated crystals were recovered by filtration and washed with water and methanol to obtain 5.06 g of methyl 3-(3-hydroxyquinoxaline-2-yl)propanoate Yield: 94%.

LR-MS (m/z): 232 (M+); IR (KBr): 2904, 2851, 1727, 1662, 1304, 1187, 893, 761 cm$^{-1}$; NMR (300 MHz, CDCl3): 2.92(2H,t,J=7.1), 3.31(2H,t,J=7.1), 3.72(3H,s), 7.25–7.38 (2H,m), 7.42–7.54(1H,m), 7.78–7.82(1H,m).

EXAMPLE 70

3-(3-Hydroxyquinoxaline-2-yl)propanoic Acid (70)

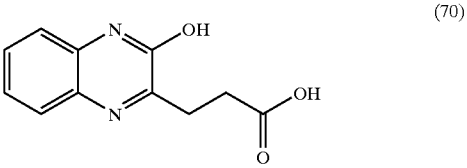

(70)

Methyl 3-(3-hydroxyquinoxaline-2-yl)propanoate (701 mg) was dissolved in dimethylsulfoxide (8 ml), dimethylformamide (8 ml), dimethylformamide (20 ml) and water (10 ml), and then lithium hydroxide (80 mg) was added to the solution, followed by stirring the mixture overnight at room temperature. Then lithium hydroxide (110 mg) was further added and the mixture was stirred for 2 days. To the reaction solution, 1N hydrochloric acid was added and the resulting mixture was extracted 3 times with ethyl acetate. Organic layers were combined and washed with brine. The resultant was dried over anhydrous sodium sulfate and then concentrated to obtain 642 mg of 3-(3-hydroxyquinoxaline-2-yl)propanoic acid Yield: 97%.

LR-MS (m/z): 218 (M+); IR (KBr): 3107, 3019, 2915, 1685, 1641, 1562, 1425, 1314, 1213, 769 cm$^{-1}$; $^1$H-NMR (300 MHz, DMSO, δ ppm): 2.69(2H,t,J=7.1), 2.98(2H,t,J=7.1), 7.21–7.36(2H,m), 7.40–7.48(1H,m), 7.62–7.70(1H,m).

EXAMPLE 71

3-(3-Hydroxyquinoxaline-2-yl)-1-(4-(diphenylmethyl)piperidyl)propane-1-one (71)

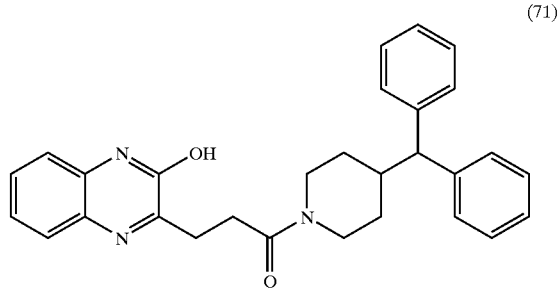

(71)

3-(3-hydroxyquinoxaline-2-yl)propanoic acid (537 mg) and diphenyhmethylpiperidine (862 mg) were dissolved in dimethylformamide, and Bop (1.20 g) and diisopropylethylamine (1.3 ml) were added to the solution, followed by stirring the mixture at room temperature for 3 hours. After removing dimethylformamide, water was added and the resulting mixture was extracted 3 times with ethyl acetate. Organic layers were combined and washed with brine. The resultant was dried over anhydrous sodium sulfate and concentrated, followed by purifying the residue by silica gel column chromatography (ethyl acetate:hexane=3:1) to obtain 923 mg of 3-(3-hydroxyquinoxaline-2-yl)-1-(4-(diphenylmethyl)piperidyl)propane-1-one Yield: 83%.

LR-MS (m/z): 451 (M+); IR (KBr): 3447, 1670, 1610, 1454, 844, 754, 705 cm$^{-1}$; $^1$H-NMR (300 MHz, CDCl$_3$, δ ppm): 1.01–1.30(2H,m), 1.40–1.88(2H,m), 2.28–2.40(1H, m), 2.43–2.62(1H,m), 2.84–2.93(2H,m), 3.21–3.33(2H,m), 3.42–3.57(2H,m), 3.99(1H,brs), 7.12–7.42(13H,m), 7.71–7.78(1H,m).

EXAMPLE 72

3-(3-(4-(Diphenylmethyl)piperidyl)propyl) quinoxaline-2-ol (72)

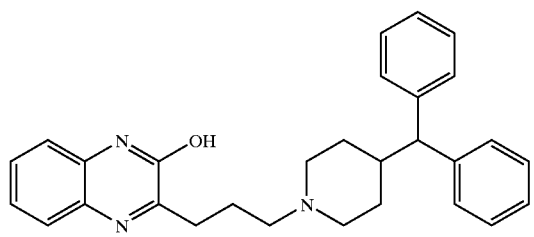

(72)

Under argon atmosphere, 3-(3-hydroxyquinoxaline-2-yl)-1-(4-(diphenylmethyl)piperidyl)propane-1-one (700 mg) was dissolved in tetrahydrofuran (17 ml), and lithium aluminum hydride (100 mg) was added to the solution, followed by stirring the mixture overnight at room temperature and then at 60° C. for 2 hours. Ethanol and saturated aqueous sodium sulfate solution were added to the reaction mixture under cooling in ice, and the generated precipitates were removed by filtration, followed by concentrating the filtrate. The residue was purified by Chromatorex® Column for amines (ethyl acetate) to obtain 387 mg of 3-(3-(4-(diphenylmethyl)piperidyl)propyl)quinoxaline-2-ol. Yield: 57%.

LR-MS (m/z): 437 (M+); IR (KBr): 2903, 1665, 1565, 1495, 1446, 1112, 755, 705 cm$^{-1}$; $^1$H-NMR (300 MHz, CDCl$_3$, δ ppm): 0.93–1.10(2H,m), 1.38–1.47(2H,m), 1.80–1.93(2H,m), 1.94–2.10(3H,m), 2.41–2.50(2H,m), 3.41–2.50(2H,m), 2.81–3.20(4H,m), 3.32–3.39(1H,m), 7.10–7.42(13H,m), 7.76–7.79(1H,m).

EXAMPLE 73

3-(3-(4-(Diphenylmethyl)piperidyl)propyl) quinoxaline-2-thiol (73)

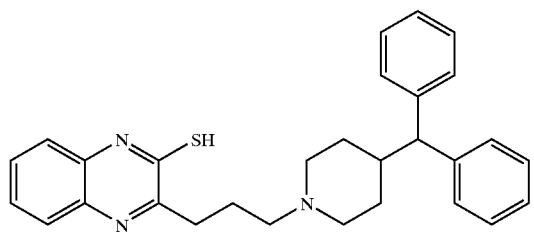

(73)

3-(3-(4-(diphenylmethyl)piperidyl)propyl)quinoxaline-2-ol (257 mg) was dissolved in THF, and Lawesson's reagent (200 mg) was added to the solution, followed by stirring the mixture at 60° C. for 8 hours. Then Lawesson's reagent (110 mg) was further added and the mixture was stirred at 60° C. for 8 hours. Water was added to the mixture and then the mixture was extracted with dichloromethane. Organic layers were combined and washed with brine. The resultant was dried over anhydrous sodium sulfate and the residue was purified by (ethanol:ethyl acetate=10:1) to obtain 103 mg of 3-(3-(4-(diphenylmethyl)piperidyl)propyl)quinoxaline-2-thiol. Yield: 39%.

LR-MS (m/z): 453 (M+); IR (KBr): 2911, 1613, 1446, 1129, 1080, 750, 705 cm$^{-1}$; $^1$H-NMR (300 MHz, CDCl$_3$, δ ppm): 1.32–1.53(2H,m), 1.55–1.63(2H,m), 2.09–2.25(5H, m), 2.60–2.77(2H,m), 3.10–3.32(4H,m), 3.43–3.56(1H,m), 7.12–7.58(13H,m), 7.72–7.80(1,m).

EXAMPLE 74

2,4,5,8-Tetraaza-7-(3-(4-(diphenylmethyl)piperidyl) propyl)tricyclo[7.4.0.0<2,6>]trideca-1(9),3,5,7,10, 12-hexaene (74)

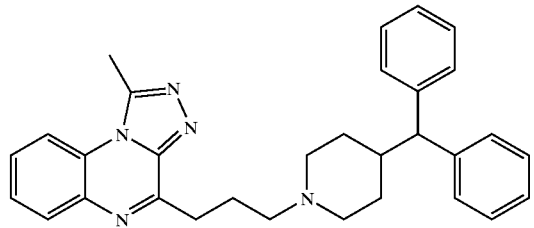

(74)

3-(3-(4-(diphenylmethyl)piperidyl)propyl)quinoxaline-2-thiol (102 mg) was dissolved in ethanol (4.5 ml), and hydrazine hydrate (2 ml) was added, followed by stirring the mixture at 90° C. for 2 hours. Ethanol and hydrazine were removed, and n-butanol (5 ml) and ortho-triethyl acetate (2 ml) were added to the residue, followed by stirring the resulting mixture at 100° C. for 3 hours. After removing n-butanol, the residue was purified by silica gel column chromatography (ethyl acetate:ethanol) to obtain 63 mg of 2,4,5,8-tetraaza-7-(3-(4-(diphenylmethyl)piperidyl)propyl) tricyclo[7.4.0.0<2,6>]trideca-1(9),3,5,7,10,12-hexaene. Yield: 59%.

m.p.: 88–90° C. LR-MS (m/z): 475 (M+); IR (KBr): 3440, 3359, 3257, 2938, 2905, 2778, 1496, 1454, 1428, 1114, 760, 704 cm$^{-1}$; $^1$H-NMR (300 MHz, CDCl$_3$, δ ppm): 0.90–1.08 (2H,m), 1.40–1.55(2H,m), 1.85–2.12(3H,m), 2.15–2.24(2H, m), 2.51–2.60(2H,m), 2.82–2.93(2H,m), 3.15(3H,s), 3.31–3.42(3H,m), 7.10–7.40(10H,m), 7.60–7.72(2H,m), 8.02–8.12(1H,m), 8.14–8.20(1H,m); HR-MS: as C$_{31}$H$_{33}$N$_5$, Calcd.: 475.2736, Found: 475.2725.

EXAMPLE 75

N-(2-((1,1,2,2-Tetramethyl-1-silapropoxy)methyl) phenyl)(2-aminophenyl)formamide (75)

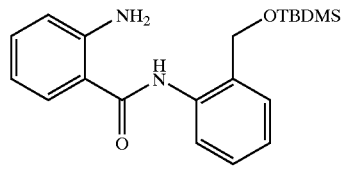

(75)

2-nitrobenzoyl chloride (1.4 ml) was dissolved in THF (50 ml), and then diisopropylethylamine (2.2 ml) and solution of t-butyldimethylsilyloxy (2-aminobenzyl)ether (2.45 g) in THF (20 ml) were added dropwise to the solution, followed by stirring the mixture overnight. Water was added to the reaction solution and the resultant was extracted 3 times with ethyl acetate. Organic layers were combined and washed with brine. The resultant was dried over anhydrous sodium sulfate and concentrated. The residue was dissolved in ethanol (45 ml), and 10% palladium/carbon (300 mg) was added under hydrogen atmosphere, followed by stirring the resulting mixture for 4 hours. After removing 10% palladium/carbon by filtration, the filtrate was concentrated to obtain 2.70 g of N-(2-((1,1,2,2-tetramethyl-1-silapropoxy)methyl)phenyl)(2-aminophenyl)formamide. Yield: 68%.

LR-MS (m/z): 356 (M+); IR (KBr): 3470, 3367, 3068, 2956, 2930, 2887, 2855, 1654, 1616, 1585, 1519, 1448, 1365, 1303, 1250, 1191, 1158, 1121, 1038, 843, 776, 742, 715 cm$^{-1}$; $^1$H-NMR (300 MHz, CDCl$_3$, δ ppm): 0.08(6H,s), 0.88(9H,s), 4.79(2H,s), 5.71(2H,s) 7.06(1H,t,J=7.4), 7.13 (1H,d,J=7.4), 7.24(1H,m), 7.36(1H,t,J=7.4), 7.53(1H,d,J= 7.4), 8.24(1H,d,J=7.4), 9.55(1H,s).

EXAMPLE 76

3(2-((1,1,2,2-Tetramethyl-1-silapropoxy)methyl) phenyl)-2-thioxohydroquinazoline-4-one (76)

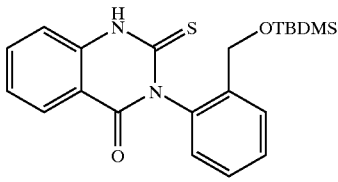

(76)

N-(2-((1,1,2,2-Tetramethyl-1-silapropoxy)methyl) phenyl)(2-aminophenyl)formamide (1.65 g) was dissolved in ethanol (20 ml), and then sodium hydroxide (276 mg) and carbon disulfide (1.5 ml) were added to the solution, followed by stirring the mixture at 60° C. for 9 hours. Water was added to the reaction solution and the crystals were recovered by filtration, followed by washing the crystals with water and ether to obtain 1.52 g of 3(2-((1,1,2,2-tetramethyl-1-silapropoxy)methyl)phenyl)-2-thioxohydroquinazoline-4-one. Yield: 82%.

LR-MS (m/z): 398 (M+); IR (KBr): 3243, 3137, 3069, 3034, 2953, 2931, 2889, 2855, 1663, 1621, 1532, 1487, 1403, 1264, 1229, 1200, 1124, 1094, 1077, 842, 756 cm$^{-1}$; $^1$H-NMR (300 MHz, CDCl$_3$, δ ppm): −0.04(6H,s), 0.84(9H, s), 4.67(2H,s), 7.16(1H,m), 7.34(1H,t,J=7.4), 7.44(1H,t,J= 7.4), 7.51(1H,t,J=7.4), 7.68(2H,m), 8.15(1H,d,J=7.4), 10.5 (1H,s).

EXAMPLE 77

2,4,5,7-Tetraaza-7-(2-((1,1,2,2-tetramethyl-1-silapropoxy)methyl)phenyl)tricyclo[7.4.0.0<2,6>] trideca-1(9),3,5,10,12-pentaene-8-one (77)

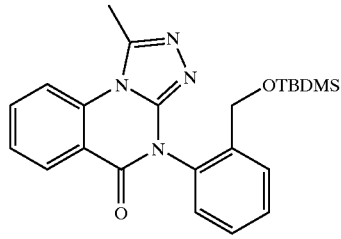

(77)

3(2-((1,1,2,2-tetramethyl-1-silapropoxy)methyl)phenyl)-2-thioxohydroquinazoline-4-one (1.24 g) was dissolved in ethanol (30 ml), and hydrazine hydrate (10 ml) was added thereto, followed by stirring the mixture at 80° C. for 6 hours. Ethanol and hydrazine were removed, and n-butanol (10 ml) and ortho-triethyl acetate (4 ml) were added to the residue, followed by stirring the resulting mixture at 100° C. for 3 hours. After removing n-butanol, the residue was purified by silica gel column chromatography (ethyl acetate:ethanol=10:1) to obtain 718 mg of 2,4,5,7-tetraaza-7-(2-((1,1,2,2-tetramethyl-1-silapropoxy)methyl)phenyl) tricyclo[7.4.0.0<2,6>]trideca-1(9),3,5,10,12-pentaene-8-one. Yield: 55%.

LR-MS (m/z): 420 (M+); IR (KBr): 3120, 3075, 2952, 2932, 2858, 1688, 1609, 1565, 1537, 1485, 1287, 1254, 1119, 1089, 1071, 844, 761 cm$^{-1}$; $^1$H-NMR (300 MHz, CDCl$_3$, δ ppm): −0.13(6H,s), 0.74(9H,s), 2.98(3H,s), 4.63 (2H,s), 7.35(1H,d,J=7.4), 7.42–7.67(4H,m), 7.88(1H,t,J= 7.4), 7.94(1H,t,J=7.4), 8.50(1H,d,J=7.4).

EXAMPLE 78

2,4,5,7-Tetraaza-7-(2-(hydroxymethyl)phenyl)-3-methyltricyclo[7.4.0.0<2,6>]trideca-1(9),3,5,10,12-pentaene-8-one (78)

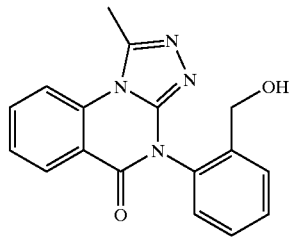

(78)

2,4,5,7-tetraaza-7-(2-((1,1,2,2-tetramethyl-1-silapropoxy)methyl)phenyl)tricyclo[7.4.0.0<2,6>]trideca-1 (9),3,5,10,12-pentaene-8-one (700 mg) was dissolved in THF (19 ml), and tetrabutylammonium fluoride solution (in 1N THF, 1.8 ml) was added to the solution, followed by stirring the mixture at room temperature for 4 hours. Saline was added to the reaction solution and the resultant was extracted with dichloromethane. Organic layers were combined and washed with brine. The resultant was dried over anhydrous sodium sulfate and concentrated, followed by purifying the residue by silica gel column chromatography (ethanol:dichloromethane=10:1) to obtain 390 mg of 2,4,5, 7-tetraaza-7-(2-(hydroxymethyl)phenyl)-3-methyltricyclo [7.4.0.0<2,6>]trideca-1(9),3,5,10,12-pentaene-8-one. Yield: 78%.

LR-MS (m/z): 306 (M⁺); IR (KBr): 3195, 2854, 1687, 1610, 1568, 1536, 1484, 1438, 1297, 1059, 1033, 862, 765 cm⁻¹; ¹H-NMR (300 MHz, CDCl₃, δ ppm): 2.99(3H,s), 4.49(2H,d,J=6.6), 7.35(1H,d,J=7.4), 7.50–7.67(3H,m), 7.70 (1H,d,J=7.4), 7.88(1H,t,J=7.4), 7.96(1H,t,J=7.4), 8.50(1H,d, J=7.4).

EXAMPLE 79

2,4,5,7-Tetraaza-3-methyl-7-(2-((methylsulfonyloxy) methyl)phenyl)tricyclo[7.4.0.0<2,6>]trideca-1(9),3, 5,10,12-pentaene-8-one (79)

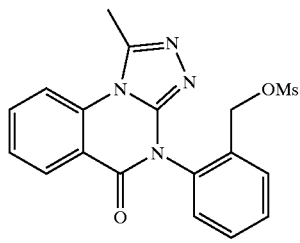

(79)

2,4,5,7-tetraaza-7-(2-(hydroxymethyl)phenyl)-3-methyltricyclo[7.4.0.0<2,6>]trideca-1(9),3,5,10,12-pentaene-8-one (150 mg) was dissolved in dichloromethane (4 ml), and then triethylamine (320 ml) and methanesulfonyl chloride (150 ml) were added thereto, followed by stirring the mixture overnight. Water was added to the reaction solution and the resultant was extracted 3 times with dichloromethane. Organic layers were combined and washed with brine. The resultant was dried over anhydrous sodium sulfate and concentrated, followed by purifying the residue by silica gel column chromatography (dichloromethane:ethanol=10:1) to quantitatively obtain 188 mg of 2,4,5,7-tetraaza-3-methyl-7-(2-((methylsulfonyloxy)methyl)phenyl)tricyclo[7.4.0.0<2,6>] trideca-1(9),3,5,10,12-pentaene-8-one.

LR-MS (m/z): 305 (M⁺-79); IR (KBr): 2910, 2872, 1680, 1605, 1540, 1362, 1191, 1057, 762 cm⁻¹; ¹H-NMR (300MHz, CDCl₃, δ ppm): 2.75(3H,s), 2.99(3H,s), 5.18(2H, s), 7.46(1H,d,J=7.4), 7.57–7.71(4H,m), 7.90(1H,t,J=7.4), 7.96(1H,t,J=7.4), 8.49(1H,d,J=7.4).

EXAMPLE 80

2,4,5,7-Tetraaza-3-methyl-7-(2-((4-diphenylmethyl) piperidyl)methyl)phenyl)tricyclo[7.4.0.0<2,6>] trideca-1(9),3,5,7,10,12-pentaene-8-one (80)

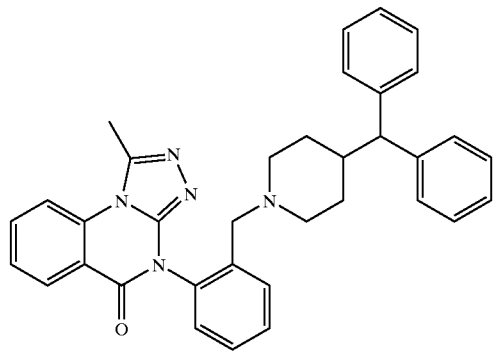

(80)

2,4,5,7-tetraaza-3-methyl-7-(2-((methylsulfonyloxy) methyl)phenyl)tricyclo[7.4.0.0<2,6>]trideca-1(9),3,5,10, 12-pentaene-8-one (180 mg) was dissolved in dimethylformamide (6 ml), and then diphenylmethylpiperidine (202 mg), potassium iodide (83 mg) and potassium carbonate (200 mg) were added to the solution. The mixture was stirred at 80° C. for 16 hours, and dimethylformamide was removed. Water was added to the residue and the resultant was extracted 3 times with dichloromethane. Organic layers were combined and washed with brine. The resultant was dried over anhydrous sodium sulfate and concentrated, followed by purifying the residue by silica gel column chromatography (ethyl acetate:ethanol=10:1) to obtain 241 mg of amorphous 2,4,5,7-tetraaza-3-methyl-7-(2-((4-diphenylmethyl)piperidyl)methyl)phenyl)tricyclo [7.4.0.0<2,6>]trideca-1(9),3,5,7,10,12-pentaene-8-one. Yield: 95%.

LR-MS (m/z): 539 (M⁺); IR (KBr): 3055, 3026, 2936, 2797, 2760, 1696, 1605, 1564, 1488, 1443, 1299, 758, 705 cm⁻¹; ¹H-NMR (300 MHz, CDCl₃, δ ppm): 0.27(1H,m), 0.61(1H,m), 1.26(2H,m), 1.59(2H,m), 1.80(1H,m), 2.28 (1H,m), 2.48(2H,m), 2.99(3H,s), 3.30(2H,m), 3.93(3H,s), 7.04–7.52(14H,m), 7.64(1H,t,J=7.4), 7.89–8.02(2H,m), 8.53(1H,d,J=7.4); HR-MS: as C₃₅H₃₃N₅O, Calcd.: 539.2680 Found: 539.2672.

EXAMPLE 81

1-(3-Nitrophenyl)-4-(diphenylmethyl)piperidine (81)

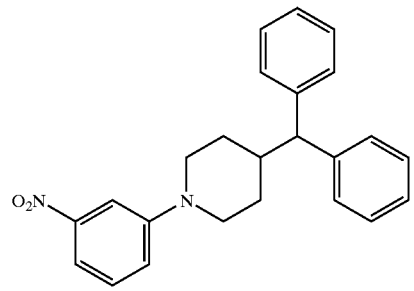

(81)

3-fluoronitrobenzene (520 mg) was dissolved in dimethylsulfoxide (5 ml), and then diphenylmethylpiperidine (926 mg) and potassium carbonate (520 mg) were added, followed by stirring the mixture at 100° C. for 40 hours. Water was added to the reaction mixture and the resultant was extracted 3 times with hexane-ether (1:1) mixed solvent. Organic layers were combined and washed with brine. The resultant was dried over anhydrous sodium sulfate and concentrated. The residue was purified by silica gel column chromatography (hexane:ethyl acetate=4:1) to obtain 880 mg of 1-(3-nitrophenyl)-4-(diphenylmethyl)piperidine. Yield: 64%.

LR-MS (m/z): 372 (M⁺); IR (KBr): 3025, 2946, 2912, 2819, 1615, 1526, 1490, 1454, 1345, 1254, 1199, 1111, 984, 952, 848, 743, 702 cm⁻¹; ¹H-NMR (300 MHz, CDCl₃, δ ppm): 1.22–1.41(2H,m), 1.65–1.78(2H,m), 2.22–2.40(1H, m), 2.76–2.92(2H,m), 3.50–3.56(1H,m), 3.68–3.80(2H,m), 7.10–7.40(12H,m), 7.58–7.66(1H,m), 7.66–7.70(1H,m).

EXAMPLE 82

3-(4-(Diphenylmethyl)piperidyl)phenylamine (82)

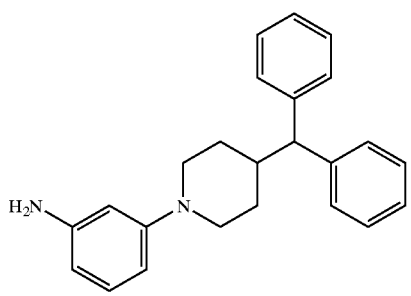

(82)

1-(3-nitrophenyl)-4-(diphenylmethyl)piperidine (854 mg) was dissolved in ethanol (60 ml), and 10% palladium/carbon (76 mg) was added thereto, followed by stirring the mixture overnight under hydrogen atmosphere. Palladium/carbon was removed by filtration through Celite and the filtrate was concentrated, followed by purifying the residue by silica gel column chromatography (hexane:ethyl acetate=5:4) to obtain 711 mg of 3-(4-(diphenylmethyl)piperidyl) phenylamine. Yield: 90%.

LR-MS (m/z): 342 (M$^+$); IR (KBr): 3452, 3369, 3054, 3027, 2941, 2912, 2806, 1601, 1497, 1451, 1386, 1267, 1177, 1109, 965, 833, 738, 703 cm$^{-1}$; $^1$H-NMR (300 MHz, CDCl$_3$, δ ppm): 1.21–1.43(2H,m), 1.60–1.70(2H,m), 2.18–2.33(1H,m), 2.60–2.76(2H,m), 3.50–3.65(3H,m), 6.18–6.40(3H,m), 6.98–7.10(1H,m), 7.15–7.22(1H,m), 7.23–7.38(9H,m).

EXAMPLE 83

N-(3-(4-Diphenylmethyl)piperidyl)(2-nitrophenyl) formamide (83)

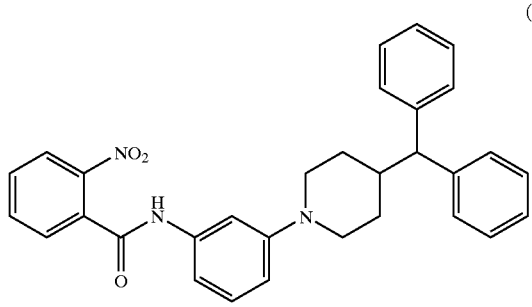

(83)

3-(4-(diphenylmethyl)piperidyl)phenylamine (640 mg) was dissolved in 50 ml of THF, and then diisopropylethylamine (0.5 ml) and 2-nitrobenzoyl chloride (0.27 ml) were added thereto, followed by stirring the mixture overnight. Water was added to the reaction mixture and the resultant was extracted 3 times with ethyl acetate. Organic layers were combined and washed with brine. The resultant was dried over anhydrous sodium sulfate and concentrated, followed by purifying the residue by silica gel column chromatography (hexane:ethyl acetate=4:1) to obtain 910 mg of N-(3-(4-diphenylmethyl)piperidyl)(2-nitrophenyl) formamide. Yield: 99%.

LR-MS (m/z): 491 (M$^+$); IR (KBr): 3375, 3294, 3026, 2940, 2910, 2809, 1662, 1608, 1530, 1494, 1445, 1347, 1312, 1257, 1178, 966, 853, 751, 702 cm$^{-1}$; $^1$H-NMR (300 MHz, CDCl$_3$, δ ppm): 1.23–1.40(1H,m), 1.52–1.70(2H,m), 2.20–2.38(1H,m), 2.65–2.80(2H,m), 3.50–3.55(1H,m), 3.61–3.74(2H,m), 6.70–6.75(1H,m), 6.92–6.98(1H,m), 7.15–7.40(12H,m), 7.58–7.65(2H,m), 7.66–7.78(1H,m), 7.08–8.14(1H,m).

EXAMPLE 84

N-(3-(4-Diphenylmethyl)piperidyl)(2-aminophenyl) formamide (84)

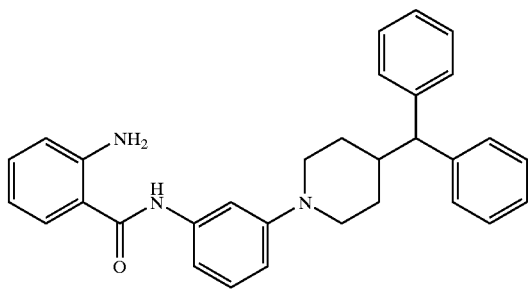

(84)

N-(3-(4-diphenylmethyl)piperidyl)(2-nitrophenyl) formamide (888 mg) was dissolved in ethanol (60 ml), and then 10% palladium/carbon (49 mg) was added, followed by stirring the mixture overnight under hydrogen atmosphere. Palladium/carbon was removed by filtration and the filtrate was concentrated. The residue was purified by silica gel column chromatography (ethyl acetate:hexane=1:2) to obtain 760 mg of N-(3-(4-diphenylmethyl)piperidyl)(2-aminophenyl)formamide. Yield: 91%.

LR-MS (m/z): 46 1 (M$^+$); IR (KBr): 3492, 3380, 3357, 3025, 2947, 2907, 2801, 1649, 1609, 1580, 1534, 1494, 1440, 1249, 1178, 751, 702 cm$^{-1}$; $^1$H-NMR (300 MHz, CDCl$_3$, δ ppm): 1.30–1.49(1H,m), 1.50–1.75(3H,m), 2.20–2.35(1H,m), 2.67–2.82(2H,m), 3.51–3.59(1H,m), 3.62–3.71(2H,m), 5.46(1H,brs), 6.65–6.80(2H,m), 6.92–7.01(1H,m), 7.13–7.38(13H,m), 7.42–7.46(1H,m), 7.63–7.71(1H,m).

EXAMPLE 85

2,4,5,7-Tetraaza-3-methyl-7-(3-(4-diphenylmethyl) piperazyl)phenyl)tricyclo[7.4.0.0<2,6>]trideca-1(9), 3,5,7,10,12-pentaene-8-one (85)

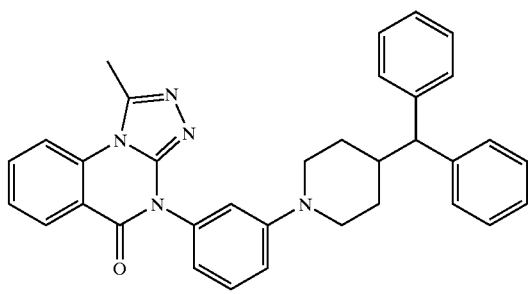

(85)

N-(3-(4-diphenylmethyl)piperidyl)(2-aminophenyl) formamide (700 mg) was dissolved in ethanol (18 ml), and then sodium hydroxide (90 mg) and carbon disulfide (1 ml)

were added thereto, followed by stirring the mixture at 60° C. for 30 hours. Water was added to the reaction solution and the precipitates were recovered by filtration. In ethanol (30 ml), 630 mg aliquot of the precipitates were dissolved and hydrazine hydrate (6 ml) was added to the solution. The mixture was stirred at 80° C. for 4 hours and concentrated. To the residue, n-butanol (30 ml) and ortho-triethyl acetate (2 ml) were added and the mixture was stirred at 110° C. for 3 hours, followed by evaporation of n-butanol. Water was added to the residue and the resulting mixture was extracted 3 times with dichloromethane. Organic layers were combined and washed with brine. The resultant was dried over anhydrous sodium sulfate and concentrated. The residue was purified by silica gel column chromatography (ethyl acetate:ethanol=15:1) to obtain 330 mg of 2,4,5,7-tetraaza-3-methyl-7-(3-(4-diphenylmethyl)piperazyl)phenyl)tricyclo [7.4.0.0<2,6>]trideca-1(9),3,5,7,10,12-pentaene-8-one. Yield: 50%.

m.p. 277–279° C. LR-MS (m/z): 525 (M$^+$); IR (KBr): 3424, 3060, 3026, 2938, 2804, 1684, 1607, 1562, 1535, 1489, 1439, 1295, 1246, 1180, 998, 962, 757, 705 cm$^{-1}$; $^1$H-NMR (300 MHz, CDCl$_3$, δ ppm): 1.22–1.40(1H,m), 1.58–1.70(1H,m), 2.20–2.35(1H,m), 2.68–2.82(2H,m), 2.97 (3H,s), 3.50–3.57(1H,m), 3.60–3.72(2H,m), 6.81–6.95(2H, m), 6.95–7.05(1H,m), 7.11–7.21(2H,m), 7.22–7.38(8H,m), 7.36–7.43(1H,m), 7.55–7.60(1H,m), 7.82–7.98(2H,m), 8.47–8.52(1H,m); HR-MS: as C$_{34}$H$_{31}$N$_5$O Calcd.: 525.2547 Found: 525.2529.

EXAMPLE 86

1-(4-(Diphenylmethyl)piperazinyl)pentane-3-ol (86)

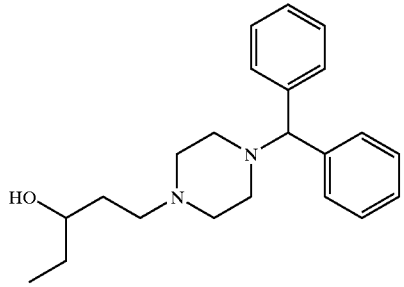

(86)

Diphenylmethylpiperazine (2.20 g) was dissolved in dimethylformamide (25 ml), and then 1-chloro-3-pentanol (1.78 g) and potassium carbonate (722 mg) were added thereto, followed by stirring the mixture at 80° C. for 15 hours. After evaporation of dimethylformamide, water was added to the residue and the resultant was extracted 3 times with ethyl acetate. Organic layers were combined and washed with brine. The resultant was dried over anhydrous sodium sulfate and concentrated. The residue was purified by silica gel column chromatography (ethyl acetate) to obtain 1.79 g of amorphous 1-(4-(diphenylmethyl)piperazinyl)pentane-3-ol. Yield: 61%.

MS (m/z): 338 (M$^+$); IR (KBr): 3311, 3065, 3026, 2958, 2877, 2808, 2763, 2682, 1742, 1660, 1598, 1492, 1449, 1283, 1143, 1075, 1006, 842, 758, 706 cm$^{-1}$; $^1$H-NMR (300 MHz, CDCl$_3$, δ ppm): 0.92(3H,t,J=7.4), 1.30–1.70(5H,m), 2.20–2.80(10H,m), 3.60–3.72(1H,m), 4.20(1H,s), 7.16–7.38 (6H,m), 7.39–7.43(4H,m).

EXAMPLE 87

1-(3-Bromopentyl)-4-(diphenylmethyl)piperazine (87)

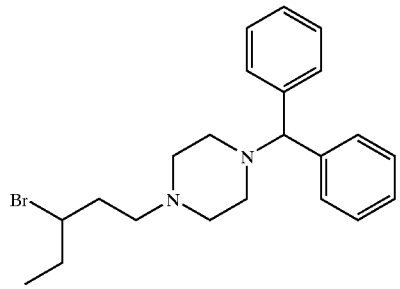

(87)

1-(4-(diphenylmethyl)piperazinyl)pentane-3-ol (940 mg) was dissolved in benzene (10 ml) and ether (10 ml), and then phosphorus tribromide (0.2 ml) was added thereto, followed by stirring the mixture overnight at room temperature. To the reaction mixture, saturated aqueous sodium hydrogen carbonate solution was added and the resultant was extracted 3 times with ethyl acetate. Organic layers were combined and washed with brine. The resultant was dried over anhydrous sodium sulfate and concentrated. The residue was purified by silica gel column chromatography (ethyl acetate:hexane= 1:2) to obtain 340 mg of 1-(3-bromopentyl)-4-(diphenylmethyl)piperazine. Yield: 31%.

LR-MS (m/z): 400 (M$^+$); IR (KBr): 3419, 2968, 2361, .1654, 1492, 1452, 1279, 1123, 1079, 1030, 947 cm$^{-1}$; $^1$H-NMR (300 MHz, CDCl$_3$, δ ppm): 1.03(3H,t,J=7.4), 1.60–2.06(6H,m), 2.33–2.60(8H,m), 3.99–4.08(1H,m), 4.21 (1H,s), 7.14–7.38(6H,m), 7.39–7.50(4H,m).

EXAMPLE 88

1-(4-Aza-4-diazo-3-ethylbuto4-enyl)-4-(diphenylmethyl)piperazine (88)

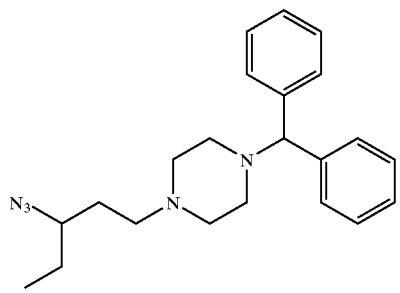

(88)

1-(3-bromopentyl)-4-(diphenylmethyl)piperazine (325 mg) was dissolved in dimethylformamide (5 ml) and water (1 ml), and then sodium azide (90 mg) was added thereto, followed by stirring the mixture at 60° C. for 6 hours. After removing dimethylformamide, water was added to the residue and the resultant was extracted 3 times with ethyl acetate. Organic layers were combined and washed with brine. The resultant was dried over anhydrous sodium sulfate and concentrated. The residue was purified by silica gel column chromatography (ethyl acetate:hexane=1:2) to obtain 193 mg of 1-(4-aza4-diazo-3-ethylbuto-4-enyl)-4-(diphenylmethyl)piperazine as an oily product. Yield: 82%.

LR-MS (m/z): 363 (M⁺); IR (neat): 2962, 2810, 2097, 1452, 1277, 1153, 1008, 703 cm⁻¹; ¹H-NMR (300 MHz, CDCl₃, δ ppm): 0.97(3H,t,J=7.4), 1.50–1.80(6H,m), 2.30–2.60(8H,m), 3.24–3.33(1H,m), 4.21(1H,S), 7.16–7.38 (6H,m), 7.39–7.50(4H,m).

EXAMPLE 89

1-(4-Diphenylmethyl)piperazinyl)pento-3-ylamine (89)

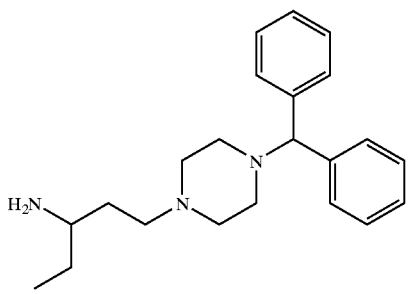

(89)

1-(4-aza-4-diazo-3-ethylbuto-4-enyl)-4-(diphenylmethyl) piperazine (186 mg) was dissolved in THF (4 ml), and triphenylphosphine (181 mg) was added thereto, followed by stirring the mixture at room temperature for 30 hours. Water (0.1 ml) was added to the reaction solution and the resultant was stirred overnight. THF and water were removed and the residue was purified by Chromatorex® column chromatography for amines (ethyl acetate:ethanol= 10:1) to obtain 152 mg of 1-(4-diphenylmethyl)piperazinyl) pento-3-ylamine as an oily product. Yield: 88%.

LR-MS (m/z): 337 (M⁺); IR (neat): 3362, 3302:, 2962, 2802, 1650, 1492, 1280, 1072, 756 cm⁻¹; ¹H-NMR (300 MHz, CDCl₃, δ ppm): 0.91(3H,t,J=7.4), 1.30–2.80(15H,m), 4.20(1H,s), 7.13–7.50(10H,m).

EXAMPLE 90

N-(1-Ethyl-2-(4-(diphenylmethyl)piperazyl)propyl) (2-aminophenyl)formamide (90)

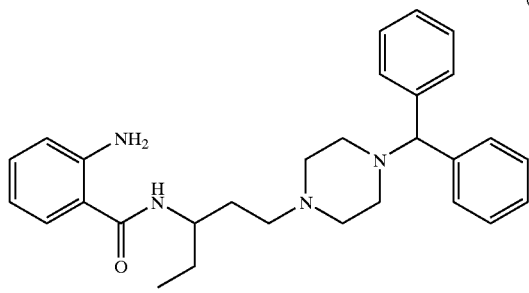

(90)

Isatoic anhydride (80 mg) was dissolved in THF (9 ml), and 1-(4-diphenylmethyl)piperazinyl)pento-3-ylamine (144 mg) was added thereto, followed by stirring the mixture at room temperature for 6 hours. After removing THF, the residue was purified by silica gel column chromatography (ethyl acetate:ethanol=6:1) to obtain 190 mg of amorphous N-(1-ethyl-2-(4-(diphenylmethyl)piperazyl)propyl)(2-aminophenyl)formamide. Yield: 96%.

LR-MS (m/z): 456 (M⁺); IR (KBr): 3479, 3362, 2961, 2807, 1647, 1617, 1585, 1517, 1450, 1272, 1145, 749, 704 cm⁻¹; ¹H-NMR (300 MHz, CDCl₃, δ ppm): 0.93(3H,t,J= 7.4), 1.45–1.90(4H,m), 2.20–2.73(10H,m), 4.04(1H,m), 4.16(1H,s), 5.54(2H,s), 6.59–7.43(14H,m), 7.93(1H,brs).

EXAMPLE 91

3-(1-Ethyl-3-(4-diphenylmethyl)piperazyl)propyl)-2-thioxohydroquinazoline-4-one (91)

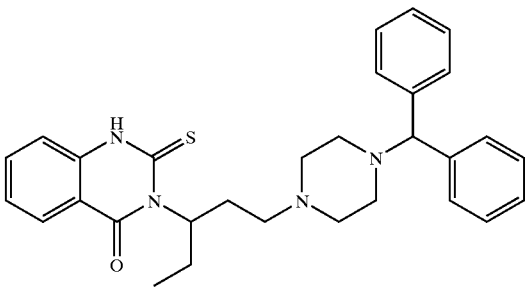

(91)

N-(1-ethyl-2-(4-(diphenylmethyl)piperazyl)propyl)(2-aminophenyl)formamide (200 mg) was dissolved in ethanol (5 ml), and then sodium hydroxide (35 mg) and carbon disulfide (0.2 ml) were added thereto, followed by stirring the mixture at 60° C. for 6 hours. Water was added to the reaction solution and the mixture was extracted 3 times with chloroform. Organic layers were combined and washed with brine. The resultant was dried over anhydrous sodium sulfate and concentrated. The residue was purified by silica gel column chromatography (ethyl acetate:hexane=1:3) to obtain 189 mg of amorphous 3-(1-ethyl-3-(4-diphenylmethyl)piperazyl)propyl)-2-thioxohydroquinazoline-4-one. Yield: 87%.

LR-MS (m/z): 498 (M⁺); IR (KBr): 3448, 2958, 2810, 1693, 1624, 1531, 1396, 1203, 1168, 757, 703 cm⁻¹; ¹H-NMR (300 MHz, CDCl₃, δ ppm): 0.92(3H,t,J=7.4), 1.42–2.60(15H,m), 3.92–4.00(1H,m), 5.93–6.02(1H,m), 7.02–7.42(12H,m), 7.62–7.70(1H,m), 8.03–810(1H,m).

EXAMPLE 92

2,4,5,7-Tetraaza-7-(1-ethyl-3-(4-diphenylmethyl) piperazyl)propyl)-3-methyltricyclo[7.4.0.0<2,6>] trideca-1(9),3,5,7,10,12-pentaene-8-one (92)

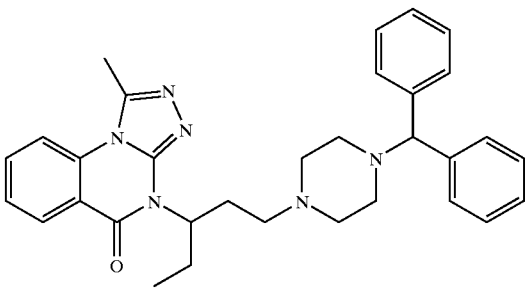

(92)

3-(1-ethyl-3-(4-diphenylmethyl)piperazyl)propyl)-2-thioxohydroquinazoline-4-one (180 mg) was dissolved in ethanol (4 ml), and hydrazine hydrate (1 ml) was added thereto, followed by stirring the mixture at 80° C. for 4 hours. After 15 concentrating the reaction mixture, n-butanol (10 ml) and ortho-triethyl acetate (1.5 ml) were added to the residue, and the mixture was stirred at 110° C. for 3 hours. After removing n-butanol, the residue was purified by silica gel column chromatography (ethyl acetate:ethanol=10:1) to obtain 88 mg of amorphous 2,4,5,7-tetraaza-7-(1-ethyl-3-(4-diphenylmethyl)piperazyl)propyl)-3-methyltricyclo[7.4.0.0<2,6>]trideca-1(9),3,5,7,10,12-pentaene-8-one. Yield: 46%.

LR-MS (m/z): 520 (M⁺); IR (KBr): 3444, 2961, 2933, 2876, 2811, 1676, 1609, 1567, 1488, 1441, 1306, 1283, 1153, 1007, 758, 705 cm⁻¹; ¹H-NMR (300 MHz, CDCl₃, δ ppm): 0.87(3H,t,J=7.4), 1.60–2.80(15H,m), 2.91(3H,s), 3.92–4.01(1H,m), 7.11–7.32(10H,m), 7.51–7.59(1H,m), 7.80–7.90(2H,m), 8.40–8.42(1H,m); HR-MS: as $C_{32}H_{36}N_6O$ Calcd.: 520.2950 Found: 520.2968.

EXAMPLE 93

2,4,5,7-Tetraaza-7-(3-(4-(3,4-dichlorobenzyl)piperazine-1-yl)propyl)-3-methyltricyclo[7.4.0.0<2,6>]trideca-1(13),3,5,9(10),11-pentaene-8-one (93)

(93)

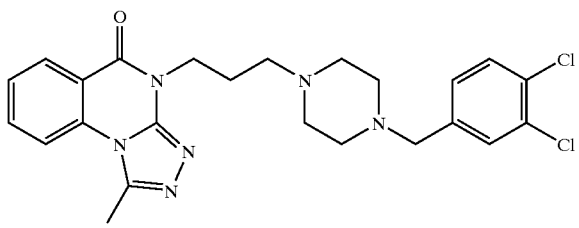

4-(3,4-dichlorobenzyl)piperazine (synthesized by the process described in Japanese Laid Open Patent Application (Kokai) No. 11-147872) was dissolved in dimethylformamide (3 ml), and then 2,4,5,7-tetraaza-7-(3-chloropropyl)-3-methyltricyclo[7.4.0.0<2,6>]trideca-1(13),3,5,9(10),11-pentaene-8-one potassium carbonate (414 mg) and sodium iodide (150 mg) were added to the solution, followed by stirring the mixture at room temperature for 39 hours. Water was added to the reaction mixture and the mixture was extracted 3 times with ethyl acetate. Organic layers were combined and washed with brine. The resultant was dried over anhydrous magnesium sulfate and concentrated. The residue was purified by Chromatorex® column chromatography for amines (hexane:ethyl acetate=1:2) to obtain 230 mg of 2,4,5,7-tetraaza-7-(3-(4-(3,4-dichlorobenzyl)piperazine-1-yl)propyl)-3-methyltricyclo[7.4.0.0<2,6>]trideca-1(13),3,5,9(10),11-pentaene. Yield: 47%.

m.p. 77–79° C. LR-MS (m/z): 484 (M⁺); IR (KBr): 3433, 2925, 2829, 1676, 1612, 1600, 1573, 1493, 1475, 1447, 1345, 765 cm⁻¹; ¹H-NMR (300 MHz, CDCl₃, δ ppm): 1.65–2.75(8H,m), 2.07(2H,quint,J=7.2), 2.11(2H,quint,J=7.2), 2.54(2H,t,J=7.2), 2.93(3H,s), 4.43(2H,t,J=7.2), 4.47(2H,t,J=7.2), 7.10(1H,d,J=7.4), 7.35(2H,d,J=7.4), 7.55(1H,t,J=6.8), 7.77–7.89(2H,m), 8.43(1H,d,J=7.4); Elementary Analysis: as $C_{24}H_{26}Cl_2N_6O \cdot 2H_2O$ Calcd.: C: 55.28%, H: 5.80%, N: 16.12%, Cl: 3.60%; Found: C: 55.49%, H: 5.72%, N: 15.93%, Cl: 3.45%.

EXAMPLE 94
3-(2-Oxo-4-phenyl-3-hydroquinolyl)propanoic Acid (94)

(94)

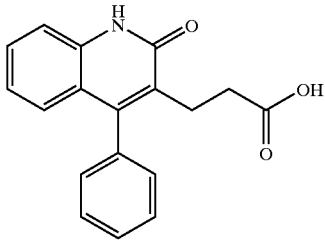

2-aminobenzophenone (1.0 g) and glutaric anhydride (0.70 g) were dissolved in benzene (10 ml), and the solution was heated to reflux for 6 hours. After removing benzene, the residue was dissolved in 2% aqueous potassium hydroxide solution (50 ml) and the resulting solution was heated to reflux for 5.5 hours. Concentrated hydrochloric acid was added to the reaction mixture and the precipitated crystals were recovered by filtration. The crystals were recrystallized from methanol to obtain 0.77 g of 3-(2-oxo-4-phenyl-3-hydroquinolyl)propanoic acid. Yield: 52%.

LR-MS (m/z): 293 (M⁺); IR (KBr): 3430, 3263, 3184, 3032, 1728, 1635, 1593, 1541, 1411, 1283, 1195, 758, 469 cm⁻¹; ¹H-NMR (300 MHz, CDCl₃, δ ppm): 2.46(2H,t,J=6.9), 2.71(2H,t,J=6.9), 7.04(2H,m), 7.19(2H,d,J=7.8), 7.27(2H,d,J=7.8), 7.40–7.54(4H,m).

EXAMPLE 95
3-(3-oxo-3-(4-(Diphenylmethylpiperidyl)propyl)-4-phenylhydroquinoline-2-one (95)

(95)

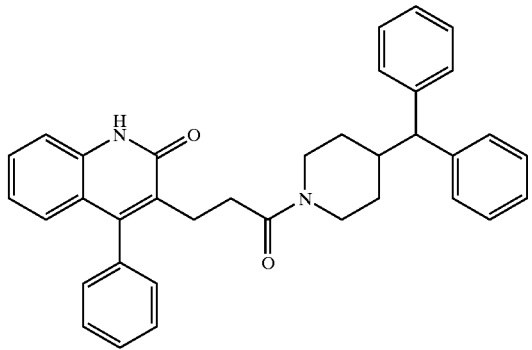

3-(2-oxo-4-phenyl-3-hydroquinolyl)propanoic acid (0.15 g) was dissolved in dichloromethane (6 ml) and then 4-(diphenylmethyl)piperidine (0.15 g), BOP (0.25 g) and diisobutylethylamine (0.30 ml) were added to the solution, followed by stirring the mixture at room temperature for 1.5 hours. Saturated aqueous ammonium chloride solution was added to the reaction solution and the resulting mixture was extracted with dichloromethane. Organic layers were combined and washed with saturated aqueous sodium hydrogen carbonate solution and with brine. The resultant was dried over anhydrous sodium sulfate and concentrated. The residue was purified by silica gel chromatography (methanol:chloroform=0:1–1:10) to obtain 0.33 g of 3-(3-oxo-3-(4-(diphenylmethylpiperidyl)propyl)-4-phenylhydroquinoline-2-one. Yield: 92%.

LR-MS (m/z): 526 (M⁺); IR (KBr): 3446, 3165, 3109, 3056, 3025, 2948, 2908, 1651, 1488, 1445, 1379, 1274, 755, 703 cm⁻¹; ¹H-NMR (300 MHz, CDCl₃, δ ppm): 1.05(2H, m), 1.59,(2H,m), 2.31(1H,m), 2.40–260(3H,m), 2.62–2.83

(2H,m), 2.94(1H,m), 3.44(1H,m), 3.97(1H,m), 4.50(1H,m), 7.02(2H,m), 7.10–7.38(14H,m), 7.38–7.57(3H,m).

EXAMPLE 96

4-Phenyl-3-(3-(4-(diphenylmethyl)piperidyl)propyl)hydroquinoline-2-one (96)

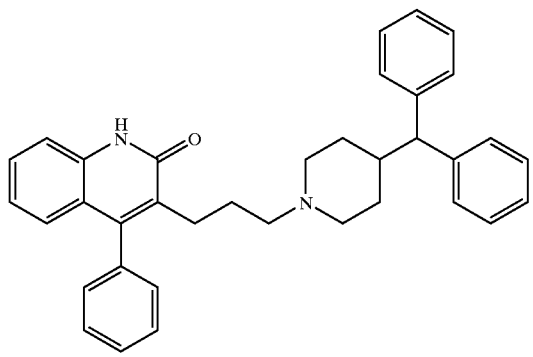

(96)

Lithium aluminum hydride (12 mg) was suspended in anhydrous THF (3 ml), and 3-(3-oxo-3-(4-(diphenylmethylpiperidyl)propyl)-4-phenylhydroquinoline-2-one (0.15 g) dissolved in anhydrous THF (3 ml) was added dropwise thereto under cooling the mixture in ice, followed by stirring the mixture at room temperature for 23 hours. Under cooling in ice, saturated aqueous sodium sulfate solution was added to the reaction mixture, and the solids were removed by filtration. Water was added to the filtrate and the resulting mixture was extracted with ethyl acetate. Organic layers were combined and washed with brine. The resultant was dried over anhydrous sodium sulfate and concentrated. The residue was purified by Chromatorex® column chromatography for amines (ethyl acetate) to obtain 89 mg of 4-phenyl-3-(3-(4-(diphenylmethyl)piperidyl)propyl)hydroquinoline-2-one. Yield: 61%.

MS (m/z) 512 (M$^+$); IR (KBr) 3025, 2940, 2849, 2808, 2767, 1654, 1597, 1560, 1492, 1430, 1382, 1116, 1063, 755, 703 cm$^{-1}$; $^1$H-NMR (300 MHz, CDCl$_3$, δ ppm): 1.21(2H,m), 1.51(2H,m), 1.70(2H,m), 1.82(2H,m), 2.07(1H,m), 2.28(2H,t,J=7.0), 2.48(2H,t,J=7.8), 2.83(2H,d,J=m), 3.47(1H,m), 6.98(2H,d,J=4.4), 7.10–7.58(17H,m).

EXAMPLE 97

2,4,5-Triaza-3,5-dimethyl-8-phenyl-7-(3-(4-(diphenylmethyl)piperidyl)propyl)tricyclo[7.4.0.0<2,6>]trideca-1,3,7,10,12-pentaene (97)

(97)

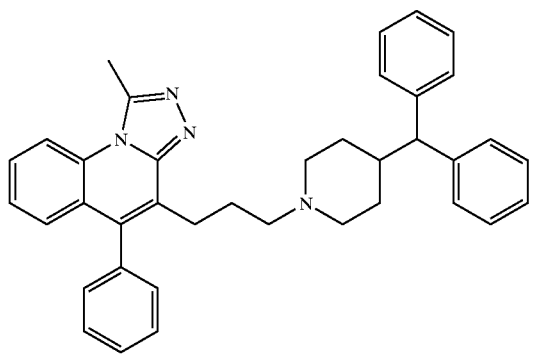

4-phenyl-3-(3-(4-(diphenylmethyl)piperidyl)propyl)hydroquinoline-2-one (87 mg) and Lawesson's reagent (0.10 g) were dissolved in toluene (5 ml), and the solution was stirred at 80° C. for 6 hours. Saturated aqueous sodium carbonate solution was added to the reaction solution and then the resulting mixture was extracted with dichloromethane. Organic layer was washed with brine and dried over anhydrous sodium sulfate, followed by concentrating the resulting product. The residue was dissolved in a small amount of chloroform, and methanol was added, followed by recovering the precipitated crystals by filtration. These crystals (35 mg) were dissolved in 1-butanol (2 ml), and hydrazine hydrate was added thereto, followed by stirring the mixture at 120° C. for 9 hours. Ethanol and hydrazine were removed, and n-butanol (2 ml) and ortho-triethyl acetate (1 ml) were added to the residue, and the resulting mixture was heated at 140° C. for 3 hours. After removing n-butanol, the residue was purified by preparative TLC (chloroform:methanol=20:1) and by Chromatorex® column chromatography for amines (hexane:ethyl acetate=5:1) to obtain 6 mg of amorphous 2,4,5-triaza-3,5-dimethyl-8-phenyl-7-(3-(4-(diphenylmethyl)piperidyl)propyl)tricyclo[7.4.0.0<2,6>]trideca-1,3,7,10,12-pentaene. Yield: 6%.

LR-MS (m/z): 550 (M$^+$); IR (neat): 3060, 3025, 2925, 2852, 1725, 1648, 1597, 1493, 1451, 1419, 1225 cm$^{-1}$; $^1$H-NMR (300 MHz, CDCl$_3$, δ ppm): 1.21(2H,m), 1.51(2H,m), 1.64–1.98(4H,m), 2.17(1H,m), 2.22–2.41(2H,m), 2.67–2.88(4H,m), 3.49(3H,s), 3.46(1H,m), 7.15(2H,m), 7.20–7.52(15H,m), 7.58(1H,t,J=7.0), 8.25(1H,d,J=8.2); HR-MS: as C$_{38}$H$_{38}$N$_4$ Calcd.: 550.3096 Found: 550.3121.

EXAMPLE 98

4-(N-(2-Acetylphenyl)carbamoyl)butanoic Acid (98)

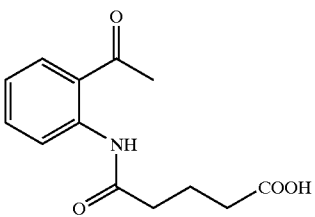

(98)

1-(2-aminophenyl)ethane-1-one (4.00 g) and glutaric anhydride (4.10 g) were dissolved in benzene (30 ml) and the solution was heated to reflux for 3.5 hours, followed by concentration of the mixture. The residue was recrystallized from ethyl acetate to obtain 4.93 g of 4-(N-(2-acetylphenyl)carbamoyl)butanoic acid as colorless plate-like crystals. Yield: 66%.

LR-MS (m/z): 249 (M$^+$); IR (KBr).: 3429, 2922, 1725, 1654, 1624, 1530, 1458, 1242, 1157, 779 cm$^{-1}$; $^1$H-NMR (300MHz, CDCl$_3$, δ ppm): 2.02–2.17(2H,m), 2.45–2.60(4H,m), 2.67(3H,s), 7.13(1H,t,J=7.4), 7.54(1H, t,J=7.4), 7.90(1H,d,J=7.4), 8.76(1H,d,J=7.4), 11.78:(1H,brs).

EXAMPLE 99

3-(4-Methyl-2-oxo-3-hydroquinolyl)propanoic Acid (99)

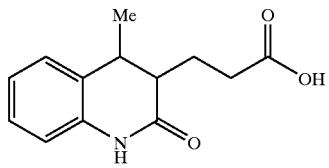

(99)

4-(N-(2-acetylphenyl)carbamoyl)butanoic acid (4.87 g) was dissolved in 2% aqueous potassium hydroxide solution (100 ml), and the resulting solution was heated to reflux overnight. Concentrated hydrochloric acid was added to the reaction solution and the precipitated solids were recrystallized from methanol/chloroform/ethyl acetate to obtain 2.26 g of 3-(4-methyl-2-oxo-3-hydroquinolyl)propanoic acid as colorless crystals. Yield: 50%.

LR-MS (m/z): 231 (M$^+$); IR (KBr): 2986, 1697, 1638, 1604, 1397, 1262, 1202, 1003, 749 cm$^{-1}$; $^1$H-NMR (300MHz, CD$_3$OD, δ ppm): 2.53–2,55(2H,m), 2.57(3H,s), 3.01–3.07(2H,m), 7.23–7.35(2H,m), 7.43–7.52(1H,m), 7.80–7.84(1H,m).

EXAMPLE 100

3-(3-Hydroxypropyl)-4-methylhydroquinoline-2-one (100)

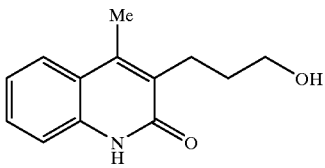

(100)

3-(4-methyl-2-oxo-3-hydroquinolyl)propanoic acid (2.23 g) was dissolved in ethanol (50ml) and concentrated hydrochloric acid (0.7 ml) was added thereto, followed by heating the mixture to reflux for 3 hours. After removing ethanol, saturated aqueous sodium hydrogen carbonate solution was added to the residue and the resulting mixture was extracted with chloroform. Organic layers were combined and washed with brine. The resultant was dried over anhydrous sodium sulfate and concentrated. The residue (2.21 g) was dissolved in anhydrous THF (30 ml), and a suspension of lithium aluminum hydride (390 mg) in anhydrous THF (30 ml) was added dropwise thereto under cooling the mixture in ice, followed by stirring the resulting mixture at 0° C. for 3 hours. Under cooling in ice, saturated aqueous sodium sulfate solution was added dropwise to the reaction mixture and then anhydrous sodium sulfate was added thereto. The mixture was stirred at room temperature for 30 minutes and then filtered. The filtrate was concentrated and the residue was recrystallized from chloroform to obtain 1.1 g of 3-(3-hydroxypropyl)-4-methylhydroquinoline-2-one as colorless crystals. Yield: 53%.

LR-MS (m/z): 217 (M$^+$); IR (KBr): 3448, 3240, 2945, 2887, 1648, 1560, 1504, 1430, 1049, 925, 746 cm$^{-1}$;, $^1$H-NMR (300MHz, CD$_3$Cl δ ppm): 1.82–1.93(2H,m), 2.56 (3H,s), 2.97–3.04(2H,m), 3.52–3.59(2H,m), 4.47–4,56(1H, brs), 7.25–7.30(1H,m), 7.35–7.42(1H,m), 7.50–7.57(1H,m), 7.75–7.78(1H,m).

EXAMPLE 101

4-Methyl-3-(3-(2,2-dimethyl-1,1-diphenyl-1-silapropoxy)propyl)hydroquinoline-2-one (101)

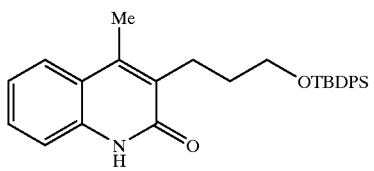

(101)

3-(3-hydroxypropyl)-4-methylhydroquinoline-2-one (1.00 g) was dissolved in DMF (20 ml), and then imidazole (939.5 mg) and t-butyldiphenylsilyl chloride (1.56 ml) were added to the solution, followed by stirring the mixture overnight at room temperature. brine was added to the reaction solution and the resulting mixture was extracted with dichloromethane. Organic layers were combined and dried over anhydrous sodium sulfate. The resultant was concentrated and the residue was purified by silica gel column chromatography (hexane:ethyl acetate 3:1) to obtain 1.90 g of 4-methyl-3-(3-(2,2-dimethyl-1,1-diphenyl-1-silapropoxy)propyl)hydroquinoline-2-one. Yield: 90%.

LR-MS (m/z): 455 (M$^+$); IR (KBr): 3434, 2957, 2927, 2855, 1655, 1561, 1427, 1108, 1087, 744 cm$^{-1}$;, $^1$H-NMR (300 MHz, CDCl$_3$, δ ppm): 1.08(9H,s), 1.75–1.84(2H,m), 2.50(3H,m), 2.87–2.93(2H,m), 3.78(2H,t,J=6.0), 7.15–7.44 (9H,m), 7.66–7.72(5H,m).

EXAMPLE 102

3-(2,4,5-Triaza-3,8-dimethyltricyclo[7.4.0.0<2,6>]trideca-1(9),3,5,7,10,12-hexaene-7-yl)propane-1-ol (102)

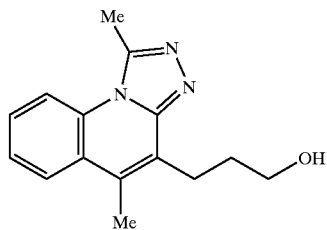

(102)

4-methyl-3-(3-(2,2-dimethyl-1,1-diphenyl-1-silapropoxy)propyl)hydroquinoline-2-one (1.86 g) was dissolved in toluene (20 ml) and Lawesson's reagent (2.47 g) was added thereto, followed by heating the mixture to reflux overnight. Water was added to the reaction mixture and the mixture was extracted with dichloromethane. Organic layers were combined and washed with brine. The resultant was dried over anhydrous sodium sulfate and concentrated. In ethanol (15 ml), 1.01 g aliquot of the residue was dissolved and hydrazine hydrate (5 ml) was added thereto, followed by stirring the resulting mixture at 80 to 105° C. for 4 days. Ethanol and hydrazine were removed, and n-butanol (30 ml) and ortho-triethyl acetate (10 ml) were added to the residue, followed by stirring the resulting mixture at 100° C. for 3 hours. After removing n-butanol, the residue was purified by Chromatorex® column chromatography (chloroform:methanol=10:0→20:1→10:1) to obtain 115 mg of 3-(2,4,5-triaza-3,8-dimethyltricyclo[7.4.0.0<2,6>]trideca-1(9),3,5,7,10,12-hexaene-7-yl)propane-1-ol. Yield: 20%.

LR-MS (m/z): 255 (M$^+$); IR (KBr): 3376, 3230, 2928, 1614, 1527, 1422, 1383, 1048, 765 cm$^{-1}$; 1H-NMR (300 MHz, CDCl$_3$, δ ppm): 1.90–2.00(2H,m), 2.58(3H,s), 3.14 (3H,s), 3.28–3.37(2H,m), 3.42–3.53(2H,m), 4.78(1H,brs), 7.55–7.68(2H,m), 7.97–8.00(1H,m), 8.22–8.26(1H,m).

EXAMPLE 103

2,4,5-Triaza-7-(3-chloropropyl)-3,8-dimethyltricyclo [7.4.0.0<2,6>]trideca-1(9),3,5,7, 10,12-hexaene (103)

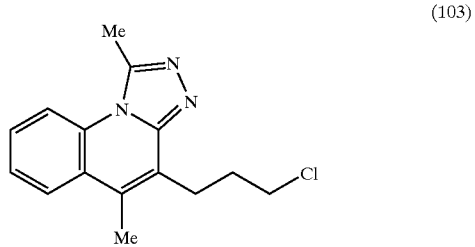

(103)

3-(2,4,5-triaza-3,8-dimethyltricyclo[7.4.0.0<2,6>] trideca-1(9),3,5,7,10,12-hexaene-7-yl)propane-1-ol (110 mg) was dissolved in dichloromethane (5 ml), and then carbon tetrachloride (2 ml) and triphenylphosphine (225 mg) were added to the solution, followed by stirring the mixture overnight at room temperature. Dichloromethane was removed, and the residue was purified by Chromatorex® column chromatography for amines (chloroform:methanol= 100:0→50:1→20:1) to obtain 95 mg of 2,4,5-triaza-7-(3-chloropropyl)-3,8-dimethyltricyclo[7.4.0.0<2,6>]trideca-1 (9),3,5,7,10,12-hexaene. Yield: 81%.

LR-MS (m/z): 273 (M$^+$); IR (KBr): 3433, 2934, 2863, 1618, 1525, 1509, 1424, 1382, 1046, 752 cm$^{-1}$; 1H-NMR (300 MHz, CDCl$_3$, δ ppm): 2.21–2.30(2H,m), 2.60(3H,s), 3.14(3H,s), 3.32–3.38(2H,m), 3.67(2H,t,J=6.3), 7.53–7.66 (2H,m), 7.98–8.01(1H,m), 8.22–8.25(1H,m).

EXAMPLE 104

2,4,5-Triaza-3,8-dimethyl-7-(3-(4-(diphenylmethyl) piperidyl)propyl)tricyclo[7.4.0.0<2,6>]trideca-1(9), 3,5,7,10,12-hexaene (104)

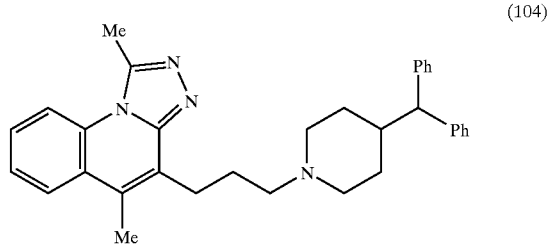

(104)

2,4,5-triaza-7-(3-chloropropyl)-3,8-dimethyltricyclo [7.4.0.0<2,6>]trideca-1(9),3,5,7,10,12-hexaene (35.6 mg) was dissolved in acetonitrile (1.3 ml), and then diphenylmethylpiperidine (49 mg), potassium carbonate (36 mg) and potassium iodide (21.6 mg) were added to the solution, followed by stirring the mixture overnight at 80° C. Water was added to the reaction solution and the resulting mixture was extracted with dichloromethane. Organic layers were combined and washed with brine, followed by drying the resultant over anhydrous sodium sulfate. The resultant was concentrated and the residue was purified by silica gel column chromatography (ethyl acetate:ethanol=5:1) to obtain 8.0 mg of 2,4,5-triaza-3,8-dimethyl-7-(3-(4-(diphenylmethyl)piperidyl)propyl)tricyclo[7.4.0.0<2,6>] trideca-1(9),3,5,7,10,12-hexaene. Yield: 13%.

LR-MS (m/z): 488 (M$^+$); IR (KBr): 2926, 1660, 1450, 1422, 1381, 1114, 1067, 754, 704 cm$^{-1}$; $^1$H-NMR (300 MHz, CDCl$_3$, δ ppm): 1.14–1.28(2H,m), 1.47–1.59(2H,m), 1.60–1.96(4H,m), 2.45–2.51(2H,m), 2.53(3H,s), 2.83–2.92 (2,m), 3.12(3H,s), 3.13–3.20(2H,m), 3.42–3.48(2H,m), 7.10–7.30(10H,m), 7.53–7.62(2H,m), 7.95–7.97(1H,m), 8.20–8.23(1H.m).

EXAMPLE 105

The CCR receptor-inhibiting activities of the compounds represented by Formula I will now be described. Using human eosinophil or human monocytic cell line (THP-1), the CCR receptor-inhibiting activities were studied.

Human peripheral blood eosinophils or THP-1 cells were suspended in RPMI-1640 culture medium containing 1% fetal calf serum (FCS) and cultured at 37° C. for 30 minutes in the presence of 5 μM of Fura-2/AM (DOJINDO LABORATORIES). The cells were washed twice with assay buffer (140 mM NaCl, 10 mM KCl, 1.8mM CaCl$_2$, 1 mM MgCl$_2$, 1 mM Na$_2$HPO$_4$, 25mM HEPES, 5 mM glucose, 1% BSA; pH7.4) at 4° C. to remove Fura-2/AM which was not taken into the cells. The cells were suspended in the assay buffer to a final cell density of 1×10$^6$ cells/ml and the cell suspension was stored in the dark until assay. The calcium levels in the cells were measured by using CAF100 commercially available from Nippon Koden Co. That is, 490 μl of the suspension of the cells loaded with Fura-2 was placed in a cuvette and the cuvette was set in CAF100. After the fluorescence intensities at 340 nm and 380 nm of excitation, as well as the ratio thereof, were stabilized, 10 μl of 250 μM solution of each test compound was injected. The change in the calcium level in the cells within one minute from the stimulation was measured in terms of the ratio (F340/F380) of the intensity of the excitation light at 340 nm to that of the light at 380 nm, and the intracellular calcium level induced by the stimulation was defined as the peak of the ratio. One minute after exposure of the cells to each test compound, the cells were stimulated with eotaxin (5 ng/ml), RANTES (40 ng/ml) or MCP-1 (10 ng/ml). It is thought that the responses by THP-1 cells to RANTES and MCP-1 are mediated through CCR1 and CCR2, respectively; The response of eosinophils to eotaxin is thought to be mediated through CCR3. The increase of the intracellular calcium level was compared to that of the corresponding case wherein the cells were not treated with the test compound. The results of the inhibitory activity of the test compounds are shown in Table 1.

TABLE 1

| Test Compound | CCR1 | CCR2 | CCR3 |
| --- | --- | --- | --- |
| 5 | 12.9 | 48.1 | |
| 11 | 9.1 | NE | 3.6 |
| 26 | 4.1 | NE | 0.3 |
| 28 | 9.3 | NE | 1.4 |
| 38 | 16.0 | >160 | 0.5 |

The values indicate IC$_{50}$ (μM). "NE" means that the IC$_{50}$ was more than 160 μM so that the inhibitory activity was not observed.

As is apparent from the above test results, the compounds represented by Formula I and the salts thereof have inhibitory activities against CCR.

What is claimed is:

1. A triazolo derivative of the Formula I:

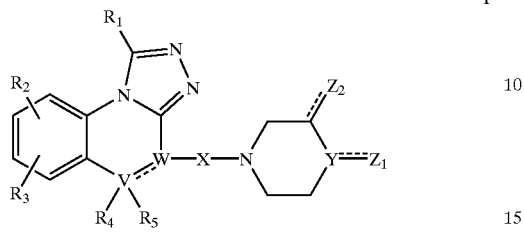

wherein,

W represents a carbon atom or a nitrogen atom,

X represents a $C_2-C_6$ straight chain alkyl group, a $C_3-C_8$ branched alkyl group, a $C_2-C_6$ fluoroalkyl group, Formula II:

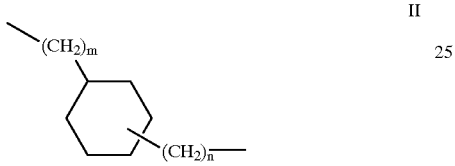

wherein m and n represent integers of 0 to 6, and —$(CH_2)_n$— is bound to the position of any one of 2-, 3- and 4-position in the cyclohexane ring or Formula III:

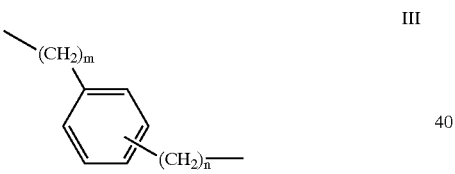

wherein m and n represent integers of 0 to 6, and —$(CH_2)_n$— is bound to the position of any one of 2-, 3- and 4-position in the benzene ring;

Y represents a carbon atom or a nitrogen atom; --- represents a single bond or a double bond; $Z_1$ and $Z_2$, which may or may not simultaneously exist, each represents $C_6-C_{18}$ substituted or non-substituted cyclohexyl group, indole-3-yl group, imidazoyl group, furyl group, thienyl group, pyrrolyl group, pyridyl group or $QCR_6R_7R_8$, with the proviso that in cases where $Z_1$ and $Z_2$ represent $QCR_6R_7R_8$, Q may or may not exist, and when Q exists, Q is selected from the group consisting of an oxygen atom, a sulfur atom and a nitrogen atom; $R_6$ represents hydrogen or hydroxyl group; $R_7$ and $R_8$, which may be the same or different, represent hydrogen, $C_1-C_6$ straight alkyl group, $C_3-C_8$ branched alkyl group, or one selected from the group consisting of $C_6-C_{16}$ substituted or non-substituted phenyl group, $C_{10}-C_{16}$ substituted or non-substituted naphthyl group and $C_6-C_{16}$ substituted or non-substituted cycloalkyl group, which phenyl group, naphthyl group or cycloalkyl group is bound through $C_0-C_6$ methylene chain; V represents a carbon atom or a nitrogen atom; $R_1$ represents $C_1-C_6$ straight alkyl group or aryl group;

$R_2$ and $R_3$, which may be the same or different, each is selected from the group consisting of hydrogen, $C_1-C_6$ straight alkyl group, $C_1-C_6$ straight alkoxyl group, $C_3-C_8$ branched alkyl group, $C_3-C_8$ branched alkoxyl group, hydroxyl group, chloro, bromo, fluoro, amino group, monoalkylamino group in which the alkyl group has 1 to 6 carbon atoms, dialkylamino group in which each alkyl group has 2 to 6 carbon atoms, trifluoromethyl group, and nitro group; in cases where V and W are carbon atoms and where V and W are bound through double bond, $R_4$ does not exist, and $R_5$ represents hydrogen, $C_1-C_6$ straight alkyl group, $C_1-C_6$ straight alkoxyl group, $C_3-C_8$ branched alkyl group, $C_3-C_8$ branched alkoxyl group, or represents one selected from the group consisting of $C_6-C_{16}$ substituted or non-substituted phenyl group, $C_{10}-C_{16}$ substituted or non-substituted naphthyl group and $C_6-C_{16}$ substituted or non-substituted cycloalkyl group, which phenyl group, naphthyl group or cycloalkyl group is bound through $C_0-C_6$ methylene chain; in cases where V is nitrogen atom and W is carbon atom and where V and W are bound through double bond, both $R_4$ and $R_5$ do not exist; in cases where V is carbon atom, W is nitrogen atom or carbon atom, and V and W are bound through single bond, $R_4$ and $R_5$ cooperatively represent oxo group; wherein the substituent(s) in said substituted phenyl group, substituted naphthyl group and substituted cycloalkyl group is (are) 1 to 5 $C_1-C_6$ straight alkyl group(s), $C_3-C_6$ branched alkyl group(s), phenyl group(s), phenoxy group(s), naphthyl group(s), cyclopentyl group(s) or cyclohexyl group(s)) or a pharmaceutically acceptable salt thereof.

2. The triazolo derivative or a pharmaceutically acceptable salt thereof according to claim 1, wherein said triazolo derivative is represented by the Formula IV:

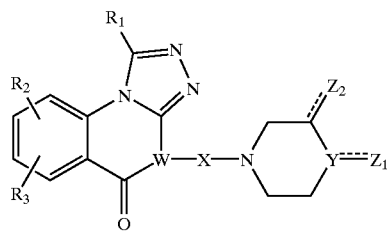

wherein W, X, Y, $Z_1$, $Z_2$, $R_1$, $R_2$ and $R_3$ represent the same meanings described in claim 1.

3. The triazolo derivative or a pharmaceutically acceptable salt thereof according to claim 1, wherein said triazolo derivative is represented by the Formula V:

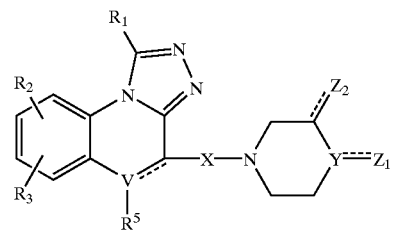

wherein W, X, Y, $Z_1$, $Z_2$, $R_1$, $R_2$, $R_3$ and $R_5$ represent the same meanings described in claim 1.

4. A pharmaceutical composition comprising an effective amount of the triazolo derivative or a pharmaceutically acceptable salt thereof according to any one of claims 1 to 3 and a pharmaceutically acceptable carrier.

5. The composition of claim 4, wherein said composition is a chemokine inhibitor.

6. The composition of claim 5, where said chemokine inhibitor acts by way of a chemokine receptor.

7. The composition of claim 5, wherein said chemokine inhibitor is effective against a CC chemokine.

8. The composition of claim 5, wherein said chemokine inhibitor is effective against a $CCR_1$, $CCR_2$ or $CCR_3$ chemokine.

9. A method of treating a patient suffering from an inflammatory disease, allergic disease, or autoimmune disease caused by infiltration by leukocytes comprising administering an effective amount of the composition of claim 4.

10. A method of treating a patient suffering from an inflammatory disease, allergic disease, or autoimmune disease caused by infiltration by leukocytes comprising administering an effective amount of the composition of claim 5.

11. A method of treating a patient suffering from an inflammatory disease, allergic disease, or autoimmune disease caused by infiltration by leukocytes comprising administering an effective amount of the composition of claim 6.

12. A method of treating a patient suffering from an inflammatory disease, allergic disease, or autoimmune disease caused by infiltration by leukocytes comprising administering an effective amount of the composition of claim 7.

13. A method of treating a patient suffering from an inflammatory disease, allergic disease, or autoimmune disease caused by infiltration by leukocytes comprising administering an effective amount of the composition of claim 8.

* * * * *